(12) United States Patent
Siebel et al.

(10) Patent No.: US 9,249,224 B2
(45) Date of Patent: Feb. 2, 2016

(54) HUMAN GROWTH HORMONE RECEPTOR ANTAGONIST ANTIBODIES AND METHODS OF USE THEREOF

(71) Applicant: RINAT NEUROSCIENCE CORP., South San Francisco, CA (US)

(72) Inventors: Sara Iva Siebel, Redwood City, CA (US); Edward Derrick Pascua, Oakland, CA (US); Chia-Yang Lin, Palo Alto, CA (US); Javier Fernando Chaparro Riggers, San Mateo, CA (US)

(73) Assignee: RINAT NEUROSCIENCE CORP., South San Francisco, CA (US)

( * ) Notice: Subject to any disclaimer, the term of this patent is extended or adjusted under 35 U.S.C. 154(b) by 0 days.

(21) Appl. No.: 14/367,483

(22) PCT Filed: Dec. 10, 2012

(86) PCT No.: PCT/IB2012/057151
§ 371 (c)(1),
(2) Date: Jun. 20, 2014

(87) PCT Pub. No.: WO2013/093707
PCT Pub. Date: Jun. 27, 2013

(65) Prior Publication Data
US 2014/0356359 A1 Dec. 4, 2014

Related U.S. Application Data

(60) Provisional application No. 61/579,618, filed on Dec. 22, 2011.

(51) Int. Cl.
*C07K 16/28* (2006.01)
*A61K 39/395* (2006.01)
*A61K 39/00* (2006.01)

(52) U.S. Cl.
CPC ....... *C07K 16/2869* (2013.01); *A61K 39/39558* (2013.01); *C07K 16/2863* (2013.01); *A61K 2039/505* (2013.01); *C07K 2317/24* (2013.01); *C07K 2317/41* (2013.01); *C07K 2317/76* (2013.01); *C07K 2317/92* (2013.01)

(58) Field of Classification Search
CPC ........... C07K 16/2863; C07K 16/2869; C07K 2317/24; C07K 2317/41; C07K 2317/76; C07K 2317/92; A61K 29/39558; A61K 2039/505; A61K 2300/00
See application file for complete search history.

(56) References Cited

U.S. PATENT DOCUMENTS 5,057,417 A 10/1991 Hammonds
7,612,178 B2 * 11/2009 Hariharan et al. ......... 530/387.1

FOREIGN PATENT DOCUMENTS

WO 2007100640 A2 9/2007

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
Chhabra, Y., et al., "Role of the growth hormone-IGF-1 axis in cancer," Expert Review of Endocrinology & Metabolism, 2011, 71-84, vol. 6, No. 1.
Clemmons, D., et al., "Optimizing Control of Acromegaly: Integrating a Growth Hormone Receptor Antagonist into the Treatment Algorithm," The Journal of Clinical Endocrinology & Metabolism, 2003, 4759-4767, vol. 88, No. 10.
Elbashir, M., et al., "Monoclonal antibodies to the pituitary growth-hormone receptor by the anti-idiotypic approach," Biochemistry Journal, 1990, 467-474, vol. 266.
Flyvbjerg, A., "Potential use of growth hormone receptor antagonist in the treatment of diabetic kidney disease," Growth Hormone & IGF Research, Supplement A, 2001, S115-S119.
International Report on Patentability Publication No. WO 2013/093707, Appln. No. PCT/IB2012/057151 issued Jun. 24, 2014.
International Search Report for Publication No. WO2013/093707, Appln. No. PCT/IB2012/057151 completed on Mar. 13, 2013.
Jakobovits, A., et al., "From XenoMouse technology to panitumumab, the first fully human antibody product from transgenic mice," Nature Biotechnology, 2007, 1134-1143, vol. 25, No. 10.
Jiang, J., et al., "Inhibitory GH Receptor Extracellular Domain Monoclonal Antibodies: Three-Dimensional Epitope Mapping," Endocrinology, 2011, 4777-4788, vol. 152, No. 12.
Kohn, D., et al., "Growth hormone receptor antagonists," Minerva Endocrinologica, 2002, 287-298, vol. 27, No. 4.
Kopchick, J., et al., "Growth Hormone Receptor Antagonists: Discover, Development, and Use in Patients with Acromegaly," Endocrine Reviews, 2002, 623-646, vol. 23, No. 5.
Lattuada, D., et al., "Monoclonal Antibody Against Human Growth Hormone Receptor," Hybridoma, 2000, 177-183, vol. 19, No. 2.
Muller, A., et al., "Growth Hormone Receptor Antagonists," The Journal of Clinical Endocrinology & Metabolism, 2004, 1503-1511, vol. 89, No. 4.
Rowland, J., et al, "In Vivo Analysis of Growth Hormone Receptor Signaling Domains and Their Associated Transcripts," Molecular and Cellular Biology, 2005, 66-77, vol. 25, No. 1.
Rowlinson, S., et al., "An agonist-induced conformational change in the growth hormone receptor determines the choice of signalling pathway," Nature Cell Biology, 2008, 740-759, vol. 10, No. 6.
Surya, S., et al., "GH Receptor Antagonist: Mechanism of Action and Clinical Utility," Reviews in Endocrine & Metabolic Disorders, 2005, 5-13, vol. 6, No. 1.

(Continued)

*Primary Examiner* — Robert Landsman
(74) *Attorney, Agent, or Firm* — Susan L. Wang

(57) ABSTRACT

The present invention provides antagonizing antibodies that bind to growth hormone receptor (GHR). The invention further relates to therapeutic methods for use of these antibodies to reduce IGF-1 levels and/or for the treatment and/or prevention of diseases associated with excessive IGF-1, including treatment of acromegaly, gigantism, cancer, diabetic nephropathy, arthritis, and lung inflammation.

12 Claims, No Drawings

(56) References Cited

OTHER PUBLICATIONS

Trainer, P., "Treatment of Acromegaly with the Growth Hormone-Receptor Antagonist Pegvisomant," The New England Journal of Medicine, 2000, 1171-1177, vol. 342, No. 16.

Wan, Y., et al., "Epitope Map for a Growth Hormone Receptor Agonist Monoclonal Antibody, MAb 263," Molecular Endocrinology, 2003, 2240-2250, vol. 17, No. 11.

Written Opinion of the International Searching Authority Publication No. WO 2013/093707, Appln. No. PCT/IB2012/057151.

Yang, N., et al., "Activation of Growth Hormone Receptors by Growth Hormone and Growth Hormone Antagonist Dimers: Insights into Receptor Triggering," Molecular Endocrinology, 2008, 978-988, vol. 22, No. 4.

* cited by examiner

HUMAN GROWTH HORMONE RECEPTOR ANTAGONIST ANTIBODIES AND METHODS OF USE THEREOF

This application is a §371 filing of PCT/IB2012/057151 filed Dec. 10, 2012, which claims the benefit of priority to U.S. Provisional Application No. 61/579,618 filed Dec. 22, 2011; the entire contents of which are incorporated herein by reference.

REFERENCE TO SEQUENCE LISTING

This application is being filed electronically via EFS-Web and includes an electronically submitted sequence listing in .txt format. The .txt file contains a sequence listing entitled "PC33925A_SequenceListing_ST25.txt" created on Jun. 17, 2014, and having a size of 79 KB. The sequence listing contained in this .txt file is part of the specification and is herein incorporated by reference in its entirety.

FIELD

The present invention relates to antibodies, e.g., full length antibodies or antigen-binding portions thereof, that antagonize the activity of human growth hormone receptor (GHR). More specifically, the invention relates to compositions comprising antagonist GHR antibodies and methods of using these antibodies as a medicament. The antagonist GHR antibodies can be used therapeutically to lower IGF-1 levels in plasma and/or tissue, and can be used in the prevention and/or treatment of cancer, diabetic nephropathy, arthritis, lung inflammation, and growth disorders, including acromegaly and gigantism.

BACKGROUND

Growth hormone (somatotropin) (GH) is a 22 kDa protein that is synthesized in and secreted by the anterior pituitary. Kopchick et al., 2002, Endocrine Reviews, 23(5):623-646. GH functions as a central endocrine regulator of growth both by acting directly on tissues and stimulating the release of insulin-like growth factor-1 (IGF-1) by the liver and other tissues. Okada et al., 2001, Trends in Molecular Medicine 7(3):126-132. In turn, IGF-1 acts on tissues to stimulate body growth.

GH signals through the growth hormone receptor (GHR), a single pass transmembrane protein with no intrinsic tyrosine kinase activity. The growth hormone receptor (GHR) is a class 1 cytokine receptor. Waters et al., 2006, Journal of Molecular Endocrinology, 36, 1-7. GHR signalling involves the role of at least three major pathways, STATs, MAPK, and PI3-kinase/Akt. The current understanding of GHR signaling is that GHR exists as a constitutive homodimer, with signal transduction by ligand-induced realignment of receptor subunits. Brown, R. J. et al., 2005, Nature Struct. Mol. Biol. 12:814-821. At present, the mechanism by which GH binding converts the inactive predimerized GHR to its active signaling conformation is uncertain. Yang et al., 2008, Mol. Endocrinol 22(4):978-988. The interaction of GH with dimerized GHR is mediated by two asymmetric binding sites on GH, each with distinct affinity. Yang et al., 2008.

GHRs are ubiquitously distributed. While originally identified in hepatic tissue, they are known to be present in liver, bone, kidney, adipose, muscle, eye, brain, and heart, as well as in immune tissues like B cells, lymphocytes, spleen, and thymus. GHR antagonists, such as Pegvisomant (SOMAVERT®), have been developed for use as drugs to treat, for example, acromegaly (Kopchick et al., 2002).

Abnormally high GH levels have been associated with a number of disorders. The two classic disorders which are directly caused by high levels of GH are acromegaly and gigantism. Changes associated with acromegaly include coarsening of body hair, thickening and darkening of the skin, enlargement and overactivity of sebaceous and sweat glands such that patients frequently complain of excessive perspiration and offensive body odor, overgrowth of the mandible, cartilaginous proliferation of the larynx causing a deepening of the voice, and enlargement of the tongue. In addition, excess GH in these patients is responsible for proliferation of articular cartilage which may undergo necrosis and erosion and endoneural fibrous proliferation which causes peripheral neuropathies. Excess GH also increases tubular reabsorption of phosphate and leads to mild hyperphosphatemia. Many of these symptoms are also seen in patients with gigantism.

Current treatments for acromegaly and gigantism typically aim to lower IGF-1 levels in plasma and/or tissue through either destruction of the pituitary or drug treatment. The role of IGF-1 in GH-mediated disorders, such as acromegaly and gigantism is well recognized. Melmed et al., 1994, Amer. J. Med. 97:468-473.

Current treatment for acromegaly and gigantism include pituitary ablation, radiation treatment, bromocriptine mesylate, somatostatin analogs, and Pegvisomant. Pituitary ablation is a surgical procedure and, like any surgical procedure, is associated with a significant risk of complications including mortality. There are also risks associated with radiation treatment of the pituitary as well. In addition, the efficacy of radiation treatment may be delayed for several years. Moreover, these treatment modalities are not specific against that part of the pituitary that produces GH and may adversely affect adjacent tissue as well. Bromocriptine mesylate is a dopamine like drug which suppresses the production of GH. Recently, octreotide, a long-acting somatostatin analog has also been used to treat patients with acromegaly and gigantism which is refractory to surgery, radiation, and/or bromocriptine mesylate. Somatostatin analogs inhibit insulin secretion and long-term and are associated with increase risk of insulin resistance, impaired insulin secretion, and diabetes. Baldelli et al., 2003, Clin. Endocrinol. (Oxf). 59(4):492-499. Pegvisomant is a GH antagonist comprising a recombinantly produced PEGylated human GH analog. Treatment with pegvisomant currently involves daily dosing subcutaneously.

Although anti-human GHR antibodies have been described, it has been difficult to identify monoclonal antibodies that specifically bind to both human and non-human primate GHR, are high affinity, have high specificity, and have potent antagonizing activity.

SUMMARY

A high affinity, antagonizing antibody to human GHR that also specifically binds to non-human primate GHR would make a superior therapeutic agent. The high affinity binding coupled with binding to cynomolgus monkey GHR result in a therapeutic with a reduced dosing frequency compared with pegvisomant without effect on insulin secretion which can be used both for preclinical evaluation of safety, activity and/or pharmacokinetic profile of these binding domains in primates and, in the identical form, as drugs in humans. This invention relates to antagonist antibodies that selectively interact with and inhibit human GHR function, and also specifically bind to cynomolgus monkey GHR.

In some embodiments, the invention provides an isolated antagonist antibody which interacts with GHR and, when administered to an individual, lowers the IGF-1 levels in plasma and/or tissue of the individual. The antibody can be, for example, a monoclonal antibody or human, humanized, or chimeric antibody.

In some embodiments, the invention provides an isolated GHR antagonist antibody that specifically binds to human and cynomolgus monkey GHR and, when administered to a subject, lowers a level of IGF-1 in blood of said subject.

In some embodiments, the GHR antagonist antibody can comprise an antigen binding region that competes with monoclonal antibody SS1 for binding to human GHR. In some embodiments, the GHR antagonist antibody can recognize an epitope that is the same as or overlaps with the epitope on human GHR recognized by monoclonal antibody SS1. In some embodiments, the GHR antagonist antibody can bind to human GHR with an equilibrium dissociation constant of less than about 10 nM. In some embodiments, the antibody can bind to human GHR with an equilibrium dissociation constant of less than about 250 nM, less than about 100 nM, or less than about 10 nM.

In some embodiments, the GHR antagonist antibody can comprise a heavy chain variable region and a light chain variable region.

In some embodiments, the invention provides an isolated GHR antagonist antibody that specifically binds to GHR and comprises a heavy chain variable region (VH) complementary determining region one (CDR1) comprising the amino acid sequence of SEQ ID NO: 1, 15 or 16, a VH CDR2 comprising the amino acid sequence of SEQ ID NO: 114 or 115, a VH CDR3 comprising the amino acid sequence of SEQ ID NO: 118, a light chain variable region (VL) CDR1 comprising the amino acid sequence of SEQ ID NO: 99, a VL CDR2 comprising the amino acid sequence of SEQ ID NO: 5, and a VL CDR3 comprising the amino acid sequence of SEQ ID NO: 106.

In some embodiments, the invention provides an isolated GHR antagonist antibody that specifically binds to growth hormone receptor (GHR) and comprises a heavy chain variable region (VH) comprising a VH complementary determining region one (CDR1), VH CDR2, and VH CDR3 of the VH sequence of SEQ ID NO: 8; and a light chain variable region (VL) comprising a VL CDR1, VL CDR2, and VL CDR3.

In some embodiments, the VL can comprise a CDR1, VL CDR2, and VL CDR3 of the VL sequence of SEQ ID NO: 7.

In some embodiments, the antibody can comprise a VH CDR1 comprising the amino acid sequence of SEQ ID NO: 1, 15 or 16, a VH CDR2 comprising the amino acid sequence of SEQ ID NO: 2 or 17, a VH CDR3 comprising the amino acid sequence of SEQ ID NO: 3, a VL CDR1 comprising the amino acid sequence of SEQ ID NO: 4, a VL CDR2 comprising the amino acid sequence of SEQ ID NO: 5, and a VL CDR3 comprising the amino acid sequence of SEQ ID NO: 6.

In some embodiments, the antibody can comprise a VH comprising the amino acid sequence of SEQ ID NO: 8 or a variant thereof with one or several conservative amino acid substitutions in residues that are not within a CDR, and a VL comprising the amino acid sequence of SEQ ID NO: 7 or a variant thereof with one or several amino acid substitutions in amino acids that are not within a CDR.

In some embodiments, the antibody can further comprise an immunologically inert constant region. In some embodiments, the antibody can have an isotype that is selected from the group consisting of $IgG_2$, $IgG_{2\Delta a}$, $IgG_4$, $IgG_{4\Delta b}$, $IgG_{4\Delta c}$, $IgG_4$ S228P, $IgG_{4\Delta b}$ S228P and $IgG_{4\Delta c}$ S228P. In some embodiments, the constant region can be aglycosylated Fc.

In some embodiments, the antibody can comprise a heavy chain comprising the amino acid sequence of SEQ ID NO: 134 or 133, and a light chain comprising the amino acid sequence of SEQ ID NO: 135.

The invention also provides pharmaceutical compositions comprising any of the GHR antagonist antibodies described herein.

The invention also provides cell lines that recombinantly produce any of the GHR antagonist antibodies described herein.

The invention also provides nucleic acids encoding any of the GHR antagonist antibodies described herein. The invention also provides nucleic acids encoding a heavy chain variable region and/or a light chain variable region of any of the GHR antagonist antibodies described herein.

The invention also provides kits comprising an effective amount of any of the GHR antagonist antibodies described herein.

Also provided are methods for identifying an antibody that specifically binds to human and cynomolgus monkey GHR. In some embodiments, the method comprises: contacting an antibody that specifically binds to human GHR with a polypeptide comprising the amino acid sequence of SEQ ID NO: 145, and determining binding of the antibody to the polypeptide. In some embodiments, the method can further comprise selecting an antibody that specifically binds to the amino acid sequence of SEQ ID NO: 145. In some embodiments, determination of binding can be carried out using, for example, an ELISA, a biosensor, or an affinity column.

Also provided are methods for reducing a level of insulin-like growth factor-1 (IGF-1) in blood of an individual in need thereof, comprising administering to the individual a therapeutically effective amount of any of the GHR antagonist antibodies described herein. Also provided are GHR antagonist antibodies for use in reducing a level of IGF-1 in blood of an individual in need thereof. In some embodiments, the level of IGF-1 is reduced at least about 40% compared to an IGF-1 level prior to administration. In some embodiments, the level of IGF-1 is reduced at least about 60% compared to an IGF-1 level prior to administration.

In some embodiments, the GHR antagonist antibody can be administered parenterally.

Also provided are methods for treating a disease associated with excessive IGF-1 expression in an individual comprising administering to the subject in need thereof an effective amount of any of the GHR antagonist antibodies described herein. Also provided are GHR antagonist antibodies for use in the treatment or prevention of a disease associated with excessive IGF-1. In some embodiments, the disease is acromegaly. In some embodiments, the disease is gigantism. In some embodiments, the disease is diabetic nephropathy. In some embodiments, the disease is arthritis. In some embodiments, the disease is lung inflammation.

In some embodiments, the disease is cancer. In some embodiments, the cancer is selected from the group consisting of bladder cancer, breast cancer, cervical cancer, colon cancer, gastric cancer, glioblastoma, head and neck cancer, kidney cancer, oral cancer, ovarian cancer, pancreatic cancer, prostate cancer, skin cancer, leukemia, lymphoma, and multiple myeloma. The skin cancer can be, for example, melanoma.

In some embodiments, the invention provides a method of inhibiting tumor growth or progression in an individual who has a tumor, comprising administering to the subject in need thereof an effective amount of any of the GHR antagonist antibodies described herein. Also provided are GHR antagonist antibodies for use in inhibiting tumor growth or progression in an individual who has a tumor.

In some embodiments, the invention provides a method of inhibiting metastasis of cancer cells in an individual, comprising administering to the subject in need thereof an effective amount of any of the GHR antagonist antibodies described herein. Also provided are GHR antagonist antibodies for use in inhibiting metastasis of cancer cells.

In some embodiments, the invention provides a method of inducing tumor regression in an individual who has a tumor, comprising administering to the subject in need thereof any of the GHR antagonist antibodies described herein. Also provided are GHR antagonist antibodies for use in inducing tumor regression.

DETAILED DESCRIPTION OF THE INVENTION

The present invention relates to antibodies, peptides, and aptamers that antagonize the function of extracellular GHR including its interaction with GH. More specifically, the invention relates to methods of making antagonist GHR antibodies, compositions comprising these antibodies, and methods of using these antibodies as a medicament. The antagonist GHR antibodies can be used to lower plasma IGF-1 levels, and can be used in the prevention and/or treatment of GH-related disorders, including, for example, gigantism, acromegaly, diabetic nephropathy, arthritis, lung inflammation, and certain cancers.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

The following terms, unless otherwise indicated, shall be understood to have the following meanings: The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, unless otherwise specified, fusion proteins comprising an antigen binding portion, and any other modified configuration of the immunoglobulin molecule that comprises an antigen recognition site. Antigen binding portions include, for example without limitation, Fab, Fab', F(ab')$_2$, Fd, Fv, domain antibodies (dAbs, e.g., shark and camelid antibodies), fragments including complementarity determining regions (CDRs), single chain variable fragment antibodies (ScFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$ and IgA$_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonincal class as the subject variable region (Chothia and Lesk, J Mol Biol 196(4): 901-917, 1987).

As known in the art, a "constant region" of an antibody refers to the constant region of the antibody light chain or the constant region of the antibody heavy chain, either alone or in combination.

A "complementary determining region" or "CDR" of a variable domain are the amino acid residues within the variable region that are identified in accordance with the definitions of the Kabat, Chothia, the accumulation of both Kabat, Chothia, extended, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the loop structures originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

The term "monoclonal antibody" (Mab) refers to an antibody that is derived from a single copy or clone, including e.g., any eukaryotic, prokaryotic, or phage clone, and not the method by which it is produced. Preferably, a monoclonal antibody of the invention exists in a homogeneous or substantially homogeneous population.

As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "epitope" refers to that portion of a molecule capable of being recognized by and bound by an antibody at one or more of the antibody's antigen-binding regions. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to GHR, e.g., the antibodies compete for binding to the antigen.

As used herein, the term "GHR" refers to any form of GHR and variants thereof that retain at least part of the activity of GHR. Unless indicated differently, such as by specific reference to human GHR, GHR includes all native sequences of mammalian species of GHR, e.g., human, canine, feline, equine, and bovine. One exemplary GHR is found as Genbank Accession Number AAA52555 (SEQ ID NO: 140).

As used herein, a "GHR antagonist antibody" refers to an antibody that is able to inhibit GHR biological activity and/or downstream pathway(s) mediated by GHR signaling. A GHR antagonist antibody encompasses antibodies that block, antagonize, suppress or reduce (to any degree including significantly) GHR biological activity, including downstream pathways mediated by GHR signaling, such as GH interaction and/or elicitation of a cellular response to GH. For purpose of the present invention, it will be explicitly understood that the term "GHR antagonist antibody" encompasses all the previously identified terms, titles, and functional states and characteristics whereby the GHR itself, a GHR biological activity (including but not limited to its ability to mediate any aspect of insulin-like growth factor-1 (IGF-1) expression), or the consequences of the biological activity, are substantially nullified, decreased, or neutralized in any meaningful degree. In some embodiments, a GHR antagonist antibody binds GHR and prevents interaction with GH. In some embodiments, a GHR antagonist antibody binds GHR and prevents GHR dimerization. Examples of GHR antagonist antibodies are provided herein.

As used herein, the term "clinically meaningful" means at least a 15% reduction in serum IGF-1 levels in humans or at least a 15% reduction in total serum IGF-1 in mice. It is clear that measurements in plasma or serum can serve as surrogates for measurement of levels in blood.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, an antibody "interacts with" GHR when the equilibrium dissociation constant is equal to or less than 20 nM, preferably less than about 6 nM, more preferably less than about 1 nM, most preferably less than about 0.2 nM, as measured by the methods disclosed herein in Example 2.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a GHR epitope is an antibody that binds this epitope with greater affinity, avidity, more readily, and/or with greater duration than it binds to other GHR epitopes or non-GHR epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3. As is known in the art, an Fc region can be present in dimer or monomeric form. As is known in the art, an Fc region can be present in dimer or monomeric form.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, "treatment" is an approach for obtaining beneficial or desired clinical results. For purposes of this invention, beneficial or desired clinical results include, but are not limited to, one or more of the following: reducing incidence or amelioration of aberrant IGF-1 levels resulting from excessive GH production, and reducing incidence or amelioration of one or more symptoms of acromegaly, gigantism, or cancer. Excessive production of GH is caused by, for example, pituitary adenomas, or another non-pituitary tumors, including tumors of the lung, pancreas, adrenal glands, or other parts of the brain.

"Reducing incidence" means any of reducing severity (which can include reducing need for and/or amount of (e.g., exposure to) other drugs and/or therapies generally used for this condition), reducing duration, and/or reducing frequency. As is understood by those skilled in the art, individuals may vary in terms of their response to treatment, and, as such, for example, a "method of reducing incidence" reflects administering the alpha-toxin antagonist antibody based on a reasonable expectation that such administration may likely cause such a reduction in incidence in that particular individual.

"Ameliorating" means a lessening or improvement of one or more symptoms as compared to not administering a GHR antagonist antibody. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing serum IGF-1 levels or one or more symptoms of acromegaly, gigantism, or cancer, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals, sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$k_{on}$", as used herein, refers to the rate constant for association of an antibody to an antigen. Specifically, the rate constants ($k_{on}$ and $k_{off}$) and equilibrium dissociation constants are measured using full-length and/or Fab antibody fragments (i.e. univalent) and GHR.

The term "$k_{off}$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

Exemplary methods and materials are described herein, although methods and materials similar or equivalent to those described herein can also be used in the practice or testing of the present invention. The materials, methods, and examples are illustrative only and not intended to be limiting.

Methods for Preventing or Treating Disorders Associated with Excessive IGF-1

In one aspect, the invention provides a method for treating or preventing at least one symptom of a disorder associated with excessive IGF-1 in an individual comprising administering to the individual an effective amount of a GHR antagonist antibody. In some embodiments, the disorder is acromegaly. In other embodiments, the disorder is gigantism. In other embodiments, the disorder is cancer.

In some embodiments, methods may involve identifying an individual at risk for a disease associated with excessive IGF-1. Additionally, methods may include evaluating an individual for risk factors for a disease associated with excessive IGF-1, evaluating an individual for symptoms of disease associated with excessive IGF-1, or diagnosing the individual with disease associated with excessive IGF-1. In certain embodiments, methods may involve implementing steps in which the disease is acromegaly, gigantism, or cancer.

Advantageously, therapeutic administration of the antibody results in lower blood IGF-1. Preferably, blood IGF-1 is at least about 10% lower than before administration. More preferably, blood IGF-1 is at least about 15% lower than before administration of the antibody. More preferably, blood IGF-1 is at least about 20% lower than before administration of the antibody. Yet more preferably, blood IGF-1 is at least 30% lower than before administration of the antibody. Advantageously, blood IGF-1 is at least 40% lower than before administration of the antibody. More advantageously, blood IGF-1 is at least 50% lower than before administration of the antibody. Very preferably, blood IGF-1 is at least 60% lower than before administration of the antibody. Most preferably, blood IGF-1 is at least 70% lower than before administration of the antibody.

In some embodiments, therapeutic administration of the GHR antagonist antibody advantageously results in reduced incidence and/or amelioration of one or more symptoms of acromegaly including, for example without limitation, excessive IGF-1 levels, heavy sweating, offensive body odor, thickened skin, darkened skin, oily skin, small skin outgrowths (skin tags), fatigue, muscle weakness, deepened voice due to enlarged vocal cords and sinuses and/or cartilaginous proliferation of the larynx, severe snoring, sleep apnea, impaired vision, headache, enlarged tongue, back pain, pain in joints, limited mobility in joints, menstrual cycle irregularity, reduced sex drive, erectile dysfunction, enlarged hands, enlarged feet, larger and broadened facial features, protrusion of the lower jaw so the lower teeth extend beyond the upper (underbite), enlarged liver, enlarged heart, enlarged kidneys, enlarged spleen, increased chest size (barrel chest), increased coarse body hair, improper processing of sugars in the diet, diabetes, high blood pressure, increased calcium in the urine, kidney stones, gallstones, swelling of the thyroid gland (goiter), heart disease, arthritis, precancerous growths (polyps) in colon, carpal tunnel syndrome, hypopituitarism, uterine fibroids, peripheral neuropathies resulting endoneural fibrous proliferation, necrosis/or erosion of proliferated articular cartilage, hyperphosphatemia, and spinal cord compression.

An individual suffering from acromegaly can be treated with a GHR antagonist antibody. An individual suitable for GHR antagonist antibody therapy is selected using clinical criteria and prognostic indicators of acromegaly that are well known in the art. Diagnosis or assessment of acromegaly is well-established in the art. Assessment of acromegaly severity may be performed based on tests known in the art, including, for example without limitation, measurement of blood IGF-1 levels, measurement of growth hormone before and after oral glucose challenge, and magnetic resonance imaging (MRI) of the brain to detect pituitary tumor. In some embodiments, ameliorating, controlling, reducing incidence of, or delaying the development or progression of acromegaly and/or symptoms of acromegaly is measured by testing blood IGF-1 levels.

In some embodiments, therapeutic administration of the GHR antagonist antibody advantageously results in reduced incidence and/or amelioration of one or more symptoms of gigantism including, for example without limitation, excessive IGF-1 levels, excessive growth in height, excessive muscle growth, excessive organ growth, delayed puberty, double vision, difficulty with peripheral vision, frontal bossing, prominent jaw, headache, increased sweating, irregular menstruation, large hands, large feet, thick fingers, thick toes, release of breast milk, thickening of the facial features, weakness, adrenal insufficiency, diabetes insipidus, hypogonadism, and hypothyroidism.

An individual suffering from gigantism can be treated with a GHR antagonist antibody. An individual suitable for GHR antagonist antibody therapy is selected using clinical criteria and prognostic indicators of gigantism that are well known in the art. Diagnosis or assessment of gigantism is well-established in the art. Assessment of gigantism severity may be performed based on tests known in the art, including, for example without limitation, computerized tomography (CT) or MRI scan of the head to detect pituitary tumor, measurement of growth hormone before and after oral glucose challenge, measurement of blood prolactin levels, measurement of blood IGF-1 levels, measurement of blood cortisol levels, measurement of blood estradiol levels, measurement of blood testosterone levels, and measurement of thyroid hormone levels. In some embodiments, ameliorating, controlling, reducing incidence of, or delaying the development or progression of gigantism and/or symptoms of gigantism is measured by measuring blood IGF-1 levels.

With respect to all methods described herein, reference to GHR antagonist antibodies also includes compositions comprising one or more additional agents. These compositions may further comprise suitable excipients, such as pharmaceutically acceptable excipients including buffers, which are well known in the art. The present invention can be used alone or in combination with other conventional methods of treatment.

The GHR antagonist antibody can be administered to an individual via any suitable route. It should be apparent to a person skilled in the art that the examples described herein are not intended to be limiting but to be illustrative of the techniques available. Accordingly, in some embodiments, the GHR antagonist antibody is administered to an individual in accord with known methods, such as intravenous administration, e.g., as a bolus or by continuous infusion over a period of time, by intramuscular, intraperitoneal, intracerebrospinal, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, GHR antagonist antibody can be aerosolized using a fluorocarbon formulation and a metered dose inhaler, or inhaled as a lyophilized and milled powder.

In some embodiments, a GHR antagonist antibody is administered via site-specific or targeted local delivery techniques. Examples of site-specific or targeted local delivery techniques include various implantable depot sources of the GHR antagonist antibody or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of a GHR antagonist antibody may be used for administration. In some embodiments, the GHR antagonist antibody may be administered neat. In some embodiments, GHR antagonist antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing (2000).

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

A GHR antagonist antibody can be administered using any suitable method, including by injection (e.g., intraperitoneally, intravenously, subcutaneously, intramuscularly, etc.). GHR antibodies can also be administered via inhalation, as described herein. Generally, for administration of GHR antibodies, an initial candidate dosage can be about 2 mg/kg. For the purpose of the present invention, a typical daily dosage might range from about any of 3 μg/kg to 30 μg/kg to 300 μg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to reduce blood IGF-1 levels. An exemplary dosing regimen comprises administering an initial dose of about 2 mg/kg, followed by a weekly maintenance dose of about 1 mg/kg of the GHR antibody, or followed by a maintenance dose of about 1 mg/kg every other week. However, other dosage regimens may be useful, depending on the pattern of pharmacokinetic decay that the practitioner wishes to achieve. For example, in some embodiments, dosing from one to four times a week is contemplated. In other embodiments dosing once a month or once every other month or every three months is contemplated. The progress of this therapy is easily monitored by conventional techniques and assays. The dosing regimen (including the GHR antagonist antibody used) can vary over time.

For the purpose of the present invention, the appropriate dosage of a GHR antagonist antibody will depend on the GHR antagonist antibody (or compositions thereof) employed, the type and severity of symptoms to be treated, whether the agent is administered for preventive or therapeutic purposes, previous therapy, the patient's clinical history and response to the agent, the patient's blood IGF-1 levels, the patient's synthesis and clearance rate for IGF-1, the patient's clearance rate for the administered agent, and the discretion of the attending physician. Typically the clinician will administer a GHR antagonist antibody until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., excessive IGF-1 levels. Alternatively, sustained continuous release formulations of GHR antagonist antibodies may be appropriate. Various formulations and devices for achieving sustained release are known in the art.

In one embodiment, dosages for an antagonist antibody may be determined empirically in individuals who have been given one or more administration(s) of an antagonist antibody. Individuals are given incremental dosages of a GHR antagonist antibody. To assess efficacy, an indicator of the disease can be followed.

Administration of a GHR antagonist antibody in accordance with the method in the present invention can be continuous or intermittent, depending, for example, upon the recipient's physiological condition, whether the purpose of the administration is therapeutic or prophylactic, and other factors known to skilled practitioners. The administration of a GHR antagonist antibody may be essentially continuous over a preselected period of time or may be in a series of spaced doses.

In some embodiments, more than one antagonist antibody may be present. At least one, at least two, at least three, at least four, at least five different, or more antagonist antibodies can be present. Generally, those GHR antagonist antibodies may have complementary activities that do not adversely affect each other. A GHR antagonist antibody can also be used in conjunction with other GHR antagonists or GH antagonists. For example, one or more of the following GHR antagonists may be used: an anti-sense molecule directed to a GHR (including an anti-sense molecule directed to a nucleic acid encoding GHR), a GHR inhibitory compound (e.g., pegvisomant), and a GHR structural analog. A GHR antagonist antibody can also be used in conjunction with other agents that serve to enhance and/or complement the effectiveness of the agents.

Therapeutic formulations of the GHR antagonist antibody used in accordance with the present invention are prepared for storage by mixing an antibody or peptide having the desired degree of purity with optional pharmaceutically acceptable carriers, excipients or stabilizers (Remington, The Science and Practice of Pharmacy 20th Ed. Mack Publishing (2000)), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the GHR antagonist antibody are prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic GHR antagonist antibody compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Infralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing a GHR antagonist antibody with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

GHR Antagonist Antibodies

The methods of the invention use a GHR antagonist antibody that blocks, suppresses or reduces (including significantly reduces) GHR biological activity, including downstream pathways mediated by GHR signaling. A GHR antagonist antibody should exhibit any one or more of the following characteristics: (a) bind to GHR; (b) block GHR dimerization; (c) block GHR interaction with GH; (d) block or decrease GHR-mediated STAT5 phosphorylation and/or other downstream signaling events; (e) block or decrease GHR-mediated IGF-1 expression; and (f) block GHR interaction with other yet to be identified factors.

For purposes of this invention, the antibody preferably reacts with GHR in a manner that inhibits GHR signaling function and GH interaction. In some embodiments, the GHR antagonist antibody specifically recognizes human and non-human primate GHR. In some embodiments, the GHR antagonist antibody binds human and non-human primate GHR.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the GHR antagonist antibody is a monoclonal antibody. In some embodiments, the antibody is a humanized or human antibody.

The GHR antagonist antibodies may be made by any method known in the art. General techniques for production of human and mouse antibodies are known in the art and/or are described herein.

GHR antagonist antibodies and fragments thereof can be identified or characterized using methods known in the art, whereby reduction, amelioration, or neutralization of GHR biological activity is detected and/or measured. In some embodiments, a GHR antagonist antibody is identified by incubating a candidate agent with GHR and monitoring binding and/or attendant reduction or neutralization of a biological activity of GHR. The binding assay may be performed with purified GHR polypeptide(s), or with cells naturally expressing, or transfected to express, GHR polypeptide(s). In one embodiment, the binding assay is a competitive binding assay, where the ability of a candidate antibody to compete with a known GHR antagonist for GHR binding is evaluated. The assay may be performed in various formats, including the ELISA format. In some embodiments, a GHR antagonist antibody is identified by incubating a candidate antibody with GHR and monitoring binding. In some embodiments, a STAT5 phosphorylation is used to identify a GHR antagonist antibody. For example, a candidate antibody is incubated with cells expressing GHR, and attendant STAT5 phosphorylation is monitored.

Following initial identification, the activity of a candidate GHR antagonist antibody can be further confirmed and refined by bioassays, known to test the targeted biological activities. Alternatively, bioassays can be used to screen candidates directly. Some of the methods for identifying and characterizing GHR antagonist antibody are described in detail in the Examples.

The GHR antagonist antibodies of the invention exhibit one or more of the following characteristics: (a) bind to GHR; (b) block GHR dimerization; (c) block GHR interaction with GH; (d) block or decrease GHR-mediated STAT5 phosphorylation; (e) block or decrease GHR-mediated IGF-1 expression; and (f) block GHR interaction with other yet to be identified factors. Preferably, GHR antibodies have two or more of these features. More preferably, the antibodies have three or more of the features. More preferably, the antibodies have four or more of the features. More preferably, the antibodies have five or more of the features. Most preferably, the antibodies have all six characteristics.

GHR antagonist antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which a GHR antagonist antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with a GHR antagonist antibody. In another example, the epitope to which the GHR antagonist antibody binds can be determined in a systematic screening by using overlapping peptides derived from the GHR sequence and determining binding by the GHR antagonist antibody. According to the gene fragment expression assays, the open reading frame encoding GHR is fragmented either randomly or by specific genetic constructions and the reactivity of the expressed fragments of GHR with the antibody to be tested is determined. The gene fragments may, for example, be produced by PCR and then transcribed and translated into protein in vitro, in the presence of radioactive amino acids. The binding of the antibody to the radioactively labeled GHR fragments is then determined by immunoprecipitation and gel electrophoresis. Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, domain swapping experiments can be performed using a mutant GHR in which various fragments of the GHR polypeptide have been replaced (swapped) with sequences from GHR from another species, or a closely related, but antigenically distinct protein. By assessing binding of the antibody to the mutant GHR, the importance of the particular GHR fragment to antibody binding can be assessed.

Yet another method which can be used to characterize a GHR antagonist antibody is to use competition assays with other antibodies known to bind to the same antigen, i.e., various fragments on GHR, to determine if the GHR antagonist antibody binds to the same epitope as other antibodies. Competition assays are well known to those of skill in the art.

The binding affinity ($K_D$) of a GHR antagonist antibody to GHR can be about 0.001 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, about 2 pM, or about 1 pM. In some embodiments, the binding affinity is less than any of about 250 nM, about 200 nM, about 100 nM, about 50 nM, about 10 nM, about 1 nM, about 500 pM, about 100 pM, about 50 pM, about 20 pM, about 10 pM, about 5 pM, or about 2 pM.

One way of determining binding affinity of antibodies to GHR is by measuring binding affinity of monofunctional Fab fragments of the antibody. To obtain monofunctional Fab fragments, an antibody (for example, IgG) can be cleaved with papain or expressed recombinantly. The affinity of a GHR Fab fragment of an antibody can be determined by surface plasmon resonance (Biacore3000™ surface plasmon resonance (SPR) system, Biacore, INC, Piscataway N.J.) equipped with pre-immobilized streptavidin sensor chips (SA) using HBS-EP running buffer (0.01M HEPES, pH 7.4, 0.15 NaCl, 3 mM EDTA, 0.005% v/v Surfactant P20). Biotinylated GHR can be diluted into HBS-EP buffer to a concentration of less than 0.5 μg/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound Fab while keeping the activity of GHR on the chip for over 200 injections. Typically, serial dilutions (spanning concentrations of 0.1-10× estimated $K_D$) of purified Fab samples are injected for 1 min at 100 μL/minute and dissociation times of up to 2 hours are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any GHR, including human GHR, cynomolgus monkey (cyno) GHR, and mouse GHR, well as different forms of GHR. Binding affinity of an antibody is generally measured at 25° C., but can also be measured at 37° C.

Accordingly, the invention provides any of the following, or compositions (including pharmaceutical compositions) comprising an antibody having a partial light chain sequence and a partial heavy chain sequence as found in Table 1. In Table 1, the underlined sequences are CDR sequences according to Kabat, and the sequences in bold are CDR sequences according to Chothia. The binding affinity of the antibodies to human GHR was determined by Biacore™ analysis and is shown in Table 1.

TABLE 1

| mAb | Light Chain | Heavy Chain | K_D (nM) |
|---|---|---|---|
| SS1 | EIVLTQSPGTLSLSPGERATLSC TATSSVSSSYLDWYQQKPGQA PRLLIYSTSNLASGIPDRFSGSG SGTDFTLTISRLEPEDFAVYYCH QYHRSTPTFGGGTKVEIK (SEQ ID NO: 7) | EVQLVESGGGLVKPGGSLRLS CAASGFTFSDAWMDWVRQAP GKGLEWVAEIRSKANYHATYY AESVKGRFTISRDDSKNTLYLQ MNSLKTEDTAVYYCTLIRDYW GQGTLVTVSS (SEQ ID NO: 8) | Fab: 1.6 at 37° C. |
| SS3 | EIVLTQSPGTLSLSPGERATLSC TATSSVSSSYLNWYQQKPGQA PRLLIYSTSNLASGIPDRFSGSG SGTDFTLTISRLEPEDFAVYYC HQYHRFTPTFGGGTKVEIK (SEQ ID NO: 9) | EVQLVESGGGLVKPGGSLRLS CAASGFTFSDAWMDWVRQAP GKGLEWVAEIRSKANNHATYY AESVKGRFTISRDDSKNTLYLQ MNSLKTEDTAVYYCTLFRDYW GQGTLVTVSS (SEQ ID NO: 10) | Fab: 1.99 at 37° C. IgG_{2Δ4}: 1.7 at 25° C. |
| SS4 | EIVLTQSPGTLSLSPGERATLSC TATSSVSSSYLHWYQQKPGQA PRLLIYSTSNLASGIPDRFSGSG SGTDFTLTISRLEPEDFAVYYC HQYHRSTPTFGGGTKVEIK (SEQ ID NO: 11) | EVQLVESGGGLVKPGGSLRLS CAASGFTFSDAWMDWVRQAP GKGLEWVAEIRSKANNHATYY AESVKGRFTISRDDSKNTLYLQ MNSLKTEDTAVYYCTLYRDYW GQGTLVTVSS (SEQ ID NO: 12) | Fab: 123.86 at 37° C.; 28.40 at 25° C. IgG_{2Δ4}: 43.10 at 25° C. |
| TM1 | EIVLTQSPGTLSLSPGERATLSC TATSSVSSWYLHWYQQKPGQ APRLLIYSTSNLASGIPDRFSGS GSGTDFTLTISRLEPEDFAVYY CHQYHRSTPTFGGGTKVEIK (SEQ ID NO: 13) | EVQLVESGGGLVKPGGSLRLS CAASGFTFSDAWMDWVRQAP GKGLEWVAEIRSKANYHATYY AESVKGRFTISRDDSKNTLYLQ MNSLKTEDTAVYYCTLIRDYW GQGTLVTVSS (SEQ ID NO: 8) | 3.40 at 37° C. (Fab) |
| TM9 | EIVLTQSPGTLSLSPGERATLSC TATSSVSSSYLHWYQQKPGQA PRLLIYSTSNLASGIPDRFSGSG SGTDFTLTISRLEPEDFAVYYC HQYHRGTPTFGGGTKVEIK (SEQ ID NO: 14) | EVQLVESGGGLVKPGGSLRLS CAASGFTFSDAWMDWVRQAP GKGLEWVAEIRSKANNHATYY AESVKGRFTISRDDSKNTLYLQ MNSLKTEDTAVYYCTLIRDYW GQGTLVTVSS (SEQ ID NO: 8) | 3.30 at 37° C. (Fab) |

The invention also provides CDR portions of antibodies to GHR. Determination of CDR regions is well within the skill of the art. It is understood that in some embodiments, CDRs can be a combination of the Kabat and Chothia CDR (also termed "combined CDRs" or "extended CDRs"). In some embodiments, the CDRs are the Kabat CDRs. In other embodiments, the CDRs are the Chothia CDRs. In other embodiments, the CDRs are the extended, AbM, conformational, or contact CDRs. In other words, in embodiments with more than one CDR, the CDRs may be any of Kabat, Chothia, extended, AbM, conformational, contact CDRs or combinations thereof.

Table 2 provides examples of CDR sequences and binding affinities of GHR antagonist antibodies provided herein. Binding affinities were measured at 25° C., except where marked with an asterisk (*). Asterisk denotes binding affinity measured at 37° C.

TABLE 2

GHR antagonist antibodies andantigen-binding CDR sequences according to Kabat (underlined) and Chothia (bold) with binding affinities (K_D)

| MAb | | CDR1 | CDR2 | CDR3 | K_D (nM) |
|---|---|---|---|---|---|
| SS4 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 28.40 |
| | LC | TATSSVSSSYLH (SEQ ID NO: 18) | STSNLAS (SEQ ID NO: 5) | HQYHRSTPT (SEQ ID NO: 6) | |
| SS1 | HC | GFTFSDAWMD (SEQ ID NOs: 1 (whole), 15 and 16) | EIRSKANYHATYYAESVKG (SEQ ID NOs: 17 and 2) | IRDYW (SEQ ID NO: 3) | 1.56* |
| | LC | TATSSVSSSYLN (SEQ ID NO: 4) | STSNLAS (SEQ ID NO: 5) | HQYHRSTPT (SEQ ID NO: 6) | |
| TM1 | HC | GFTFSDAWMD (SEQ ID NOs: 1 (whole), 15 and 16) | EIRSKANYHATYYAESVKG (SEQ ID NOs: 17 and 2) | IRDYW (SEQ ID NO: 3) | 3.40* |
| | LC | TATSSVSSWYLH (SEQ ID NO: 22) | STSNLAS (SEQ ID NO: 5) | HQYHRSTPT (SEQ ID NO: 6) | |

TABLE 2 -continued

GHR antagonist antibodies and antigen-binding CDR sequences
according to Kabat (underlined) and Chothia (bold) with binding affinities (K_D)

| MAb | | CDR1 | CDR2 | CDR3 | $K_D$ (nM) |
|---|---|---|---|---|---|
| TM2 | HC | GFTFSDAWMD (SEQ ID NOs: 1 (whole), 15 and 16) | EIRSKANYHATYYAESVKG (SEQ ID NOs: 17 and 2) | IRDYW (SEQ ID NO: 3) | 4.42* |
| | LC | TATSSVSSFYLH (SEQ ID NO: 23) | STSNLAS (SEQ ID NO: 5) | HQYHRSTPT (SEQ ID NO: 6) | |
| TM3 | HC | GFTFSDAWMD (SEQ ID NOs: 1 (whole), 15 and 16) | EIRSKANYHATYYAESVKG (SEQ ID NOs: 17 and 2) | IRDYW (SEQ ID NO: 3) | 5.70* |
| | LC | TATSSVSSSYLD (SEQ ID NO: 24) | STSNLAS (SEQ ID NO: 5) | HQYHRSTPT (SEQ ID NO: 6) | |
| TM5 | HC | GFTFSDAWMD (SEQ ID NOs: 1 (whole), 15 and 16) | EIRSKANYHATYYAESVKG (SEQ ID NOs: 17 and 2) | IRDYW (SEQ ID NO: 3) | 4.40* |
| | LC | TATSSVSSSYLH (SEQ ID NO: 18) | STSNLAS (SEQ ID NO: 5) | HQYHRFTPT (SEQ ID NO: 25) | |
| TM6 | HC | GFTFSDAWMD (SEQ ID NOs: 1 (whole), 15 and 16) | EIRSKANYHATYYAESVKG (SEQ ID NOs: 17 and 2) | IRDYW (SEQ ID NO: 3) | 7.88* |
| | LC | TATSSVSSSYLH (SEQ ID NO: 18) | STSNLAS (SEQ ID NO: 5) | HQYHRRTPT (SEQ ID NO: 32) | |
| TM7 | HC | GFTFSDAWMD (SEQ ID NOs: 1 (whole), 15 and 16) | EIRSKANYHATYYAESVKG (SEQ ID NOs: 17 and 2) | IRDYW (SEQ ID NO: 3) | 5.73* |
| | LC | TATSSVSSSYLH (SEQ ID NO: 18) | STSNLAS (SEQ ID NO: 5) | HQYHRYTPT (SEQ ID NO: 33) | |
| TM8 | HC | GFTFSDAWMD (SEQ ID NOs: 1 (whole), 15 and 16) | EIRSKANYHATYYAESVKG (SEQ ID NOs: 17 and 2) | IRDYW (SEQ ID NO: 3) | 8.68* |
| | LC | TATSSVSSSYLH (SEQ ID NO: 18) | STSNLAS (SEQ ID NO: 5) | HQYHRHTPT (SEQ ID NO: 34) | |
| TM9 | HC | GFTFSDAWMD (SEQ ID NOs: 1 (whole), 15 and 16) | EIRSKANYHATYYAESVKG (SEQ ID NOs: 17 and 2) | IRDYW (SEQ ID NO: 3) | 3.30* |
| | LC | TATSSVSSSYLHH (SEQ ID NO: 18) | STSNLAS (SEQ ID NO: 5) | HQYHRGTPT (SEQ ID NO: 36) | |
| TM10 | HC | GFTFSDAWMD (SEQ ID NOs: 1 (whole), 15 and 16) | EIRSKANYHATYYAESVKG (SEQ ID NOs: 17 and 2) | IRDYW (SEQ ID NO: 3) | 7.80* |
| | LC | TATSSVSSSYLH (SEQ ID NO: 18) | STSNLAS (SEQ ID NO: 5) | HQYHRSYPT (SEQ ID NO: 37) | |
| TM11 | HC | GFTFSDAWMD (SEQ ID NOs: 1 (whole), 15 and 16) | EIRSKANYHATYYAESVKG (SEQ ID NOs: 17 and 2) | IRDYW (SEQ ID NO: 3) | 7.94* |
| | LC | TATSSVSSSYLH (SEQ ID NO: 18) | STSNLAS (SEQ ID NO: 5) | HQYHRSFPT (SEQ ID NO: 38) | |
| TM12 | HC | GFTFSDAWMD (SEQ ID NOs: 1 (whole), 15 and 16) | EIRSKANYHATYYAESVKG (SEQ ID NOs: 17 and 2) | IRDYW (SEQ ID NO: 3) | 12.74* |
| | LC | TATSSVSSSYLH (SEQ ID NO: 18) | STSNLAS (SEQ ID NO: 5) | HQYHRSIPT (SEQ ID NO: 39) | |
| TM13 | HC | GFTFSDAWMD (SEQ ID NOs: 1 (whole), 15 and 16) | EIRSKANYHATYYAESVKG (SEQ ID NOs: 17 and 2) | IRDYW (SEQ ID NO: 3) | 6.12* |
| | LC | TATSSVSSSYLH (SEQ ID NO: 18) | STSNLAS (SEQ ID NO: 5) | HQYHRSWPT (SEQ ID NO: 40) | |
| TM14 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 3.35* |
| | LC | TATSSVSSSYLD (SEQ ID NO: 24) | STSNLAS (SEQ ID NO: 5) | HQYHRFTPT (SEQ ID NO: 25) | |

TABLE 2 -continued

GHR antagonist antibodies and antigen-binding CDR sequences
according to Kabat (underlined) and Chothia (bold) with binding affinities ($K_D$)

| MAb | | CDR1 | CDR2 | CDR3 | $K_D$ (nM) |
|---|---|---|---|---|---|
| TM15 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 3.35* |
| | LC | TATSSVSSSYLD (SEQ ID NO: 24) | STSNLAS (SEQ ID NO: 5) | HQYHRFTPT (SEQ ID NO: 25) | |
| TM16 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 1.99* |
| | LC | TATSSVSSSYLD (SEQ ID NO: 24) | STSNLAS (SEQ ID NO: 5) | HQYHRFTPT (SEQ ID NO: 25) | |
| TM17 | HC | GFTFSDAWMD (SEQ ID NOs: 1 (whole), 15 and 16) | EIRSKANNHATYYAESVKG (SEQ ID NOs: 19 and 20) | FRDYW (SEQ ID NO: 30) | 16.90* |
| | LC | TATSSVSSSYLD (SEQ ID NO: 24) | STSNLAS (SEQ ID NO: 5) | HQYHRFTPT (SEQ ID NO: 25) | |
| TM18 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 15.21* |
| | LC | TATSSVSSSYLD (SEQ ID NO: 24) | STSNLAS (SEQ ID NO: 5) | HQYHRFTPT (SEQ ID NO: 25) | |
| TM19 | HC | GFTFSDAWMD (SEQ ID NOs: 1 (whole), 15 and 16) | EIRSKANNHATYYAESVKG (SEQ ID NOs: 19 and 20) | IRDYW (SEQ ID NO: 3) | 4.39* |
| | LC | TATSSVSSSYLD (SEQ ID NO: 24) | STSNLAS (SEQ ID NO: 5) | HQYHRFTPT (SEQ ID NO: 25) | |
| SS2 | NC | GFTFSDAWMD (SEQ ID NOs: 1 (whole), 15 and 16) | EIRSKANYHATYYAESVKG (SEQ ID NOs: 17 and 2) | IRDYW (SEQ ID NO: 3) | 4.21* |
| | LC | TATSSVSSSYLD (SEQ ID NO: 24) | STSNLAS (SEQ ID NO: 5) | HQYHRFTPT (SEQ ID NO: 25) | |
| SS3 | HC | GFTFSDAWMD (SEQ ID NOs: 1 (whole), 15 and 16) | EIRSKANNHATYYAESVKG (SEQ ID NOs: 19 and 20) | FRDYW (SEQ ID NO: 30) | 1.99* |
| | LC | TATSSVSSSYLD (SEQ ID NO: 24) | STSNLAS (SEQ ID NO: 5) | HQYHRFTPT (SEQ ID NO: 25) | |
| DM1 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 18.48 |
| | LC | TATSSVSSSYLH (SEQ ID NO: 18) | STSNLAS (SEQ ID NO: 5) | HQYHRFTPT (SEQ ID NO: 25) | |
| DM2 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 86.41 |
| | LC | TATSSVSSSYLH (SEQ ID NO: 18) | STSNLAS (SEQ ID NO: 5) | HQYHRRTPT (SEQ ID NO: 32) | |
| DM3 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 192.54 |
| | LC | TATSSVSSSYLH (SEQ ID NO: 18) | STSNLAS (SEQ ID NO: 5) | HQYHRYTPT (SEQ ID NO: 33) | |
| DM4 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 1128.30 |
| | LC | TATSSVSSSYLH (SEQ ID NO: 18) | STSNLAS (SEQ ID NO: 5) | HQYHRHTPT (SEQ ID NO: 34) | |
| DM5 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 217.35 |
| | LC | TATSSVSSSYLH (SEQ ID NO: 18) | STSNLAS (SEQ ID NO: 5) | HQYHRQTPT (SEQ ID NO: 35) | |

TABLE 2 -continued

GHR antagonist antibodies and antigen-binding CDR sequences
according to Kabat (underlined) and Chothia (bold) with binding affinities ($K_D$)

| MAb | | CDR1 | CDR2 | CDR3 | $K_D$ (nM) |
|---|---|---|---|---|---|
| DM6 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 4.63 |
| | LC | TATSSVSSSYLH (SEQ ID NO: 18) | STSNLAS (SEQ ID NO: 5) | HQYHRGTPT (SEQ ID NO: 36) | |
| DM7 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 7.08 |
| | LC | TATSSVSSSYLH (SEQ ID NO: 18) | STSNLAS (SEQ ID NO: 5) | HQYHRSYPT (SEQ ID NO: 37) | |
| DM8 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 7.55 |
| | LC | TATSSVSSSYLH (SEQ ID NO: 18) | STSNLAS (SEQ ID NO: 5) | HQYHRSFPT (SEQ ID NO: 38) | |
| DM9 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 70.69 |
| | LC | TATSSVSSSYLH (SEQ ID NO: 18) | STSNLAS (SEQ ID NO: 5) | HQYHRSIPT (SEQ ID NO: 39) | |
| DM10 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 6.66 |
| | LC | TATSSVSSSYLH (SEQ ID NO: 18) | STSNLAS (SEQ ID NO: 5) | HQYHRSWPT (SEQ ID NO: 40) | |
| DM11 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 5.76 |
| | LC | TATSSVSSWYLH (SEQ ID NO: 22) | STSNLAS (SEQ ID NO: 5) | HQYHRSTPT (SEQ ID NO: 6) | |
| DM12 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 4.92 |
| | LC | TATSSVSSFYLH (SEQ ID NO: 23) | STSNLAS (SEQ ID NO: 5) | HQYHRSTPT (SEQ ID NO: 6) | |
| DM13 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 7.96 |
| | LC | TATSSVSSSYLD (SEQ ID NO: 24) | STSNLAS (SEQ ID NO: 5) | HQYHRSTPT (SEQ ID NO: 6) | |
| DM14 | HC | GFTFSDAWMD (SEQ ID NOs: 1 (whole), 15 and 16) | EIRSKANNHATYYAESVKG (SEQ ID NOs: 19 and 20) | IYRDYW (SEQ ID NO: 31 (whole) and 21) | 1.82 |
| | LC | TATSSVSSSYLN (SEQ ID NO: 4) | STSNLAS (SEQ ID NO: 5) | HQYHRSTPT (SEQ ID NO: 6) | |
| DM15 | HC | GFTFSDAWMD (SEQ ID NOs: 1 (whole), 15 and 16) | EIRSKANNHATYYAESVKG (SEQ ID NOs: 19 and 20) | TLFRDYW (SEQ ID NO: 30) | 3.05 |
| | LC | TATSSVSSSYLH (SEQ ID NO: 18) | STSNLAS (SEQ ID NO: 5) | HQYHRFTPT (SEQ ID NO: 25) | |
| DM16 | HC | GFTFSDAWMD (SEQ ID NOs: 1 (whole), 15 and 16) | EIRSKANNHATYYAESVKG (SEQ ID NOs: 19 and 20) | TLFRDYW (SEQ ID NO: 30) | 4.73 |
| | LC | TATSSVSSSYLH (SEQ ID NO: 18) | STSNLAS (SEQ ID NO: 5) | HQYHRRTPT (SEQ ID NO: 32) | |
| DM17 | HC | GFTFSDAWMD (SEQ ID NOs: 1 (whole), 15 and 16) | EIRSKANNHATYYAESVKG (SEQ ID NOs: 19 and 20) | TLFRDYW (SEQ ID NO: 30) | 22.03 |
| | LC | TATSSVSSSYLH (SEQ ID NO: 18) | STSNLAS (SEQ ID NO: 5) | HQYHRYTPT (SEQ ID NO: 33) | |

TABLE 2 -continued

GHR antagonist antibodies and antigen-binding CDR sequences
according to Kabat (underlined) and Chothia (bold) with binding affinities (K_D)

| MAb | | CDR1 | CDR2 | CDR3 | K_D (nM) |
|---|---|---|---|---|---|
| DM18 | HC | GFTFSDAWMD (SEQ ID NOs: 1 (whole), 15 and 16) | EIRSKANNHATYYAESVKG (SEQ ID NOs: 19 and 20) | TLFRDYW (SEQ ID NO: 30) | 32.01 |
| | LC | TATSSVSSSYLH (SEQ ID NO: 18) | STSNLAS (SEQ ID NO: 5) | HQYHRHTPT (SEQ ID NO: 34) | |
| DM19 | HC | GFTFSDAWMD (SEQ ID NOs: 1 (whole), 15 and 16) | EIRSKANNHATYYAESVKG (SEQ ID NOs: 19 and 20) | TLFRDYW (SEQ ID NO: 30) | 8.50 |
| | LC | TATSSVSSSYLH (SEQ ID NO: 18) | STSNLAS (SEQ ID NO: 5) | HQYHRQTPT (SEQ ID NO: 35) | |
| DM20 | HC | GFTFSDAWMD (SEQ ID NOs: 1 (whole), 15 and 16) | EIRSKANNHATYYAESVKG (SEQ ID NOs: 19 and 20) | TLFRDYW (SEQ ID NO: 30) | 3.27 |
| | LC | TATSSVSSSYLH (SEQ ID NO: 18) | STSNLAS (SEQ ID NO: 5) | HQYHRGTPT (SEQ ID NO: 36) | |
| DM21 | HC | GFTFSDAWMD (SEQ ID NOs: 1 (whole), 15 and 16) | EIRSKANNHATYYAESVKG (SEQ ID NOs: 19 and 20) | TLFRDYW (SEQ ID NO: 30) | 13.17 |
| | LC | TATSSVSSSYLH (SEQ ID NO: 18) | STSNLAS (SEQ ID NO: 5) | HQYHRSYPT (SEQ ID NO: 37) | |
| DM22 | HC | GFTFSDAWMD (SEQ ID NOs: 1 (whole), 15 and 16) | EIRSKANNHATYYAESVKG (SEQ ID NOs: 19 and 20) | TLFRDYW (SEQ ID NO: 30) | 5.55 |
| | LC | TATSSVSSSYLH (SEQ ID NO: 18) | STSNLAS (SEQ ID NO: 5) | HQYHRSFPT (SEQ ID NO: 38) | |
| DM23 | HC | GFTFSDAWMD (SEQ ID NOs: 1 (whole), 15 and 16) | EIRSKANNHATYYAESVKG (SEQ ID NOs: 19 and 20) | TLFRDYW (SEQ ID NO: 30) | 6.41 |
| | LC | TATSSVSSSYLH (SEQ ID NO: 18) | STSNLAS (SEQ ID NO: 5) | HQYHRSIPT (SEQ ID NO: 39) | |
| DM24 | HC | GFTFSDAWMD (SEQ ID NOs: 1 (whole), 15 and 16) | EIRSKANNHATYYAESVKG (SEQ ID NOs: 19 and 20) | TLFRDYW (SEQ ID NO: 30) | 4.76 |
| | LC | TATSSVSSSYLH (SEQ ID NO: 18) | STSNLAS (SEQ ID NO: 5) | HQYHRSWPT (SEQ ID NO: 40) | |
| DM25 | HC | GFTFSDAWMD (SEQ ID NOs: 1 (whole), 15 and 16) | EIRSKANNHATYYAESVKG (SEQ ID NOs: 19 and 20) | TLFRDYW (SEQ ID NO: 30) | 4.09 |
| | LC | TATSSVSSWYLH (SEQ ID NO: 22) | STSNLAS (SEQ ID NO: 5) | HQYHRSTPT (SEQ ID NO: 6) | |
| DM26 | HC | GFTFSDAWMD (SEQ ID NOs: 1 (whole), 15 and 16) | EIRSKANNHATYYAESVKG (SEQ ID NOs: 19 and 20) | TLFRDYW (SEQ ID NO: 30) | 3.88 |
| | LC | TATSSVSSFYLH (SEQ ID NO: 23) | STSNLAS (SEQ ID NO: 5) | HQYHRSTPT (SEQ ID NO: 6) | |
| DM27 | HC | GFTFSDAWMD (SEQ ID NOs: 1 (whole), 15 and 16) | EIRSKANNHATYYAESVKG (SEQ ID NOs: 19 and 20) | TLFRDYW (SEQ ID NO: 30) | 16.90 |
| | LC | TATSSVSSSYLD (SEQ ID NO: 24) | STSNLAS (SEQ ID NO: 5) | HQYHRSTPT (SEQ ID NO: 6) | |
| DM28 | HC | GFTFSDAWMD (SEQ ID NOs: 1 (whole), 15 and 16) | EIRSKANNHATYYAESVKG (SEQ ID NOs: 19 and 20) | TLFRDYW (SEQ ID NO: 30) | 2.00 |
| | LC | TATSSVSSSYLN (SEQ ID NO: 4) | STSNLAS (SEQ ID NO: 5) | HQYHRSTPT (SEQ ID NO: 6) | |
| DM29 | HC | GFTFSDAWMD (SEQ ID NOs: 1 (whole), 15 and 16) | EIRSKANNHATYYAESVKG (SEQ ID NOs: 19 and 20) | IRDYW (SEQ ID NO: 3) | 2.93 |
| | LC | TATSSVSSSYLH (SEQ ID NO: 18) | STSNLAS (SEQ ID NO: 5) | HQYHRFTPT (SEQ ID NO: 25) | |

TABLE 2 -continued

GHR antagonist antibodies and antigen-binding CDR sequences
according to Kabat (underlined) and Chothia (bold) with binding affinities ($K_D$)

| MAb | | CDR1 | CDR2 | CDR3 | $K_D$ (nM) |
|---|---|---|---|---|---|
| DM30 | HC | GFTFSDAWMD (SEQ ID NOs: 1 (whole), 15 and 16) | EIRSKANNHATYYAESVKG (SEQ ID NOs: 19 and 20) | IRDYW (SEQ ID NO: 3) | 7.08 |
| | LC | TATSSVSSSYLH (SEQ ID NO: 18) | STSNLAS (SEQ ID NO: 5) | HQYHRRTPT (SEQ ID NO: 32) | |
| DM31 | HC | GFTFSDAWMD (SEQ ID NOs: 1 (whole), 15 and 16) | EIRSKANNHATYYAESVKG (SEQ ID NOs: 19 and 20) | IRDYW (SEQ ID NO: 3) | 0.94 |
| | LC | TATSSVSSSYLH (SEQ ID NO: 18) | STSNLAS (SEQ ID NO: 5) | HQYHRYTPT (SEQ ID NO: 33) | |
| DM32 | HC | GFTFSDAWMD (SEQ ID NOs: 1 (whole), 15 and 16) | EIRSKANNHATYYAESVKG (SEQ ID NOs: 19 and 20) | IRDYW (SEQ ID NO: 3) | 8.20 |
| | LC | TATSSVSSSYLH (SEQ ID NO: 18) | STSNLAS (SEQ ID NO: 5) | HQYHRHTPT (SEQ ID NO: 34) | |
| DM33 | HC | GFTFSDAWMD (SEQ ID NOs: 1 (whole), 15 and 16) | EIRSKANNHATYYAESVKG (SEQ ID NOs: 19 and 20) | IRDYW (SEQ ID NO: 3) | 12.94 |
| | LC | TATSSVSSSYLH (SEQ ID NO: 18) | STSNLAS (SEQ ID NO: 5) | HQYHRQTPT (SEQ ID NO: 35) | |
| DM34 | HC | GFTFSDAWMD (SEQ ID NOs: 1 (whole), 15 and 16) | EIRSKANNHATYYAESVKG (SEQ ID NOs: 19 and 20) | HQYHRGTPT (SEQ ID NO: 36) | 1.70 |
| | LC | TATSSVSSSYLH (SEQ ID NO: 18) | STSNLAS (SEQ ID NO: 5) | IRDYW (SEQ ID NO: 3) | |
| DM35 | HC | GFTFSDAWMD (SEQ ID NOs: 1 (whole), 15 and 16) | EIRSKANNHATYYAESVKG (SEQ ID NOs: 19 and 20) | HQYHRSYPT (SEQ ID NO: 37) | 1.80 |
| | LC | TATSSVSSSYLH (SEQ ID NO: 18) | STSNLAS (SEQ ID NO: 5) | IRDYW (SEQ ID NO: 3) | |
| DM36 | HC | GFTFSDAWMD (SEQ ID NOs: 1 (whole), 15 and 16) | EIRSKANNHATYYAESVKG (SEQ ID NOs: 19 and 20) | IRDYW (SEQ ID NO: 3) | 1.92 |
| | LC | TATSSVSSSYLH (SEQ ID NO: 18) | STSNLAS (SEQ ID NO: 5) | HQYHRSFPT (SEQ ID NO: 38) | |
| DM37 | HC | GFTFSDAWMD (SEQ ID NOs: 1 (whole), 15 and 16) | EIRSKANNHATYYAESVKG (SEQ ID NOs: 19 and 20) | IRDYW (SEQ ID NO: 3) | 2.09 |
| | LC | TATSSVSSSYLH (SEQ ID NO: 18) | STSNLAS (SEQ ID NO: 5) | HQYHRSIPT (SEQ ID NO: 39) | |
| DM38 | HC | GFTFSDAWMD (SEQ ID NOs: 1 (whole), 15 and 16) | EIRSKANNHATYYAESVKG (SEQ ID NOs: 19 and 20) | IRDYW (SEQ ID NO: 3) | 1.55 |
| | LC | TATSSVSSSYLH (SEQ ID NO: 18) | STSNLAS (SEQ ID NO: 5) | HQYHRSWPT (SEQ ID NO: 40) | |
| DM39 | HC | GFTFSDAWMD (SEQ ID NOs: 1 (whole), 15 and 16) | EIRSKANNHATYYAESVKG (SEQ ID NOs: 19 and 20) | IRDYW (SEQ ID NO: 3) | 2.03 |
| | LC | TATSSVSSWYLH (SEQ ID NO: 22) | STSNLAS (SEQ ID NO: 5) | HQYHRSTPT (SEQ ID NO: 6) | |
| DM40 | HC | GFTFSDAWMD (SEQ ID NOs: 1 (whole), 15 and 16) | EIRSKANNHATYYAESVKG (SEQ ID NOs: 19 and 20) | IRDYW (SEQ ID NO: 3) | 3.43 |
| | LC | TATSSVSSFYLH (SEQ ID NO: 23) | STSNLAS (SEQ ID NO: 5) | HQYHRSTPT (SEQ ID NO: 6) | |
| DM41 | HC | GFTFSDAWMD (SEQ ID NOs: 1 (whole), 15 and 16) | EIRSKANNHATYYAESVKG (SEQ ID NOs: 19 and 20) | IRDYW (SEQ ID NO: 3) | 1.49 |
| | LC | TATSSVSSSYLD (SEQ ID NO: 24) | STSNLAS (SEQ ID NO: 5) | HQYHRSTPT (SEQ ID NO: 6) | |

TABLE 2-continued

GHR antagonist antibodies and antigen-binding CDR sequences
according to Kabat (underlined) and Chothia (bold) with binding affinities (K_D)

| MAb | | CDR1 | CDR2 | CDR3 | $K_D$ (nM) |
|---|---|---|---|---|---|
| DM42 | HC | GFTFSDAWMD (SEQ ID NOs: 1 (whole), 15 and 16) | EIRSKANNHATYYAESVKG (SEQ ID NOs: 19 and 20) | IRDYW (SEQ ID NO: 3) | 0.27 |
| | LC | TATSSVSSSYLN (SEQ ID NO: 4) | STSNLAS (SEQ ID NO: 5) | HQYHRSTPT (SEQ ID NO: 6) | |
| DM43 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 2.35 |
| | LC | TATSSVSSSYLH (SEQ ID NO: 18) | STSNLAS (SEQ ID NO: 5) | HQYHRFTPT (SEQ ID NO: 25) | |
| DM44 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 54.47 |
| | LC | TATSSVSSSYLH (SEQ ID NO: 18) | STSNLAS (SEQ ID NO: 5) | HQYHRRTPT (SEQ ID NO: 32) | |
| DM45 | HC | GFTFSDAWMD (SEQ ID NOs: 1 (whole), 15 and 16) | EIRSKANFHATYYAESVKG (SEQ ID NOs: 26 and 27 | YRDYW (SEQ ID NO: 21) | 102.70 |
| | LC | TATSSVSSSYLH (SEQ ID NO: 18) | STSNLAS (SEQ ID NO: 5) | HQYHRYTPT (SEQ ID NO: 33) | |
| DM46 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 6.31 |
| | LC | TATSSVSSSYLH (SEQ ID NO: 18) | STSNLAS (SEQ ID NO: 5) | HQYHRHTPT (SEQ ID NO: 34) | |
| DM47 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 39.24 |
| | LC | TATSSVSSSYLH (SEQ ID NO: 18) | STSNLAS (SEQ ID NO: 5) | HQYHRQTPT (SEQ ID NO: 35) | |
| DM48 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 5.21 |
| | LC | TATSSVSSSYLH (SEQ ID NO: 18) | STSNLAS (SEQ ID NO: 5) | HQYHRGTPT (SEQ ID NO: 36) | |
| DM49 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 5.50 |
| | LC | TATSSVSSSYLH (SEQ ID NO: 18) | STSNLAS (SEQ ID NO: 5) | HQYHRSYPT (SEQ ID NO: 37) | |
| DM50 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 6.25 |
| | LC | TATSSVSSSYLH (SEQ ID NO: 18) | STSNLAS (SEQ ID NO: 5) | HQYHRSFPT (SEQ ID NO: 38) | |
| DM51 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 7.49 |
| | LC | TATSSVSSSYLH (SEQ ID NO: 18) | STSNLAS (SEQ ID NO: 5) | HQYHRSIPT (SEQ ID NO: 39) | |
| DM52 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 4.75 |
| | LC | TATSSVSSSYLH (SEQ ID NO: 18) | STSNLAS (SEQ ID NO: 5) | HQYHRSWPT (SEQ ID NO: 40) | |
| DM53 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 3.67 |
| | LC | TATSSVSSWYLH (SEQ ID NO: 22) | STSNLAS (SEQ ID NO: 5) | HQYHRSTPT (SEQ ID NO: 6) | |

TABLE 2 -continued

GHR antagonist antibodies and antigen-binding CDR sequences
according to Kabat (underlined) and Chothia (bold) with binding affinities ($K_D$)

| MAb | | CDR1 | CDR2 | CDR3 | $K_D$ (nM) |
|---|---|---|---|---|---|
| DM54 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 4.55 |
| | LC | TATSSVSSFYLH (SEQ ID NO: 23) | STSNLAS (SEQ ID NO: 5) | HQYHRSTPT (SEQ ID NO: 6) | |
| DM55 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 3.25 |
| | LC | TATSSVSSSYLD (SEQ ID NO: 24) | STSNLAS (SEQ ID NO: 5) | HQYHRSTPT (SEQ ID NO: 6) | |
| DM56 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 1.59 |
| | LC | TATSSVSSSYLN (SEQ ID NO: 4) | STSNLAS (SEQ ID NO: 5) | HQYHRSTPT (SEQ ID NO: 6) | |
| DM57 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 0.97 |
| | LC | TATSSVSSSYLH (SEQ ID NO: 18) | STSNLAS (SEQ ID NO: 5) | HQYHRFTPT (SEQ ID NO: 25) | |
| DM58 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 61.31 |
| | LC | TATSSVSSSYLH (SEQ ID NO: 18) | STSNLAS (SEQ ID NO: 5) | HQYHRRTPT (SEQ ID NO: 32) | |
| DM59 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 19.35 |
| | LC | TATSSVSSSYLH (SEQ ID NO: 18) | STSNLAS (SEQ ID NO: 5) | HQYHRYTPT (SEQ ID NO: 33) | |
| DM60 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 15.71 |
| | LC | TATSSVSSSYLH (SEQ ID NO: 18) | STSNLAS (SEQ ID NO: 5) | HQYHRHTPT (SEQ ID NO: 34) | |
| DM61 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 5.95 |
| | LC | TATSSVSSSYLH (SEQ ID NO: 18) | STSNLAS (SEQ ID NO: 5) | HQYHRQTPT (SEQ ID NO: 35) | |
| DM62 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 2.34 |
| | LC | TATSSVSSSYLH (SEQ ID NO: 18) | STSNLAS (SEQ ID NO: 5) | HQYHRGTPT (SEQ ID NO: 36) | |
| DM63 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 3.52 |
| | LC | TATSSVSSSYLH (SEQ ID NO: 18) | STSNLAS (SEQ ID NO: 5) | HQYHRSYPT (SEQ ID NO: 37) | |
| DM64 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 3.89 |
| | LC | TATSSVSSSYLH (SEQ ID NO: 18) | STSNLAS (SEQ ID NO: 5) | HQYHRSFPT (SEQ ID NO: 38) | |
| DM65 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 3.84 |
| | LC | TATSSVSSSYLH (SEQ ID NO: 18) | STSNLAS (SEQ ID NO: 5) | HQYHRSIPT (SEQ ID NO: 39) | |

TABLE 2 -continued

GHR antagonist antibodies and antigen-binding CDR sequences according to Kabat (underlined) and Chothia (bold) with binding affinities ($K_D$)

| MAb | | CDR1 | CDR2 | CDR3 | $K_D$ (nM) |
|---|---|---|---|---|---|
| DM66 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 2.89 |
| | LC | TATSSVSSSYLH (SEQ ID NO: 18) | STSNLAS (SEQ ID NO: 5) | HQYHRSWPT (SEQ ID NO: 40) | |
| DM67 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 2.37 |
| | LC | TATSSVSSWYLH (SEQ ID NO: 22) | STSNLAS (SEQ ID NO: 5) | HQYHRSTPT (SEQ ID NO: 6) | |
| DM68 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 2.20 |
| | LC | TATSSVSSFYLH (SEQ ID NO: 23) | STSNLAS (SEQ ID NO: 5) | HQYHRSTPT (SEQ ID NO: 6) | |
| DM69 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 1.12 |
| | LC | TATSSVSSSYLD (SEQ ID NO: 24) | STSNLAS (SEQ ID NO: 5) | HQYHRSTPT (SEQ ID NO: 6) | |
| DM70 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 1.13 |
| | LC | TATSSVSSSYLN (SEQ ID NO: 4) | STSNLAS (SEQ ID NO: 5) | HQYHRSTPT (SEQ ID NO: 6) | |
| DM71 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 5.08 |
| | LC | TATSSVSSSYLH (SEQ ID NO: 18) | STSNLAS (SEQ ID NO: 5) | HQYHRFTPT (SEQ ID NO: 25) | |
| DM72 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 16.35 |
| | LC | TATSSVSSSYLH (SEQ ID NO: 18) | STSNLAS (SEQ ID NO: 5) | HQYHRRTPT (SEQ ID NO: 32) | |
| DM73 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 31.93 |
| | LC | TATSSVSSSYLH (SEQ ID NO: 18) | STSNLAS (SEQ ID NO: 5) | HQYHRYTPT (SEQ ID NO: 33) | |
| DM74 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 3.72 |
| | LC | TATSSVSSSYLH (SEQ ID NO: 18) | STSNLAS (SEQ ID NO: 5) | HQYHRHTPT (SEQ ID NO: 34) | |
| DM75 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 7.49 |
| | LC | TATSSVSSSYLH (SEQ ID NO: 18) | STSNLAS (SEQ ID NO: 5) | HQYHRQTPT (SEQ ID NO: 35) | |
| DM76 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 4.42 |
| | LC | TATSSVSSSYLH (SEQ ID NO: 18) | STSNLAS (SEQ ID NO: 5) | HQYHRGTPT (SEQ ID NO: 36) | |
| DM77 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 3.10 |
| | LC | TATSSVSSSYLH (SEQ ID NO: 18) | STSNLAS (SEQ ID NO: 5) | HQYHRSYPT (SEQ ID NO: 37) | |

TABLE 2 -continued

GHR antagonist antibodies and antigen-binding CDR sequences
according to Kabat (underlined) and Chothia (bold) with binding affinities ($K_D$)

| MAb | | CDR1 | CDR2 | CDR3 | $K_D$ (nM) |
|---|---|---|---|---|---|
| DM78 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 4.25 |
| | LC | TATSSVSSSYLH (SEQ ID NO: 18) | STSNLAS (SEQ ID NO: 5) | HQYHRSFPT (SEQ ID NO: 38) | |
| DM79 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 2.80 |
| | LC | TATSSVSSSYLH (SEQ ID NO: 18) | STSNLAS (SEQ ID NO: 5) | HQYHRSIPT (SEQ ID NO: 39) | |
| DM80 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 2.89 |
| | LC | TATSSVSSSYLH (SEQ ID NO: 18) | STSNLAS (SEQ ID NO: 5) | HQYHRSWPT (SEQ ID NO: 40) | |
| DM81 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 2.50 |
| | LC | TATSSVSSWYLH (SEQ ID NO: 22) | STSNLAS (SEQ ID NO: 5) | HQYHRSTPT (SEQ ID NO: 6) | |
| DM82 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 1.54 |
| | LC | TATSSVSSFYLH (SEQ ID NO: 23) | STSNLAS (SEQ ID NO: 5) | HQYHRSTPT (SEQ ID NO: 6) | |
| DM83 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 0.59 |
| | LC | TATSSVSSSYLD (SEQ ID NO: 24) | STSNLAS (SEQ ID NO: 5) | HQYHRSTPT (SEQ ID NO: 6) | |
| DM84 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 1.13 |
| | LC | TATSSVSSSYLN (SEQ ID NO: 4) | STSNLAS (SEQ ID NO: 5) | HQYHRSTPT (SEQ ID NO: 6) | |
| L1M1 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 39.90 |
| | LC | RATSSVSSSYLH (SEQ ID NO: 41) | STSNLAS (SEQ ID NO: 5) | HQYHRSTPT (SEQ ID NO: 6) | |
| L1M2 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 40.40 |
| | LC | EATSSVSSSYLH (SEQ ID NO: 42) | STSNLAS (SEQ ID NO: 5) | HQYHRSTPT (SEQ ID NO: 6) | |
| L1P1 variants | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | |
| | LC | XATSSVSSSYLH, wherein X is T, R or E (SEQ ID NO: 146) | STSNLAS (SEQ ID NO: 5) | HQYHRSTPT (SEQ ID NO: 6) | |
| L1M3 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 26.80 |
| | LC | TPTSSVSSSYLH (SEQ ID NO: 43) | STSNLAS (SEQ ID NO: 5) | HQYHRSTPT (SEQ ID NO: 6) | |
| L1M4 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 38.50 |
| | LC | TASSSVSSSYLH (SEQ ID NO: 44) | STSNLAS (SEQ ID NO: 5) | HQYHRSTPT (SEQ ID NO: 6) | |

TABLE 2 -continued

GHR antagonist antibodies and antigen-binding CDR sequences
according to Kabat (underlined) and Chothia (bold) with binding affinities ($K_D$)

| MAb | | CDR1 | CDR2 | CDR3 | $K_D$ (nM) |
|---|---|---|---|---|---|
| L1M5 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 56.00 |
| | LC | TATTSVSSSYLH (SEQ ID NO: 45) | STSNLAS (SEQ ID NO: 5) | HQYHRSTPT (SEQ ID NO: 6) | |
| L1M6 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 48.70 |
| | LC | TATRSVSSSYLH (SEQ ID NO: 46) | STSNLAS (SEQ ID NO: 5) | HQYHRSTPT (SEQ ID NO: 6) | |
| L1M7 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 37.10 |
| | LC | TATWSVSSSYLH (SEQ ID NO: 47) | STSNLAS (SEQ ID NO: 5) | HQYHRSTPT (SEQ ID NO: 6) | |
| L1M8 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 51.10 |
| | LC | TATFSVSSSYLH (SEQ ID NO: 48) | STSNLAS (SEQ ID NO: 5) | HQYHRSTPT (SEQ ID NO: 6) | |
| L1P4 variants | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | |
| | LC | TATXSVSSSYLH wherein X is S, T, R, W or F (SEQ ID NO: 100) | STSNLAS (SEQ ID NO: 5) | HQYHRSTPT (SEQ ID NO: 6) | |
| L1M9 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 38.80 |
| | LC | TATSWVSSSYLH (SEQ ID NO: 49) | STSNLAS (SEQ ID NO: 5) | HQYHRSTPT (SEQ ID NO: 6) | |
| L1M10 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 48.30 |
| | LC | TATSVVSSSYLH (SEQ ID NO: 50) | STSNLAS (SEQ ID NO: 5) | HQYHRSTPT (SEQ ID NO: 6) | |
| L1M11 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 42.60 |
| | LC | TATSDVSSSYLH (SEQ ID NO: 51) | STSNLAS (SEQ ID NO: 5) | HQYHRSTPT (SEQ ID NO: 6) | |
| L1P5 variants | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | |
| | LC | TATSXVSSSYLH, wherein X is S, W, V or D (SEQ ID NO: 101) | STSNLAS (SEQ ID NO: 5) | HQYHRSTPT (SEQ ID NO: 6) | |
| L1M12 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 45.30 |
| | LC | TATSSVGSSYLH (SEQ ID NO: 52) | STSNLAS (SEQ ID NO: 5) | HQYHRSTPT (SEQ ID NO: 6) | |
| L1M13 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 38.80 |
| | LC | TATSSVWSSYLH (SEQ ID NO: 53) | STSNLAS (SEQ ID NO: 5) | HQYHRSTPT (SEQ ID NO: 6) | |

TABLE 2 -continued

GHR antagonist antibodies and antigen-binding CDR sequences
according to Kabat (underlined) and Chothia (bold) with binding affinities ($K_D$)

| MAb | | CDR1 | CDR2 | CDR3 | $K_D$ (nM) |
|---|---|---|---|---|---|
| L1P7 variants | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | |
| | LC | TATSSVXSSYLH, wherein X is S, G or W (SEQ ID NO: 102) | STSNLAS (SEQ ID NO: 5) | HQYHRSTPT (SEQ ID NO: 6) | |
| L1M14 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 43.90 |
| | LC | TATSSVSPSYLH (SEQ ID NO: 54) | STSNLAS (SEQ ID NO: 5) | HQYHRSTPT (SEQ ID NO: 6) | |
| L1M15 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 39.50 |
| | LC | TATSSVSQSYLH (SEQ ID NO: 55) | STSNLAS (SEQ ID NO: 5) | HQYHRSTPT (SEQ ID NO: 6) | |
| L1M16 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 43.00 |
| | LC | TATSSVSASYLH (SEQ ID NO: 56) | STSNLAS (SEQ ID NO: 5) | HQYHRSTPT (SEQ ID NO: 6) | |
| L1P8 variants | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | |
| | LC | TATSSVSXSYLH, wherein X is S, P or Q (SEQ ID NO: 103) | STSNLAS (SEQ ID NO: 5) | HQYHRSTPT (SEQ ID NO: 6) | |
| L1M17 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 31.30 |
| | LC | TATSSVSSGYLH (SEQ ID NO: 57) | STSNLAS (SEQ ID NO: 5) | HQYHRSTPT (SEQ ID NO: 6) | |
| L1M18 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 26.10 |
| | LC | TATSSVSSIYLH (SEQ ID NO: 58) | STSNLAS (SEQ ID NO: 5) | HQYHRSTPT (SEQ ID NO: 6) | |
| L1M19 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 29.40 |
| | LC | TATSSVSSEYLH (SEQ ID NO: 59) | STSNLAS (SEQ ID NO: 5) | HQYHRSTPT (SEQ ID NO: 6) | |
| L1M20 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 15.10 |
| | LC | TATSSVSSWYLH (SEQ ID NO: 22) | STSNLAS (SEQ ID NO: 5) | HQYHRSTPT (SEQ ID NO: 6) | |
| L1M21 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 15.20 |
| | LC | TATSSVSSFYLH (SEQ ID NO: 23) | STSNLAS (SEQ ID NO: 5) | HQYHRSTPT (SEQ ID NO: 6) | |
| L1P9 variants | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | |
| | LC | TATSSVSSXYLH, wherein X is S, G, I, E, W or F (SEQ ID NO: 104) | STSNLAS (SEQ ID NO: 5) | HQYHRSTPT (SEQ ID NO: 6) | |

TABLE 2 -continued

GHR antagonist antibodies and antigen-binding CDR sequences
according to Kabat (underlined) and Chothia (bold) with binding affinities ($K_D$)

| MAb | | CDR1 | CDR2 | CDR3 | $K_D$ (nM) |
|---|---|---|---|---|---|
| L1M22 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 52.40 |
| | LC | TATSSVSSSWLH (SEQ ID NO: 60) | STSNLAS (SEQ ID NO: 5) | HQYHRSTPT (SEQ ID NO: 6) | |
| L1M23 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 37.90 |
| | LC | TATSSVSSSYVH (SEQ ID NO: 61) | STSNLAS (SEQ ID NO: 5) | HQYHRSTPT (SEQ ID NO: 6) | |
| L1M24 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 37.20 |
| | LC | TATSSVSSSYFH (SEQ ID NO: 62) | STSNLAS (SEQ ID NO: 5) | HQYHRSTPT (SEQ ID NO: 6) | |
| L1P11 variants | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | |
| | LC | TATSSVSSSYXH, wherein X is L, V or F (SEQ ID NO: 105) | STSNLAS (SEQ ID NO: 5) | HQYHRSTPT (SEQ ID NO: 6) | |
| L1M25 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 5.90 |
| | LC | TATSSVSSSYLD (SEQ ID NO: 24) | STSNLAS (SEQ ID NO: 5) | HQYHRSTPT (SEQ ID NO: 6) | |
| L1M26 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 24.80 |
| | LC | TATSSVSSSYLP SEQ ID NO: 63) | STSNLAS (SEQ ID NO: 5) | HQYHRSTPT (SEQ ID NO: 6) | |
| L1M27 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 8.90 |
| | LC | TATSSVSSSYLN (SEQ ID NO: 4) | STSNLAS (SEQ ID NO: 5) | HQYHRSTPT (SEQ ID NO: 6) | |
| L1P12 variants | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | |
| | LC | TATSSVSSSYLX, wherein X is H, D, P, or N (SEQ ID NO: 99) | STSNLAS (SEQ ID NO: 5) | HQYHRSTPT (SEQ ID NO: 6) | |
| L3M1 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 19.20 |
| | LC | TATSSVSSSYLH (SEQ ID NO: 18) | STSNLAS (SEQ ID NO: 5) | HQYHRFTPT (SEQ ID NO: 25) | |
| L3M2 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 45.60 |
| | LC | TATSSVSSSYLH (SEQ ID NO: 18) | STSNLAS (SEQ ID NO: 5) | HQYHRRTPT (SEQ ID NO: 32) | |
| L3M3 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 41.60 |
| | LC | TATSSVSSSYLH (SEQ ID NO: 18) | STSNLAS (SEQ ID NO: 5) | HQYHRYTPT (SEQ ID NO: 33) | |

TABLE 2 -continued

GHR antagonist antibodies and antigen-binding CDR sequences
according to Kabat (underlined) and Chothia (bold) with binding affinities (K_D)

| MAb | | CDR1 | CDR2 | CDR3 | $K_D$ (nM) |
|---|---|---|---|---|---|
| L3M4 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 48.40 |
| | LC | TATSSVSSSYLH (SEQ ID NO: 18) | STSNLAS (SEQ ID NO: 5) | HQYHRHTPT (SEQ ID NO: 34) | |
| L3M5 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 71.10 |
| | LC | TATSSVSSSYLH (SEQ ID NO: 18) | STSNLAS (SEQ ID NO: 5) | HQYHRQTPT (SEQ ID NO: 35) | |
| L3M6 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 19.80 |
| | LC | TATSSVSSSYLH (SEQ ID NO: 18) | STSNLAS (SEQ ID NO: 5) | HQYHRGTPT (SEQ ID NO: 36) | |
| L3P6 variants | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | |
| | LC | TATSSVSSSYLH (SEQ ID NO: 18) | STSNLAS (SEQ ID NO: 5) | HQYHRXTPT wherein X is S, F, R, Y, H, Q or G (SEQ ID NO: 106) | |
| L3M7 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 29.90 |
| | LC | TATSSVSSSYLH (SEQ ID NO: 18) | STSNLAS (SEQ ID NO: 5) | HQYHRSYPT (SEQ ID NO: 37) | |
| L3M8 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 31.90 |
| | LC | TATSSVSSSYLH (SEQ ID NO: 18) | STSNLAS (SEQ ID NO: 5) | HQYHRSFPT (SEQ ID NO: 38) | |
| L3M9 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 28.20 |
| | LC | TATSSVSSSYLH (SEQ ID NO: 18) | STSNLAS (SEQ ID NO: 5) | HQYHRSIPT (SEQ ID NO: 39) | |
| L3M10 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 28.60 |
| | LC | TATSSVSSSYLH (SEQ ID NO: 18) | STSNLAS (SEQ ID NO: 5) | HQYHRSAPT (SEQ ID NO: 66) | |
| L3M11 | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | 34.80 |
| | LC | TATSSVSSSYLH (SEQ ID NO: 18) | STSNLAS (SEQ ID NO: 5) | HQYHRSWPT (SEQ ID NO: 40) | |
| L3P7 variants | HC | GFTFSDAWMD (SEQ ID NOs: 1 (whole), 15 and 16) | EIRSKANNHATYYAESVKG (SEQ ID NOs: 19 and 20) | YRDYW (SEQ ID NO: 21) | |
| | LC | TATSSVSSSYLH (SEQ ID NO: 18) | STSNLAS (SEQ ID NO: 5) | HQYHRSXPT wherein X is T, Y, F, I, A or W (SEQ ID NO: 107) | |
| H2M1 | HC | GFTFSDAWMD (SEQ ID NOs: 1 (whole), 15 and 16) | EIRAKANNHATYYAESVKG (SEQ ID NOs: 64 and 65) | YRDYW (SEQ ID NO: 21) | 10.10 |
| | LC | TATSSVSSSYLH (SEQ ID NO: 18) | STSNLAS (SEQ ID NO: 5) | HQYHRSTPT (SEQ ID NO: 6) | |

TABLE 2 -continued

GHR antagonist antibodies and antigen-binding CDR sequences
according to Kabat (underlined) and Chothia (bold) with binding affinities (K_D)

| MAb | | CDR1 | CDR2 | CDR3 | $K_D$ (nM) |
|---|---|---|---|---|---|
| H2M2 | HC | GFTFSDAWMD (SEQ ID NOs: 1 (whole), 15 and 16) | EIRTKANNHATYYAESVKG (SEQ ID NOs: 67 and 68) | YRDYW (SEQ ID NO: 21) | 11.20 |
| | LC | TATSSVSSSYLH (SEQ ID NO: 18) | STSNLAS (SEQ ID NO: 5) | HQYHRSTPT (SEQ ID NO: 6) | |
| H2P4 variants | HC | GFTFSDAWMD (SEQ ID NOs: 1 (whole), 15 and 16) | EIRXKANNHATYYAESVKG, wherein X is S, A or T (SEQ ID NOs: 108 and 109) | YRDYW (SEQ ID NO: 21) | |
| | LC | TATSSVSSSYLH (SEQ ID NO: 18) | STSNLAS (SEQ ID NO: 5) | HQYHRSTPT (SEQ ID NO: 6) | |
| H2M3 | HC | GFTFSDAWMD (SEQ ID NOs: 1 (whole), 15 and 16) | EIRSRANNHATYYAESVKG (SEQ ID NOs: 69 and 70) | YRDYW (SEQ ID NO: 21) | 40.40 |
| | LC | TATSSVSSSYLH (SEQ ID NO: 18) | STSNLAS (SEQ ID NO: 5) | HQYHRSTPT (SEQ ID NO: 6) | |
| H2M4 | HC | GFTFSDAWMD (SEQ ID NOs: 1 (whole), 15 and 16) | EIRSEANNHATYYAESVKG (SEQ ID NOs: 71 and 72) | YRDYW (SEQ ID NO: 21) | 13.10 |
| | LC | TATSSVSSSYLH (SEQ ID NO: 18) | STSNLAS (SEQ ID NO: 5) | HQYHRSTPT (SEQ ID NO: 6) | |
| H2P5 variants | HC | GFTFSDAWMD (SEQ ID NOs: 1 (whole), 15 and 16) | EIRSXANNHATYYAESVKG, wherein X is K, R or E (SEQ ID NOs: 110 and 111) | YRDYW (SEQ ID NO: 21) | |
| | LC | TATSSVSSSYLH (SEQ ID NO: 18) | STSNLAS (SEQ ID NO: 5) | HQYHRSTPT (SEQ ID NO: 6) | |
| H2M5 | HC | GFTFSDAWMD (SEQ ID NOs: 1 (whole), 15 and 16) | EIRSKDNNHATYYAESVKG (SEQ ID NOs: 73 and 74) | YRDYW (SEQ ID NO: 21) | 11.60 |
| | LC | TATSSVSSSYLH (SEQ ID NO: 18) | STSNLAS (SEQ ID NO: 5) | HQYHRSTPT (SEQ ID NO: 6) | |
| H2M6 | HC | GFTFSDAWMD (SEQ ID NOs: 1 (whole), 15 and 16) | EIRSKSNNHATYYAESVKG (SEQ ID NOs: 75 and 76) | YRDYW (SEQ ID NO: 21) | 15.00 |
| | LC | TATSSVSSSYLH (SEQ ID NO: 18) | STSNLAS (SEQ ID NO: 5) | HQYHRSTPT (SEQ ID NO: 6) | |
| H2M7 | HC | GFTFSDAWMD (SEQ ID NOs: 1 (whole), 15 and 16) | EIRSKVNNHATYYAESVKG (SEQ ID NOs: 77 and 78) | YRDYW (SEQ ID NO: 21) | 12.70 |
| | LC | TATSSVSSSYLH (SEQ ID NO: 18) | STSNLAS (SEQ ID NO: 5) | HQYHRSTPT (SEQ ID NO: 6) | |
| H2M8 | HC | GFTFSDAWMD (SEQ ID NOs: 1 (whole), 15 and 16) | EIRSKYNNHATYYAESVKG (SEQ ID NOs: 79 and 80) | YRDYW (SEQ ID NO: 21) | 12.90 |
| | LC | TATSSVSSSYLH (SEQ ID NO: 18) | STSNLAS (SEQ ID NO: 5) | HQYHRSTPT (SEQ ID NO: 6) | |
| H2M9 | HC | GFTFSDAWMD (SEQ ID NOs: 1 (whole), 15 and 16) | EIRSKENNHATYYAESVKG (SEQ ID NOs: 81 and 82) | YRDYW (SEQ ID NO: 21) | 12.00 |
| | LC | TATSSVSSSYLH (SEQ ID NO: 18) | STSNLAS (SEQ ID NO: 5) | HQYHRSTPT (SEQ ID NO: 6) | |
| H2P6 variants | HC | GFTFSDAWMD (SEQ ID NOs: 1 (whole), 15 and 16) | EIRSKXNNHATYYAESVKG, wherein X is A, D, S, V, Y or E (SEQ ID NOs: 112 and 113) | YRDYW (SEQ ID NO: 21) | |
| | LC | TATSSVSSSYLH (SEQ ID NO: 18) | STSNLAS (SEQ ID NO: 5) | HQYHRSTPT (SEQ ID NO: 6) | |
| H2M10 | HC | GFTFSDAWMD (SEQ ID NOs: 1 (whole), 15 and 16) | EIRSKANFHATYYAESVKG (SEQ ID NOs: 26 and 27) | YRDYW (SEQ ID NO: 21) | 12.10 |
| | LC | TATSSVSSSYLH (SEQ ID NO: 18) | STSNLAS (SEQ ID NO: 5) | HQYHRSTPT (SEQ ID NO: 6) | |

TABLE 2 -continued

GHR antagonist antibodies and antigen-binding CDR sequences
according to Kabat (underlined) and Chothia (bold) with binding affinities ($K_D$)

| MAb | | CDR1 | CDR2 | CDR3 | $K_D$ (nM) |
|---|---|---|---|---|---|
| H2M11 | HC | GFTFSDAWMD (SEQ ID NOs: 1 (whole), 15 and 16) | EIRSKANWHATYYAESVKG (SEQ ID NOs: 83 and 84) | YRDYW (SEQ ID NO: 21) | 14.20 |
| | LC | TATSSVSSSYLH (SEQ ID NO: 18) | STSNLAS (SEQ ID NO: 5) | HQYHRSTPT (SEQ ID NO: 6) | |
| H2M12 | HC | GFTFSDAWMD (SEQ ID NOs: 1 (whole), 15 and 16) | EIRSKANIHATYYAESVKG (SEQ ID NOs: 85 and 86) | YRDYW (SEQ ID NO: 21) | 11.80 |
| | LC | TATSSVSSSYLH (SEQ ID NO: 18) | STSNLAS (SEQ ID NO: 5) | HQYHRSTPT (SEQ ID NO: 6) | |
| H2M13 | HC | GFTFSDAWMD (SEQ ID NOs: 1 (whole), 15 and 16) | EIRSKANDHATYYAESVKG (SEQ ID NOs: 87 and 88) | YRDYW (SEQ ID NO: 21) | 55.00 |
| | LC | TATSSVSSSYLH (SEQ ID NO: 18) | STSNLAS (SEQ ID NO: 5) | HQYHRSTPT (SEQ ID NO: 6) | |
| H2M14 | HC | GFTFSDAWMD (SEQ ID NOs: 1 (whole), 15 and 16) | EIRSKANYHATYYAESVKG (SEQ ID NOs: 17 and 2) | YRDYW (SEQ ID NO: 21) | 6.00 |
| | LC | TATSSVSSSYLH (SEQ ID NO: 18) | STSNLAS (SEQ ID NO: 5) | HQYHRSTPT (SEQ ID NO: 6) | |
| H2M15 | HC | GFTFSDAWMD (SEQ ID NOs: 1 (whole), 15 and 16) | EIRSKANKHATYYAESVKG (SEQ ID NOs: 89 and 90) | YRDYW (SEQ ID NO: 21) | 12.50 |
| | LC | TATSSVSSSYLH (SEQ ID NO: 18) | STSNLAS (SEQ ID NO: 5) | HQYHRSTPT (SEQ ID NO: 6) | |
| H2M16 | HC | GFTFSDAWMD (SEQ ID NOs: 1 (whole), 15 and 16) | EIRSKANRHATYYAESVKG (SEQ ID NOs: 91 and 92) | YRDYW (SEQ ID NO: 21) | 8.8 |
| | LC | TATSSVSSSYLH (SEQ ID NO: 18) | STSNLAS (SEQ ID NO: 5) | HQYHRSTPT (SEQ ID NO: 6) | |
| H2P8 variants | HC | GFTFSDAWMD (SEQ ID NOs: 1 (whole), 15 and 16) | EIRSKANXHATYYAESVKG, wherein X is N, F, W, I, D, Y, K or R (SEQ ID NOs: 114 and 115) | YRDYW (SEQ ID NO: 21) | |
| | LC | TATSSVSSSYLH (SEQ ID NO: 18) | STSNLAS (SEQ ID NO: 5) | HQYHRSTPT (SEQ ID NO: 6) | |
| H2M17 | HC | GFTFSDAWMD (SEQ ID NOs: 1 (whole), 15 and 16) | EIRSKANNWATYYAESVKG (SEQ ID NOs: 93 and 94) | YRDYW (SEQ ID NO: 21) | 7.50 |
| | LC | TATSSVSSSYLH (SEQ ID NO: 18) | STSNLAS (SEQ ID NO: 5) | HQYHRSTPT (SEQ ID NO: 6) | |
| H2M18 | HC | GFTFSDAWMD (SEQ ID NOs: 1 (whole), 15 and 16) | EIRSKANNIATYYAESVKG (SEQ ID NOs: 95 and 96) | YRDYW (SEQ ID NO: 21) | 9.30 |
| | LC | TATSSVSSSYLH (SEQ ID NO: 18) | STSNLAS (SEQ ID NO: 5) | HQYHRSTPT (SEQ ID NO: 6) | |
| H2M19 | HC | GFTFSDAWMD (SEQ ID NOs: 1 (whole), 15 and 16) | EIRSKANNYATYYAESVKG (SEQ ID NOs: 97 and 98) | YRDYW (SEQ ID NO: 21) | 7.20 |
| | LC | TATSSVSSSYLH (SEQ ID NO: 18) | STSNLAS (SEQ ID NO: 5) | HQYHRSTPT (SEQ ID NO: 6) | |
| H2M20 | HC | GFTFSDAWMD (SEQ ID NOs: 1 (whole), 15 and 16) | EIRSKANNFATYYAESVKG (SEQ ID NOs: 28 and 29) | YRDYW (SEQ ID NO: 21) | 8.0 |
| | LC | TATSSVSSSYLH (SEQ ID NO: 18) | STSNLAS (SEQ ID NO: 5) | HQYHRSTPT (SEQ ID NO: 6) | |
| H2P9 variants | HC | GFTFSDAWMD (SEQ ID NOs: 1 (whole), 15 and 16) | EIRSKANNXATYYAESVKG, wherein X is H, W, I, Y or F (SEQ ID NOs: 116 and 117) | YRDYW (SEQ ID NO: 21) | |
| | LC | TATSSVSSSYLH (SEQ ID NO: 18) | STSNLAS (SEQ ID NO: 5) | HQYHRSTPT (SEQ ID NO: 6) | |

TABLE 2 -continued

GHR antagonist antibodies and antigen-binding CDR sequences
according to Kabat (underlined) and Chothia (bold) with binding affinities ($K_D$)

| MAb | | CDR1 | CDR2 | CDR3 | $K_D$ (nM) |
|---|---|---|---|---|---|
| H3M1 | HC | GFTFSDA<u>WMD</u> (SEQ ID NOs: 1 (whole), 15 and 16) | <u>EIRSKANNHA</u>TYYAESVKG (SEQ ID NOs: 19 and 20) | I<u>YRDYW</u> (SEQ ID NO: 3 (whole) and 21) | 328.60 |
| | LC | <u>TATSSVSSSYLH</u> (SEQ ID NO: 18) | <u>STSNLAS</u> (SEQ ID NO: 5) | <u>HQYHRSTPT</u> (SEQ ID NO: 6) | |
| H3M2 | HC | GFTFSDA<u>WMD</u> (SEQ ID NOs: 1 (whole), 15 and 16) | <u>EIRSKANNHA</u>TYYAESVKG (SEQ ID NOs: 19 and 20) | TLF<u>RDYW</u> (SEQ ID NO: 3) | 26.80 |
| | LC | <u>TATSSVSSSYLH</u> (SEQ ID NO: 18) | <u>STSNLAS</u> (SEQ ID NO: 5) | <u>HQYHRSTPT</u> (SEQ ID NO: 6) | |
| H3M3 | HC | GFTFSDA<u>WMD</u> (SEQ ID NOs: 1 (whole), 15 and 16) | <u>EIRSKANNHA</u>TYYAESVKG (SEQ ID NOs: 19 and 20) | I<u>RDYW</u> (SEQ ID NO: 3) | 9.40 |
| | LC | <u>TATSSVSSSYLH</u> (SEQ ID NO: 18) | <u>STSNLAS</u> (SEQ ID NO: 5) | <u>HQYHRSTPT</u> (SEQ ID NO: 6) | |
| H3P1 variants | HC | GFTFSDA<u>WMD</u> (SEQ ID NOs: 1 (whole), 15 and 16) | <u>EIRSKANNHA</u>TYYAESVKG (SEQ ID NOs: 19 and 20) | X<u>RDYW</u>, wherein X is Y, F or I (SEQ ID NO: 118) | |
| | LC | <u>TATSSVSSSYLH</u> (SEQ ID NO: 18) | <u>STSNLAS</u> (SEQ ID NO: 5) | <u>HQYHRSTPT</u> (SEQ ID NO: 6) | |
| H3VZ variant | HC | GFTFSDA<u>WMD</u> (SEQ ID NOs: 1 (whole), 15 and 16) | <u>EIRSKANNHA</u>TYYAESVKG (SEQ ID NOs: 19 and 20) | X<u>YRDYW</u>, wherein X is L or I (SEQ ID NO: 119 (whole) and 21) | |
| | LC | <u>TATSSVSSSYLH</u> (SEQ ID NO: 18) | <u>STSNLAS</u> (SEQ ID NO: 5) | <u>HQYHRSTPT</u> (SEQ ID NO: 6) | |
| DM1 variants | HC | GFTFSDA<u>WMD</u> (SEQ ID NOs: 1 (whole), 15 and 16) | <u>EIRSKANNHA</u>TYYAESVKG (SEQ ID NOs: 19 and 20) | X<u>YRDYW</u>, wherein X is L or I (SEQ ID NO: 119 (whole) and 21) | |
| | LC | <u>TATSSVSSSYLH</u> (SEQ ID NO: 18) | <u>STSNLAS</u> (SEQ ID NO: 5) | <u>HQYHRXTPT</u>, wherein X is S, F, R, Y, H, Q or G (SEQ ID NO: 106) | |
| DM2 variants | HC | GFTFSDA<u>WMD</u> (SEQ ID NOs: 1 (whole), 15 and 16) | <u>EIRSKANNHA</u>TYYAESVKG (SEQ ID NOs: 19 and 20) | X<u>YRDYW</u>, wherein X is L or I (SEQ ID NO: 119 (whole) and 21) | |
| | LC | <u>TATSSVSSSYLH</u> (SEQ ID NO: 18) | <u>STSNLAS</u> (SEQ ID NO: 5) | <u>HQYHRSXPT</u>, wherein X is T, Y, F, I or W (SEQ ID NO: 122) | |
| DM3 variants | HC | GFTFSDA<u>WMD</u> (SEQ ID NOs: 1 (whole), 15 and 16) | <u>EIRSKANNHA</u>TYYAESVKG (SEQ ID NOs: 19 and 20) | X<u>YRDYW</u>, wherein X is L or I (SEQ ID NO: 119 (whole) and 21) | |
| | LC | <u>TATSSVSSXYLH</u>, wherein X is S, W or F (SEQ ID NO: 120) | <u>STSNLAS</u> (SEQ ID NO: 5) | <u>HQYHRSTPT</u> (SEQ ID NO: 6) | |
| DM4 variants | HC | GFTFSDA<u>WMD</u> (SEQ ID NOs: 1 (whole), 15 and 16) | <u>EIRSKANNHA</u>TYYAESVKG (SEQ ID NOs: 19 and 20) | X<u>YRDYW</u>, wherein X is L or I (SEQ ID NO: 119 (whole) and 21) | |
| | LC | <u>TATSSVSSSYLX</u>, wherein X is H, D or N (SEQ ID NO: 121) | <u>STSNLAS</u> (SEQ ID NO: 5) | <u>HQYHRSTPT</u> (SEQ ID NO: 6) | |

TABLE 2 -continued

GHR antagonist antibodies andantigen-binding CDR sequences according to Kabat (underlined) and Chothia (bold) with binding affinities ($K_D$)

| MAb | | CDR1 | CDR2 | CDR3 | $K_D$ (nM) |
|---|---|---|---|---|---|
| DM5 variants | HC | GFTFSDAWMD (SEQ ID NOs: 1 (whole), 15 and 16) | EIRSKANNHATYYAESVKG (SEQ ID NOs: 19 and 20) | XRDYW, wherein X is Y, F or I (SEQ ID NO: 118) | |
| | LC | TATSSVSSSYLH (SEQ ID NO: 18) | STSNLAS (SEQ ID NO: 5) | HQYHRXTPT, wherein X is S, F, R, Y, H, Q or G (SEQ ID NO: 106) | |
| DM6 variants | HC | GFTFSDAWMD (SEQ ID NOs: 1 (whole), 15 and 16) | EIRSKANNHATYYAESVKG (SEQ ID NOs: 19 and 20) | XRDYW, wherein X is Y, F or I (SEQ ID NO: 118) | |
| | LC | TATSSVSSSYLH (SEQ ID NO: 18) | STSNLAS (SEQ ID NO: 5) | HQYHRSXPT, wherein X is T, Y, F, I or W (SEQ ID NO: 122) | |
| DM7 variants | HC | GFTFSDAWMD (SEQ ID NOs: 1 (whole), 15 and 16) | EIRSKANNHATYYAESVKG (SEQ ID NOs: 19 and 20) | XRDYW, wherein X is Y, F or I (SEQ ID NO: 118) | |
| | LC | TATSSVSSXYLH, wherein X is S, W or F (SEQ ID NO: 120) | STSNLAS (SEQ ID NO: 5) | HQYHRSTPT (SEQ ID NO: 6) | |
| DM8 variants | HC | GFTFSDAWMD (SEQ ID NOs: 1 (whole), 15 and 16) | EIRSKANNHATYYAESVKG (SEQ ID NOs: 19 and 20) | XRDYW, wherein X is Y, F or I (SEQ ID NO: 118) | |
| | LC | TATSSVSSSYLX, wherein X is H, D or N (SEQ ID NO: 121) | STSNLAS (SEQ ID NO: 5) | HQYHRSTPT (SEQ ID NO: 6) | |
| DM9 variants | HC | GFTFSDAWMD (SEQ ID NOs: 1 (whole), 15 and 16) | EIRSKANXHATYYAESVKG, wherein X is N, F or Y (SEQ ID NOs: 123 and 124) | YRDYW (SEQ ID NO: 21) | |
| | LC | TATSSVSSSYLH (SEQ ID NO: 18) | STSNLAS (SEQ ID NO: 5) | HQYHRXTPT, wherein X is S, F, R, Y, H, Q or G (SEQ ID NO: 106) | |
| DM10 variants | HC | GFTFSDAWMD (SEQ ID NOs: 1 (whole), 15 and 16) | EIRSKANXHATYYAESVKG, wherein X is N, F or Y (SEQ ID NOs: 123 and 124) | YRDYW (SEQ ID NO: 21) | |
| | LC | TATSSVSSSYLH (SEQ ID NO: 18) | STSNLAS (SEQ ID NO: 5) | HQYHRSXPT wherein X is T, Y, F, I or W (SEQ ID NO: 122) | |
| DM11 variants | HC | GFTFSDAWMD (SEQ ID NOs: 1 (whole), 15 and 16) | EIRSKANXHATYYAESVKG, wherein X is N, F or Y (SEQ ID NOs: 123 and 124) | YRDYW (SEQ ID NO: 21) | |
| | LC | TATSSVSSXYLH, wherein X is S, W or F (SEQ ID NO: 120) | STSNLAS (SEQ ID NO: 5) | HQYHRSTPT (SEQ ID NO: 6) | |
| DM12 variants | HC | GFTFSDAWMD (SEQ ID NOs: 1 (whole), 15 and 16) | EIRSKANXHATYYAESVKG, wherein X is N, F or Y (SEQ ID NOs: 123 and 124) | YRDYW (SEQ ID NO: 21) | |
| | LC | TATSSVSSSYLX, wherein X is H, D or N (SEQ ID NO: 121) | STSNLAS (SEQ ID NO: 5) | HQYHRSTPT (SEQ ID NO: 6) | |

TABLE 2 -continued

GHR antagonist antibodies and antigen-binding CDR sequences
according to Kabat (underlined) and Chothia (bold) with binding affinities (K$_D$)

| MAb | | CDR1 | CDR2 | CDR3 | K$_D$ (nM) |
|---|---|---|---|---|---|
| DM13 variants | HC | GFTFSDAWMD (SEQ ID NOs: 1 (whole), 15 and 16) | EIRSKANNXATYYAESVKG, wherein X is H or F (SEQ ID NOs: 125 and 126) | YRDYW (SEQ ID NO: 21) | |
| | LC | TATSSVSSSYLH (SEQ ID NO: 18) | STSNLAS (SEQ ID NO: 5) | HQYHRXTPT, wherein X is S, F, R, Y, H, Q or G (SEQ ID NO: 106) | |
| DM14 variants | HC | GFTFSDAWMD (SEQ ID NOs: 1 (whole), 15 and 16) | EIRSKANNXATYYAESVKG, wherein X is H or F (SEQ ID NOs: 125 and 126) | YRDYW (SEQ ID NO: 21) | |
| | LC | TATSSVSSSYLH (SEQ ID NO: 18) | STSNLAS (SEQ ID NO: 5) | HQYHRSXPT, wherein X is T, Y, F, I or W (SEQ ID NO: 122) | |
| DM15 variants | HC | GFTFSDAWMD (SEQ ID NOs: 1 (whole), 15 and 16) | EIRSKANNXATYYAESVKG, wherein X is H or F (SEQ ID NOs: 125 and 126) | YRDYW (SEQ ID NO: 21) | |
| | LC | TATSSVSSXYLH, wherein X is S, W or F (SEQ ID NO: 120) | STSNLAS (SEQ ID NO: 5) | HQYHRSTPT (SEQ ID NO: 6) | |
| DM16 variants | HC | GFTFSDAWMD (SEQ ID NOs: 1 (whole), 15 and 16) | EIRSKANNXATYYAESVKG, wherein X is H or F (SEQ ID NOs: 125 and 126) | YRDYW (SEQ ID NO: 21) | |
| | LC | TATSVSSSYLX, wherein X is H, D or N (SEQ ID NO: 121) | STSNLAS (SEQ ID NO: 5) | HQYHRSTPT (SEQ ID NO: 6) | |
| TM1 variants | HC | GFTFSDAWMD (SEQ ID NOs: 1 (whole), 15 and 16) | EIRSKANXHATYYAESVKG, wherein X is N or Y (SEQ ID NOs: 127 and 128) | XRDYW, wherein X is Y or I (SEQ ID NO: 129) | |
| | LC | TATSSVSSSYLH (SEQ ID NO: 18) | STSNLAS (SEQ ID NO: 5) | HQYHRXTPT, wherein X is S, F, R, Y, H or G (SEQ ID NO: 130) | |
| TM2 variants | HC | GFTFSDAWMD (SEQ ID NOs: 1 (whole), 15 and 16) | EIRSKANXHATYYAESVKG, wherein X is N or Y (SEQ ID NOs: 127 and 128) | XRDYW, wherein X is Y or I (SEQ ID NO: 129) | |
| | LC | TATSSVSSSYLH (SEQ ID NO: 18) | STSNLAS (SEQ ID NO: 5) | HQYHRSXPT, wherein X is T, Y, F, I or W (SEQ ID NO: 122) | |
| TM3 variants | HC | GFTFSDAWMD (SEQ ID NOs: 1 (whole), 15 and 16) | EIRSKANXHATYYAESVKG, wherein X is N or Y (SEQ ID NOs: 127 and 128) | XRDYW, wherein X is Y or I (SEQ ID NO: 129) | |
| | LC | TATSSVSSXYLH, wherein X is S, W or F (SEQ ID NO: 120) | STSNLAS (SEQ ID NO: 5) | HQYHRSTPT (SEQ ID NO: 6) | |
| TM4 variants | HC | GFTFSDAWMD (SEQ ID NOs: 1 (whole), 15 and 16) | EIRSKANXHATYYAESVKG, wherein X is N or Y (SEQ ID NOs: 127 and 128) | XRDYW, wherein X is Y or I (SEQ ID NO: 129) | |
| | LC | TATSSVSSSYLX, wherein X is H, D or N (SEQ ID NO: 121) | STSNLAS (SEQ ID NO: 5) | HQYHRSTPT (SEQ ID NO: 6) | |
| TM5 variants | HC | GFTFSDAWMD (SEQ ID NOs: 1 (whole), 15 and 16) | EIRSKANXHATYYAESVKG, wherein X is N, F or Y (SEQ ID NOs: 123 and 124) | YRDYW (SEQ ID NO: 21) | |
| | LC | TATSSVSSSYLX, wherein X is H or D (SEQ ID NO: 131) | STSNLAS (SEQ ID NO: 5) | HQYHRXTPT, wherein X is S or F (SEQ ID NO: 132) | |

TABLE 2 -continued

GHR antagonist antibodies andantigen-binding CDR sequences
according to Kabat (underlined) and Chothia (bold) with binding affinities (K$_D$)

| MAb | | CDR1 | CDR2 | CDR3 | K$_D$ (nM) |
|---|---|---|---|---|---|
| TM6 variants | HC | GFTF<u>SDAWMD</u> (SEQ ID NOs: 1 (whole), 15 and 16) | <u>EIRSKANNXATYYAESVKG</u>, wherein X is H or F (SEQ ID NOs: 125 and 126) | YRDYW (SEQ ID NO: 21) | |
| | LC | <u>TATSSVSSSYLX</u>, wherein X is H or D (SEQ ID NO: 131) | <u>STSNLAS</u> (SEQ ID NO: 5) | HQYHRXTPT wherein X is S or F (SEQ ID NO: 132) | |
| TM7 variants | HC | GFTF<u>SDAWMD</u> (SEQ ID NOs: 1 (whole), 15 and 16) | <u>EIRSKANNHATYYAESVKG</u> (SEQ ID NOs: 19 and 20) | XRDYW, wherein X is Y, F or I (SEQ ID NO: 118) | |
| | LC | <u>TATSSVSSSYLX</u>, wherein X is H or D (SEQ ID NO: 131) | <u>STSNLAS</u> (SEQ ID NO: 5) | HQYHRXTPT wherein X is S or F (SEQ ID NO: 132) | |
| TM8 variants | HC | GFTF<u>SDAWMD</u> (SEQ ID NOs: 1 (whole), 15 and 16) | <u>EIRSKANNHATYYAESVKG</u> (SEQ ID NOs: 19 and 20) | XYRDYW, wherein X is L or I (SEQ ID NO: 119 (whole) and 21) | |
| TM9 variants | LC | <u>TATSSVSSSYLX</u>, wherein X is H or D (SEQ ID NO: 131) | <u>STSNLAS</u> (SEQ ID NO: 5) | HQYHRXTPT wherein X is S or F (SEQ ID NO: 132) | |
| QM1 variants | HC | GFTF<u>SDAWMD</u> (SEQ ID NOs: 1 (whole), 15 and 16) | <u>EIRSKANXHATYYAESVKG</u>, wherein X is N, F, W, I, D, Y, K or R (SEQ ID NOs: 114 and 115) | XRDYW, wherein X is Y, F or I (SEQ ID NO: 118) | |
| | LC | <u>TATSSVSSSYLX</u>, wherein X is H, D, P, or N (SEQ ID NO: 99) | <u>STSNLAS</u> (SEQ ID NO: 5) | HQYHRXTPT, wherein X is S, F, R, Y, H, Q or G (SEQ ID NO: 106) | |
| QM2 variants | HC | GFTF<u>SDAWMD</u> (SEQ ID NOs: 1 (whole), 15 and 16) | <u>EIRSKANXHATYYAESVKG</u>, wherein X is N, F, W, I, D, Y, K or R (SEQ ID NOs: 114 and 115) | XRDYW, wherein X is Y, F or I (SEQ ID NO: 118) | |
| | LC | <u>TATSSVSSSYLX</u>, wherein X is H, D, P, or N (SEQ ID NO: 99) | <u>STSNLAS</u> (SEQ ID NO: 5) | HQYHRSXPT, wherein X is T, Y, F, I, A or W (SEQ ID NO: 107) | |

The invention also provides methods of making any of these antibodies or polypeptides. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In some embodiments, antibodies may be prepared and selected by phage display technology. See, for example, U.S. Pat. Nos. 5,565,332; 5,580,717; 5,733,743; and 6,265,150; and Winter et al., Annu. Rev. Immunol. 12:433-455, 1994. Alternatively, the phage display technology (McCafferty et al., Nature 348:552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597, 1991, or Griffith et al., EMBO J. 12:725-734, 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783, 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

In some embodiments, antibodies may be made using hybridoma technology. It is contemplated that any mammalian subject including humans or antibody producing cells therefrom can be manipulated to serve as the basis for production of mammalian, including human, hybridoma cell lines. The route and schedule of immunization of the host animal are generally in keeping with established and conventional techniques for antibody stimulation and production, as further described herein. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., 1975, Nature 256:495-497 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the GHR monoclonal antibodies of the subject invention. The hybridomas or other immortalized B-cells are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for GHR, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a GHR polypeptide, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

If desired, the GHR antagonist antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329, 112; U.S. Pat. No. 7,314,622.

In some embodiments, the polynucleotide sequence may be used for genetic manipulation to "humanize" the antibody or to improve the affinity, or other characteristics of the antibody. Antibodies may also be customized for use, for example, in dogs, cats, primate, equines and bovines.

In some embodiments, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., domain, single chain, etc. are known in the art.

Immunoassays and flow cytometry sorting techniques such as fluorescence activated cell sorting (FACS) can also be employed to isolate antibodies that are specific for GHR.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of a GHR monoclonal antibody herein.

Antibody fragments can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In some embodiments, a polynucleotide comprises a sequence encoding the heavy chain and/or the light chain variable regions of antibody SS1, SS3, SS4, TM1 or TM9. The sequence encoding the antibody of interest may be maintained in a vector in a host cell and the host cell can then be expanded and frozen for future use. Vectors (including expression vectors) and host cells are further described herein.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using, for example, Biacore™ surface plasmon resonance analysis, which detects differences in binding affinity of about 2-fold or greater, Kinexa® Biosensor, scintillation proximity assays, ELISA, ORIGEN® immunoassay, fluorescence quenching, fluorescence transfer, and/or yeast display. Binding affinity may also be screened using a suitable bioassay. Biacore™ is particularly useful when the starting antibody already binds with a relatively high affinity, for example a $K_D$ of about 10 nM or lower.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., 1993, Gene 137(1):109-18.

The CDR may be heavy chain variable region (VH) CDR3 and/or light chain variable region (VL) CDR3. The CDR may be one or more of VH CDR1, VH CDR2, VH CDR3, VL CDR1, VL CDR2, and/or VL CDR3. The CDR may be a Kabat CDR, a Chothia CDR, an extended CDR, an AbM CDR, a contact CDR, or a conformational CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore™ surface plasmon resonance analysis, and selection using any method known in the art for selection, including phage display, yeast display, and ribosome display.

To express the GHR antibodies of the present invention, DNA fragments encoding VH and VL regions can first be obtained using any of the methods described above. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

The invention encompasses modifications to the variable regions shown in Table 1 and the CDRs shown in Table 2. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to GHR. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 3 under the heading of "conservative substitutions." If such substitutions result in a change in biological activity, then more substantial changes, denominated "exemplary substitutions" in Table 3, or as further described below in reference to amino acid classes, may be introduced and the products screened.

TABLE 3

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:
 (1) Non-polar: Norleucine, Met, Ala, Val, Leu, Ile;
 (2) Polar without charge: Cys, Ser, Thr, Asn, Gln;
 (3) Acidic (negatively charged): Asp, Glu;
 (4) Basic (positively charged): Lys, Arg;
 (5) Residues that influence chain orientation: Gly, Pro; and
 (6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The antibodies may also be modified, e.g. in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the antibody for GHR, to increase or decrease $k_{off}$, or to alter the binding specificity of the antibody. Techniques in site-directed mutagenesis are well-known in the art. See, e.g., Sambrook et al. and Ausubel et al., supra.

A modification or mutation may also be made in a framework region or constant region to increase the half-life of a GHR antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments, the antibody comprises a modified constant region that has increased or decreased binding affinity to a human Fc gamma receptor, is immunologically inert or partially inert, e.g., does not trigger complement mediated lysis, does not stimulate antibody-dependent cell mediated cytotoxicity (ADCC), or does not activate microglia; or has reduced activities (compared to the unmodified antibody) in any one or more of the following: triggering complement mediated lysis, stimulating ADCC, or activating microglia. Different modifications of the constant region may be used to achieve optimal level and/or combination of effector functions. See, for example, Morgan et al., Immunology 86:319-324, 1995; Lund et al., J. Immunology 157:4963-9 157:4963-4969, 1996; Idusogie et al., J. Immunology 164:4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 1999, 29:2613-2624; PCT Application No. PCT/GB99/01441; and/or UK Patent Application No. 9809951.8.

In some embodiments, an antibody constant region can be modified to avoid interaction with Fc gamma receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, e.g., U.S. Pat. Nos. 5,997,867 and 5,866,692.

In some embodiments, the constant region is modified as described in Eur. J. Immunol., 1999, 29:2613-2624; PCT Application No. PCT/GB99/01441; and/or UK Patent Application No. 9809951.8. In such embodiments, the Fc can be human IgG$_2$ or human IgG$_4$. The Fc can be human IgG$_2$ containing the mutation A330P331 to S330S331 (IgG$_{2\Delta a}$), in which the amino acid residues are numbered with reference to the wild type IgG$_2$ sequence. Eur. J. Immunol., 1999, 29:2613-2624. In some embodiments, the antibody comprises a constant region of IgG$_4$ comprising the following mutations (Armour et al., 2003, Molecular Immunology 40 585-593): E233F234L235 to P233V234A235 (IgG$_{4\Delta c}$), in which the numbering is with reference to wild type IgG4. In yet another embodiment, the Fc is human IgG$_4$ E233F234L235 to P233V234A235 with deletion G236 (IgG$_{4\Delta b}$). In another embodiment the Fc is any human IgG$_4$ Fc (IgG$_4$, IgG$_{4\Delta b}$ or IgG$_{4\Delta c}$) containing hinge stabilizing mutation S228 to P228 (Aalberse et al., 2002, Immunology 105, 9-19).

In some embodiments, the antibody comprises a human heavy chain IgG$_2$ constant region comprising the following mutations: A330P331 to S330S331 (amino acid numbering with reference to the wild type IgG$_2$ sequence). Eur. J. Immunol., 1999, 29:2613-2624. In still other embodiments, the constant region is aglycosylated for N-linked glycosylation. In some embodiments, the constant region is aglycosylated for N-linked glycosylation by mutating the oligosaccharide attachment residue and/or flanking residues that are part of the N-glycosylation recognition sequence in the constant region. For example, N-glycosylation site N297 may be mutated to, e.g., A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

In some embodiments, the antibody comprises a modified constant region that has increased binding affinity for FcRn and/or an increased serum half-life as compared with the unmodified antibody.

In a process known as "germlining", certain amino acids in the VH and VL sequences can be mutated to match those found naturally in germline VH and VL sequences. In particular, the amino acid sequences of the framework regions in the VH and VL sequences can be mutated to match the germline sequences to reduce the risk of immunogenicity when the antibody is administered. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., 1992, J. Mol. Biol. 227:776-798; and Cox et al., 1994, Eur. J. Immunol. 24:827-836).

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of a GHR antibody of the invention can be cleaved. In various embodiments of the invention, the heavy and light chains of the GHR antibodies may optionally include a signal sequence.

Once DNA fragments encoding the VH and VL segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG$_1$, IgG$_2$, IgG$_3$, IgG$_4$, IgA, IgE, IgM or IgD constant region, but most preferably is an IgG$_1$ or IgG$_2$ constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the VH-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH- and VL-encoding DNA fragments are operatively linked to another fragment encoding a flexible linker such that the VH and VL sequences can be expressed as a contiguous single-chain protein, with the VL and VH regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. An example of a linking peptide is (GGGGS)$_3$ (SEQ ID NO: 144), which bridges approximately 3.5 nm between the carboxy terminus of one variable region and the amino terminus of the other variable region. Linkers of other sequences have been designed and used (Bird et al., 1988, supra). Linkers can in turn be modified for additional functions, such as attachment of drugs or attachment to solid supports. The single chain antibody may be monovalent, if only a single VH and VL are used, bivalent, if two VH and VL are used, or polyvalent, if more than two VH and VL are used. Bispecific or polyvalent antibodies may be generated that bind specifically to GHR and to another molecule. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as $E.$ $coli$. Polynucleotides encoding the scFv of interest can be made by routine manipulations such as ligation of polynucleotides. The resultant scFv can be isolated using standard protein purification techniques known in the art.

Other forms of single chain antibodies, such as diabodies, are also encompassed. Diabodies are bivalent, bispecific antibodies in which VH and VL are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad Sci. USA 90:6444-6448; Poljak, R. J., et al., 1994, Structure 2:1121-1123).

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

The invention also encompasses fusion proteins comprising one or more fragments or regions from the antibodies disclosed herein. In some embodiments, a fusion antibody may be made that comprises all or a portion of a GHR antibody of the invention linked to another polypeptide. In another embodiment, only the variable domains of the GHR antibody are linked to the polypeptide. In another embodiment, the VH domain of a GHR antibody is linked to a first polypeptide, while the VL domain of a GHR antibody is linked to a second polypeptide that associates with the first polypeptide in a manner such that the VH and VL domains can interact with one another to form an antigen binding site. In another preferred embodiment, the VH domain is separated from the VL domain by a linker such that the VH and VL domains can interact with one another. The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In some embodiments, a fusion polypeptide is provided that comprises at least 10 contiguous amino acids of the variable light chain region shown in SEQ ID NOs: 7, 9, 11, 13 or 14 and/or at least 10 amino acids of the variable heavy chain region shown in SEQ ID NOs: 8, 10 or 12. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises a light chain variable region and/or a heavy chain variable region, as shown in any of the sequence pairs selected from among SEQ ID NOs: 7 and 8, 9 and 10, 11 and 12, 13 and 8, and 14 and 8. In another embodiment, the fusion polypeptide comprises one or more CDR(s). In still other embodiments, the fusion polypeptide comprises VH CDR3 and/or VL CDR3. For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

A fusion polypeptide can be created by methods known in the art, for example, synthetically or recombinantly. Typically, the fusion proteins of this invention are made by preparing an expressing a polynucleotide encoding them using recombinant methods described herein, although they may also be prepared by other means known in the art, including, for example, chemical synthesis.

In other embodiments, other modified antibodies may be prepared using GHR antibody encoding nucleic acid molecules. For instance, "Kappa bodies" (Ill et al., 1997, Protein Eng. 10:949-57), "Minibodies" (Martin et al., 1994, EMBO J. 13:5303-9), "Diabodies" (Holliger et al., supra), or "Janusins" (Traunecker et al., 1991, EMBO J. 10:3655-3659 and Traunecker et al., 1992, Int. J. Cancer (Suppl.) 7:51-52) may be prepared using standard molecular biological techniques following the teachings of the specification.

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121: 210). For example, bispecific antibodies or antigen-binding fragments can be produced by fusion of hybridomas or linking of Fab' fragments. See, e.g., Songsivilai & Lachmann, 1990, Clin. Exp. Immunol. 79:315-321, Kostelny et al., 1992, J. Immunol. 148:1547-1553. Traditionally, the recombinant production of bispecific antibodies was based on the coexpression of two immunoglobulin heavy chain-light chain pairs, with the two heavy chains having different specificities (Millstein and Cuello, 1983, Nature 305, 537-539). In addition, bispecific antibodies may be formed as "diabodies" or "Janusins." In some embodiments, the bispecific antibody binds to two different epitopes of GHR. In some embodiments, the modified antibodies described above are prepared using one or more of the variable domains or CDR regions from a GHR antibody provided herein.

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

This invention also provides compositions comprising antibodies conjugated (for example, linked) to an agent that facilitate coupling to a solid support (such as biotin or avidin). For simplicity, reference will be made generally to antibodies with the understanding that these methods apply to any of the GHR binding and/or antagonist embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

An antibody or polypeptide of this invention may be linked to a labeling agent such as a fluorescent molecule, a radioactive molecule or any others labels known in the art. Labels are known in the art which generally provide (either directly or indirectly) a signal.

Polynucleotides, Vectors, and Host Cells

The invention also provides polynucleotides encoding any of the antibodies, including antibody fragments and modified antibodies described herein, such as, e.g., antibodies having impaired effector function. In another aspect, the invention provides a method of making any of the polynucleotides described herein. Polynucleotides can be made and expressed by procedures known in the art. Accordingly, the invention provides polynucleotides or compositions, including pharmaceutical compositions, comprising polynucleotides, encoding any of the following: the antibodies SS1, SS3, SS4, TM1 or TM9 or any fragment or part thereof having the ability to antagonize GHR.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a fragment thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a fragment thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors are further provided. Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to GHR or a GHR domain is effected by an immunoassay or FACS. A cell overexpressing the antibody or protein of interest can be identified.

An expression vector can be used to direct expression of a GHR antagonist antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266: 338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 1994, 14:2411, and in Woffendin, Proc. Natl. Acad. Sci., 1994, 91:1581.

Compositions

The invention also provides pharmaceutical compositions comprising an effective amount of a GHR antibody described herein. Examples of such compositions, as well as how to formulate, are also described herein. In some embodiments, the composition comprises one or more GHR antibodies. In other embodiments, the GHR antibody recognizes GHR. In other embodiments, the GHR antibody is a human antibody. In other embodiments, the GHR antibody is a humanized antibody. In some embodiments, the GHR antibody comprises a constant region that is capable of triggering a desired immune response, such as antibody-mediated lysis or ADCC. In other embodiments, the GHR antibody comprises a constant region that does not trigger an unwanted or undesirable immune response, such as antibody-mediated lysis or ADCC. In other embodiments, the GHR antibody comprises one or more CDR(s) of the antibody (such as one, two, three, four, five, or, in some embodiments, all six CDRs).

It is understood that the compositions can comprise more than one GHR antagonist antibody (e.g., a mixture of GHR antagonist antibodies that recognize different epitopes of GHR). Other exemplary compositions comprise more than one GHR antagonist antibodies that recognize the same epitope(s), or different species of GHR antagonist antibodies that bind to different epitopes of GHR.

The composition used in the present invention can further comprise pharmaceutically acceptable carriers, excipients, or stabilizers (Remington: The Science and practice of Pharmacy 20th Ed. (2000) Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The GHR antagonist antibody and compositions thereof can also be used in conjunction with other agents that serve to enhance and/or complement the effectiveness of the agents.

The invention also provides compositions, including pharmaceutical compositions, comprising any of the polynucleotides of the invention. In some embodiments, the composition comprises an expression vector comprising a polynucleotide encoding the antibody as described herein. In other embodiment, the composition comprises an expression vector comprising a polynucleotide encoding any of the antibodies described herein. In still other embodiments, the composition comprises either or both of the polynucleotides shown in SEQ ID NO: 142 and SEQ ID NO: 143 below. The nucleic acid sequences encoding the heavy and light chain of SS1 hIgG$_{2\Delta a}$ GHR antagonist antibody is shown below:

SS1 hIgG$_{2\Delta a}$ heavy chain:
(SEQ ID NO: 142)
GAGGTGCAGCTGGTGGAATCTGGCGGCGGACTGGTGAAACCTGGCGG

CAGCCTGAGACTGAGCTGCGCCGCCAGCGGCTTCACCTTCAGCGACG

CCTGGATGGACTGGGTGCGCCAGGCCCCTGGCAAGGGACTGGAATGG

GTGGCCGAGATCAGAAGCAAGGCCAACTATCACGCCACCTACTACGC

CGAGAGCGTGAAGGGCCGGTTCACCATCAGCCGGGACGACAGCAAGA

ACACCCTGTACCTGCAGATGAACAGCCTGAAAACCGAGGACACCGCC

GTGTACTACTGCACCCTGATTAGAGACTACTGGGGCCAGGGCACCCT

GGTCACCGTCTCCTCAGCCTCCACCAAGGGCCCATCGGTCTTCCCCC

TGGCGCCCTGCTCCAGGAGCACCTCCGAGAGCACAGCGGCCCTGGGC

TGCCTGGTCAAGGACTACTTCCCCGAACCGGTGACGGTGTCGTGGAA

CTCAGGCGCTCTGACCAGCGGCGTGCACACCTTCCCGGCTGTCCTAC

AGTCCTCAGGACTCTACTCCCTCAGCAGCGTAGTGACCGTGCCCTCC

AGCAACTTCGGCACCCAGACCTACACCTGCAACGTAGATCACAAGCC

CAGCAACACCAAGGTGGACAAGACAGTTGAGCGCAAATGTTGTGTCG

AGTGCCCACCGTGCCCAGCACCACCTGTGGCAGGACCGTCAGTCTTC

CTCTTCCCCCCAAAACCCAAGGACACCCTCATGATCTCCCGGACCCC

TGAGGTCACGTGCGTGGTGGTGGACGTGAGCCACGAAGACCCCGAGG

TCCAGTTCAACTGGTACGTGGACGGCGTGGAGGTGCATAATGCCAAG

ACAAAGCCACGGGAGGAGCAGTTCAACAGCACGTTCCGTGTGGTCAG

CGTCCTCACCGTCGTGCACCAGGACTGGCTGAACGGCAAGGAGTACA

AGTGCAAGGTCTCCAACAAAGGCCTCCCATCCTCCATCGAGAAAACC

ATCTCCAAAACCAAAGGGCAGCCCCGAGAACCACAGGTGTACACCCT

GCCCCCATCCCGGGAGGAGATGACCAAGAACCAGGTCAGCCTGACCT

GCCTGGTCAAAGGCTTCTACCCCAGCGACATCGCCGTGGAGTGGGAG

AGCAATGGGCAGCCGGAGAACAACTACAAGACCACACCTCCCATGCT

GGACTCCGACGGCTCCTTCTTCCTCTACAGCAAGCTCACCGTGGACA

-continued
AGAGCAGGTGGCAGCAGGGGAACGTCTTCTCATGCTCCGTGATGCAT

GAGGCTCTGCACAACCACTACACACAGAAGAGCCTCTCCCTGTCTCC

GGGTAAA

SS1 hIgG$_{2\Delta a}$ light chain:
(SEQ ID NO: 143)
GAGATCGTGCTGACCCAGAGCCCCGGCACCCTGTCTCTGAGCCCTGG

CGAGAGAGCCACCCTGAGCTGTACCGCCACCAGCAGCGTGTCCAGCA

GCTACCTGAATTGGTATCAGCAGAAGCCCGGCCAGGCCCCCAGACTG

CTGATCTACAGCACCAGCAACCTGGCCAGCGGCATCCCCGACAGATT

CAGCGGCAGCGGCTCCGGCACCGACTTCACCCTGACCATCAGCCGGC

TGGAACCCGAGGACTTCGCCGTGTACTACTGCCACCAGTACCACAGA

AGCACCCCCACCTTCGGCGGAGGCACCAAGGTGGAGATCAAACGAAC

TGTGGCTGCACCATCTGTCTTCATCTTCCCGCCATCTGATGAGCAGT

TGAAATCTGGAACTGCCTCTGTTGTGTGCCTGCTGAATAACTTCTAT

CCCAGAGAGGCCAAAGTACAGTGGAAGGTGGATAACGCCCTCCAATC

GGGTAACTCCCAGGAGAGTGTCACAGAGCAGGACAGCAAGGACAGCA

CCTACAGCCTCAGCAGCACCCTGACGCTGAGCAAAGCAGACTACGAG

AAACACAAAGTCTACGCCTGCGAAGTCACCCATCAGGGCCTGAGCTC

GCCCGTCACAAAGAGCTTCAACAGGGGAGAGTGT

Kits

The invention also provides kits comprising any or all of the antibodies described herein. Kits of the invention include one or more containers comprising a GHR antagonist antibody described herein and instructions for use in accordance with any of the methods of the invention described herein. Generally, these instructions comprise a description of administration of the GHR antagonist for the above described therapeutic treatments. In some embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In some embodiments, the antibody is a human antibody. In some embodiments, the antibody is a humanized antibody. In some embodiments, the antibody is a monoclonal antibody. The instructions relating to the use of a GHR antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a GHR antibody. The container may further comprise a second pharmaceutically active agent.

Kits may optionally provide additional components such as buffers and interpretive information. Normally, the kit comprises a container and a label or package insert(s) on or associated with the container.

Biological Deposit

Representative materials of the present invention were deposited in the American Type Culture Collection, 10801 University Boulevard, Manassas, Va. 20110-2209, USA, on Dec. 22, 2011. Vector SS1-HC having ATCC Accession No. PTA-12352 is a polynucleotide encoding the SS1 heavy chain variable region, and vector SS1-LC having ATCC Accession No. PTA-12353 is a polynucleotide encoding the SS1 light chain variable region. The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1

Generating and Screening GHR Antagonist Antibodies

General Procedures for Immunization of Animals for Generating Monoclonal Antibodies:

Balb/c mice were injected 4 times on days 0, 3, 6 and 9 with 25 µg antigen hGHR/Fc R&D Systems™ Cat No. 1210-GR-050. For the first 4 injections, antigen was prepared by mixing the recombinant proteins with Gerbu adjuvant following the protocol and vortexing. Immunogen was given via injection to the scruff of the neck, the foot pads and intraperitoneally. The last boost, on day 11, was administered i.v., without adjuvant. On day 15, the mice were euthanized and their spleens were removed. Lymphocytes were immortalized by fusion with an established cell line to make hybridoma clones using standard hybridoma technology and distributed into 96 well plates. Clones were allowed to grow, and then were selected by ELISA screening using the immunizing antigen as described below.

ELISA Screening of Antibodies:

Supernatant media from growing hybridoma clones were screened separately for their ability to bind the recombinant human GHR/hFc. The assay was performed with 96-well plates coated overnight with 50 µl of a 1 µg/ml solution of the antigen. Excess reagents were washed from the wells between each step with PBS containing 0.05% Tween™-20. Supernatant was added to the plates and incubated at room temperature for 2 hours. Horse radish peroxidase (HRP) conjugated goat-anti mouse Fc was added to bind to the mouse antibodies bound to the antigen. ABTS (2 2'-Azino-bis(3-ethylbenzothiazoline-6-Suffonic acid) diammonium salt) was then added as substrate for HRP to detect the amount of mouse antibody present in the supernatant. The relative amount of antibody was quantified by reading the absorbance at 405 nm. Hybridoma clones that secreted antibodies that are capable of binding to human GHR/hFc were selected. The next assay was run to detect antibodies to hFc so that they could be avoided. Further analysis was carried out to characterize the selected clones.

Example 2

Determining Antibody Kinetics and Binding Affinity

This Example illustrates the determination of antibody kinetics and binding affinities of GHR antibodies to human and cyno GHR.

Determination of Kinetics and Affinity of GHR/Ab13 IgG Interactions at 25° C.

The affinity of a mouse anti-GHR antibody, Ab13, to human and cyno GHR was measured on a Biacore™ 2000 biosensor (GE Lifesciences™, Piscataway N.J.). An anti-mouse Ig sensor surface was prepared using a Biacore™ CM5 chip and reagents from the Biacore™ mouse antibody capture kit (GE Lifesciences™, Catalog# BR-1008-38), using instructions provided by the manufacturer.

The kinetics assay was run using a kinetic titration methodology as described in Karlsson et al., 2006, Anal. Biochem 349, 136-147. The mouse antibody, Ab13, was captured onto downstream flow cells at 0.5 µg/mL at a flow rate of 5 µL/min for 1 minute, 2 minutes and 4 minutes on flow cells 2, 3 and 4 respectively. Flow cell 1 was used as a reference surface. Following capture of antibodies, either human or cyno GHR (his-tagged monomers of amino acids 31-235 of the extracellular domain of the human or cyno GHR) was injected at 30 µL/minute on all flow cells in a series of injections from low to high concentration. The top concentration was 400 nM for human GHR and 2000 nM for cyno GHR; the dilution factor was 5-fold. Each GHR injection was two-minutes, the dissociation time after the 400 nM PCSK9 injection was 10 minutes. A similar set of injections was performed with running buffer in place of GHR for double-referencing purposes (double-referencing as described in Myszka, 1999, J. Mol. Recognit 12, 279-284). Each GHR dilution series was run in duplicate. After each analysis cycle all flow cells were regenerated with one three minute injection of 10 mM glycine pH 1.7. The double-referenced sensorgrams were fit globally to a simple 1:1 Langmuir with mass transport binding model (with a local $R_{max}$ parameter for each flow cell).

The experiments were performed at 25° C. using a running buffer of 10 mM HEPES, 150 mM NaCl, 0.05% (v/v) Tween-20TH, pH 7.4. The results of the study are summarized in Table 4a below.

Determination of Kinetics and Affinity of GHR/IgG Interactions for SS1 and Ab13-hFc Chimera at 25° C.

The affinities of a humanized GHR antibody, SS1, and a chimeric molecule comprising the Fab of Ab13 fused to a human Fc domain ("Ab13-hFc") to human and cyno GHR was measured on a Biacore™ 2000 biosensor (GE Lifesciences™ Piscataway N.J.).

An anti-human Fc sensor chip was prepared by activating all flow cells of a Biacore™ CM4 sensor chip with a 1:1 (v/v) mixture of 400 mM ethyl-N-(3-diethylaminopropyl)carbodiimide (EDC, Biacore™) and 100 mM N-hydroxysuccinimide (NHS, Biacore™) for 7 minutes, at a flow rate of 10 µL/min. An anti-human Fc reagent (goat F(ab')$_2$ fragment anti-human IgG Fc, Cappel Catalog #55053) was diluted to 60 µg/mL in 10 mM sodium acetate pH 5.0 and injected on all flow cells for 7 minutes at 20 µL/min. All flow cells were blocked with 100 mM ethylenediamine in 150 mM borate buffer pH 8.5 for 7 minutes at 10 µL/min.

The kinetics assay was run using a methodology with varying dissociation times as described in Katsamba et al., 2006, Anal. Biochem 352, 208-221. Antibodies were captured onto downstream flow cells (flow cells 2, 3 and 4) at 4 µg/mL at a flow rate of 10 µL/min for 1 minute. Different antibodies were captured on each flow cell. Flow cell 1 was used as a reference surface. Following capture of antibodies, analyte (buffer, human GHR or cyno GHR) was injected at 30 µL/min on all flow cells for two minutes. For the GHR analytes, his-tagged monomers of amino acids 31-235 of the extracellular domain of the human or cyno GHR were used. After the analyte injection, dissociation was monitored for 30 minutes (for the 400 nM GHR cycle) or 30 seconds (all other cycles) followed by regeneration of all flow cells with two 30-second injections of 75 mM phosphoric acid. A 5-membered dilution series of GHR was analyzed using this method, where the top concentration was 400 nM and the dilution factor was 3-fold. Buffer cycles were collected with both 30 minute and 30 second dissociation times for double-referencing purposes. The double-referenced sensorgrams were fit globally to a simple 1:1 Langmuir with mass transport binding model.

The experiments were performed at 25° C. using a running buffer of 10 mM HEPES, 150 mM NaCl, 0.05% (v/v) Tween-20™, pH 7.4. The results of the study are summarized in Table 4a below.

Determination of Kinetics and Affinity of GHR/Fab Interactions (with Immobilized Fab) at 37° C.

The affinity of GHR antibody SS1 Fab to human and cyno GHR was measured on a Biacore™ T200 biosensor (GE Lifesciences™, Piscataway N.J.).

An anti-human kappa sensor chip was prepared by activating all flow cells of a Biacore™ CM4 sensor chip with a 1:1 (v/v) mixture of 400 mM EDC and 100 mM NHS for 7 minutes, at a flow rate of 10 µL/min. An anti-human kappa reagent (goat F(ab')$_2$ fragment anti-human kappa, Southern Biotech Catalog #2063-01) was diluted to 50 µg/mL in 10 mM sodium acetate pH 4.5 and injected on all flow cells for 7 minutes at 20 µL/min. All flow cells were blocked with 100 mM ethylenediamine in 150 mM borate buffer pH 8.5 for 7 minutes at 10 µL/min.

The kinetics assay was run using a methodology with varying dissociation times as described in Katsamba et al., supra. Fabs were captured onto downstream flow cells (flow cells 2, 3 and 4) at 2 µg/mL at a flow rate of 10 µL/min for 2 minutes. Different Fabs were captured on each flow cell. Flow cell 1 was used as a reference surface. Following capture of fabs, analyte (buffer, human GHR or cyno GHR) was injected at 30 µL/min on all flow cells for two minutes. For the GHR analytes, his-tagged monomers of amino acids 31-235 of the extracellular domain of the human or cyno GHR were used. After the analyte injection, dissociation was monitored for 30 minutes (for the 133 nM and 400 nM GHR cycles) or 60 seconds (all other cycles) followed by regeneration with three 30-second injections of 10 mM glycine pH 1.7. A 6-membered dilution series of GHR was analyzed using this method, where the top concentration was 400 nM and the dilution factor was 3-fold. Buffer cycles were collected with both 30 minute and 60 second dissociation times for double-referencing purposes. The double-referenced sensorgrams were fit globally to a simple 1:1 Langmuir with mass transport binding model.

The experiments were performed at 37° C. using a running buffer of 10 mM HEPES, 150 mM NaCl, 0.05% (v/v) Tween-20™, pH 7.4. The results of the study are summarized in Table 4b below.

Determination of Kinetics and Affinity of GHR/Fab Interactions (where hGHR-hFc is Immobilized) at 37° C.

The affinity of GHR antibody SS1 Fab to human and cyno GHR was measured on a Biacore™ T200 biosensor (GE Lifesciences™, Piscataway N.J.).

An anti-human Fc sensor chip was prepared by activating all flow cells of a Biacore™ CM4 sensor chip with a 1:1 (v/v) mixture of 400 mM EDC and 100 mM NHS for 7 minutes, at a flow rate of 10 µL/min. An anti-human Fc reagent (goat F(ab')$_2$ fragment to human IgG Fc, Cappel Catalog #55053)

TABLE 4a

| | Analyte | | | | | | | |
|---|---|---|---|---|---|---|---|---|
| | Human GHR | | | | Cyno GHR | | | |
| Immobilized | ka (1/Ms) | kd (1/s) | t ½ (min) | $K_D$ (nM) | ka (1/Ms) | kd (1/s) | t ½ (min) | $K_D$ (nM) |
| Ab13[1] | 4.2E+04 | 6.0E−04 | 19 | 14.3 | 1.4E+04 | 8.4E−04 | 13.8 | 58.7 |
| Ab13-hFc[2] | 1.2E+05 | 6.9E−04 | 17 | 5.8 | 1.1E+05 | 2.0E−03 | 5.9 | 18.2 |
| SS1[2] | 7.4E+04 | 7.7E−05 | 150 | 1.0 | 8.1E+04 | 1.0E−04 | 111.1 | 1.3 |
| SS1 (replicate)[2] | 7.7E+04 | 6.4E−05 | 180 | 0.8 | 8.9E+04 | 1.1E−04 | 107.0 | 1.2 |

[1]Antibody immobilized by capture on an anti-mouse Ig surface
[2]Antibody immobilized by capture on an anti-human Fc surface was diluted to 60 µg/mL in 10 mM sodium acetate pH 5.0 and injected on all flow cells for 7 minutes at 20 µL/min. All flow cells were blocked with 100 mM ethylenediamine in 150 mM borate buffer pH 8.5 for 7 minutes at 10 µL/min.

The kinetics assay was run using a methodology with varying dissociation times as described in Katsamba et al., supra. The hGHR-hFc fusion protein (R&D Systems™ Catalog#1210-GR) was captured onto downstream flow cells at 2 µg/mL at a flow rate of 10 µL/min for 30 seconds, 1 minute and 2 minutes on flow cells 2, 3 and 4, respectively. Flow cell 1 was used as a reference surface. Following capture of hGHR-hFc, analyte (buffer, SS1 Fab or Ab13 Fab) was injected at 30 µL/min on all flow cells for two minutes. After the analyte injection, dissociation was monitored for 30 minutes (400 nM Fab cycle) or 60 seconds (all other cycles) followed by regeneration with two 30-second injections of 75 mM phosphoric acid. A 5-membered dilution series of Fab was analyzed using this method, where the top concentration was 400 nM and the dilution factor was 3-fold. Buffer cycles were collected at both 30 minute and 60 second dissociation times for double-referencing purposes. The double-referenced sensorgrams were fit globally to a simple 1:1 Langmuir with mass transport binding model (with a local Rmax parameter for each flow cell).

The experiments were performed at 37° C. using a running buffer of 10 mM HEPES, 150 mM NaCl, 0.05% (v/v) Tween-20™, pH 7.4. The results of the study are summarized in Table 4b below.

TABLE 4b

| Immobilized | Analyte | ka (1/Ms) | kd (1/s) | t ½ (min) | $K_D$ (nM) |
|---|---|---|---|---|---|
| SS1 Fab[1] | human GHR | 1.38E+05 | 2.15E-04 | 53.7 | 1.6 |
| SS1 Fab[1] | cyno GHR | 1.82E+05 | 5.76E-04 | 20.0 | 3.2 |
| hGHR-hFc[2] | SS1 Fab | 3.74E+05 | 3.59E-04 | 32.2 | 1.0 |
| hGHR-hFc[2] | Ab13 Fab | 1.47E+05 | 4.25E-03 | 2.7 | 28.8 |

[1]Fab immobilized by capture on an anti-human kappa surface
[2]hGHR-hFc immobilized by capture on an anti-human Fc surface Example 3

STAT5 Phosphorylation In Vitro Assay

This Example illustrates the effect of GHR antibodies in an in vitro STAT5 phosphorylation assay. In this Example, the ability of GHR antibodies to block GHR downstream signaling was tested in vitro using human GHR overexpressing cells and cyno GHR overexpressing cells.

GH signals through the JAK/STAT pathway. Binding of GH to GHR causes a conformational change in the dimerized receptor. This change results in the intracellular phosphorylation of JAK2 (Janus-associated kinase 2). Phosphorylation of JAK2 then induces the phosphorylation of STAT5 (signal transducer and activator of transcription 5). Phosphorylated STAT5 translocates to the nucleus, where it binds to the promoter sequences of GH-dependent genes.

GHR antagonist antibody Ab13 was tested for its ability to block STAT5 in an in vitro assay. HEK293 cells were transiently transfected with either DNA encoding full-length human GHR (SEQ ID NO: 140) or DNA encoding full-length cyno GHR (SEQ ID NO: 141). Cells were cultured in freestyle media for approximately 60 hours before testing. Cells were washed with DPBS (Dulbecco's Phosphate-Buffered Saline) and resuspended in Freestyle media, then counted using a hemocytometer. 1×10[6] cells were seeded per well in 6-well plates in 2 mls of Freestyle media. Cells were incubated for 2 hours at 37° C., then treated with 5, 50, or 500 nM Ab13 antibody in media. Cells were incubated at 37° C. with gentle mixing for 5 min with antibodies. 4.5 nM GH (Genotropin) was then added to all but control wells. Cells were incubated with GH at 37° C. with gentle mixing for 10 minutes.

Following incubation with GH, 2 ml of ice cold DPBS with 1× protease inhibitor cocktail (Roche) and 1 mM sodium orthovanadate (BioLabs) were added to each well and the plates were placed on ice. Cells were transferred to 5 ml tubes and spun down to create a cell pellet and the wash buffer was aspirated, leaving the cell pellet.

Reagents from Millipore™ MILLIPLEX® MAP Cell Signaling Buffer and Detection Kit (cat. #48-602) were used to lyse and treat the cell pellets. Millipore lysis buffer with 1× protease inhibitor cocktail and 1 mM sodium orthovanadate was added to each pellet at a volume of 200 ul/pellet. Cells were vortexed and incubated for 15 minutes at room temp with occasional vortexing. Millipore Assay buffer 2 with 1× protease inhibitor cocktail and 1 mM sodium orthovanadate was then added to the lysates at 300 ul/well.

Millipore™ MILLIPLEX® MAP Phospho STAT5N8 (Tyr694/699) MAPmate™ beads (Cat. #46-641) were resuspended in Assay Buffer 2 (from Millipore™ kit cat. #48-602) and loaded on a 96-well filter plate (provided in kit) at 25 ul/well, 25 ul/well of sample lysate was added to the wells and the beads and samples were incubated overnight at 4'C with shaking in the dark.

The liquid was then aspirated using a vacuum manifold and the remaining beads were washed using Millipore™ kit wash buffer. 25 ul Millipore™ kit detection antibody was added and incubated for 1 hour at room temperature with shaking in the dark. The detection antibody was vacuumed through and 25 ul kit streptavidin—Phycoerythrin was added and incubated in the dark for 15 min with shaking. 25 ul kit amplification buffer was then added and incubated for 15 min with shaking in the dark. The liquid was aspirated using a vacuum manifold, and the beads were resuspended in 150 ul kit assay buffer 2 and mixed on a shaker for 5 minutes before reading the plate.

The plate was read using a Luminex™ 200 instrument and fluorescent signal emitted from the samples was measured, The results of the STAT5 assay are shown in Tables 5 and 6. "Ave" indicates the average fluorescent signal, and "SEM" indicates the standard error of the mean.

TABLE 5

STAT5 Assay Using Human GHR-transfected cells

| Row | Treatment | fluorescent signal |
|---|---|---|
| 1 | no GH | 21 |
| 2 | 4.5 nM GH | 519 |
| 3 | 5 nM Ab13 + 4.5 nM GH | 225 |
| 4 | 50 nM Ab13 plus 4.5 nM GH | 26 |
| 5 | 500 nM Ab13 plus 4.5 nM GH | 28 |

TABLE 6

STAT5 Assay Using Cyno GHR-transfected cells

| | | fluorescent signal | |
|---|---|---|---|
| Row | Treatment | Ave | SEM |
| 1 | no GH | 22 | 12 |
| 2 | 4.5 nM GH | 562 | 29 |

TABLE 6-continued

STAT5 Assay Using Cyno GHR-transfected cells

| Row | Treatment | fluorescent signal Ave | SEM |
|---|---|---|---|
| 3 | 5 nM Ab13 + 4.5 nM GH | 317 | 33 |
| 4 | 50 nM Ab13 plus 4.5 nM GH | 51 | 4 |

Treatment of GHR-transfected cells with 4.5 nM OH stimulated STAT5 signaling in cells expressing either human GHR (Table 5, row 2) or cyno GHR (Table 6, row 2). Ab13 blocked STAT5 signaling in a dose-dependent manner (Table 5, rows 3-5; Table 6, rows 3 and 4).

Ab13 was affinity matured and humanized, leading to the selection of antibodies SS3 and SS1. The heavy and light chain amino acid sequences of the humanized GHR antagonist antibodies SS1 and SS3 are shown below.

SS1 hIgG2Δa heavy chain acid sequence
(SEQ ID NO: 134)
EVQLVESGGGLVKPGGSLRLSCAASGFTFSDAWMDWVRQAPGKGLEW
VAEIRSKANYHATYYAESVKGRFTISRDDSKNTLYLQMNSLKTEDTA
VYYCTLIRDYWGQGTLVTVSSASTKGPSVFPLAPCSRSTSESTAALG
CLVKDYFPEPVTVSWNSGALTSGVHTFPAVLQSSGLYSLSSVVTVPS
SNFGTQTYTCNVDHKPSNTKVDKTVERKCCVECPPCPAPPVAGPSVF
LFPPKPKDTLMISRTPEVTCVVVDVSHEDPEVQFNWYVDGVEVHNAK
TKPREEQFNSTFRVVSVLTVVHQDWLNGKEYKCKVSNKGLPSSIEKT
ISKTKGQPREPQVYTLPPSREEMTKNQVSLTCLVKGFYPSDIAVEWE
SNGQPENNYKTTPPMLDSDGSFFLYSKLTVDKSRWQQGNVFSCSVMH
EALHNHYTQKSLSLSPGK SS1 hIgG2Δa heavy chain amino acid sequence
without C-terminal lysine
(SEQ ID NO: 133)
EVQLVESGGGLVKPGGSLRLSCAASGFTFSDAWMDWVRQAPGKGLEW
VAEIRSKANYHATYYAESVKGRFTISRDDSKNTLYLQMNSLKTEDTA
VYYCTLIRDYWGQGTLVTVSSASTKGPSVFPLAPCSRSTSESTAALG
CLVKDYFPEPVTVSWNSGALTSGVHTFPAVLQSSGLYSLSSVVTVPS
SNFGTQTYTCNVDHKPSNTKVDKTVERKCCVECPPCPAPPVAGPSVF
LFPPKPKDTLMISRTPEVTCVVVDVSHEDPEVQFNWYVDGVEVHNAK
TKPREEQFNSTFRVVSVLTVVHQDWLNGKEYKCKVSNKGLPSSIEKT
ISKTKGQPREPQVYTLPPSREEMTKNQVSLTCLVKGFYPSDIAVEWE
SNGQPENNYKTTPPMLDSDGSFFLYSKLTVDKSRWQQGNVFSCSVMH
EALHNHYTQKSLSLSPG SS1 hIgG2Δa light chain amino acid sequence
(SEQ ID NO: 135)
EIVLTQSPGTLSLSPGERATLSCTATSSVSSSYLNWYQQKPGQAPRL
LIYSTSNLASGIPDRFSGSGSGTDFTLTISRLEPEDFAVYYCHQYHR
STPTFGGGTKVEIKRTVAAPSVFIFPPSDEQLKSGTASVVCLLNNFY
PREAKVQWKVDNALQSGNSQESVTEQDSKDSTYSLSSTLTLSKADYE
KHKVYACEVTHQGLSSPVTKSFNRGEC SS3 hIgG2Δa heavy chain amino acid sequence
(SEQ ID NO: 136)
EVQLVESGGGLVKPGGSLRLSCAASGFTFSDAWMDWVRQAPGKGLEW
VAEIRSKANNHATYYAESVKGRFTISRDDSKNTLYLQMNSLKTEDTA
VYYCTLFRDYWGQGTLVTVSSASTKGPSVFPLAPCSRSTSESTAALG
CLVKDYFPEPVTVSWNSGALTSGVHTFPAVLQSSGLYSLSSVVTVPS
SNFGTQTYTCNVDHKPSNTKVDKTVERKCCVECPPCPAPPVAGPSVF
LFPPKPKDTLMISRTPEVTCVVVDVSHEDPEVQFNWYVDGVEVHNAK
TKPREEQFNSTFRVVSVLTVVHQDWLNGKEYKCKVSNKGLPSSIEKT
ISKTKGQPREPQVYTLPPSREEMTKNQVSLTCLVKGFYPSDIAVEWE
SNGQPENNYKTTPPMLDSDGSFFLYSKLTVDKSRWQQGNVFSCSVMH
EALHNHYTQKSLSLSPGK SS3 hIgG2Δa light chain amino acid sequence
(SEQ ID NO: 137)
EIVLTQSPGTLSLSPGERATLSCTATSSVSSSYLNWYQQKPGQAPRL
LIYSTSNLASGIPDRFSGSGSGTDFTLTISRLEPEDFAVYYCHQYHR
FTPTFGGGTKVEIKRTVAAPSVFIFPPSDEQLKSGTASVVCLLNNFY
PREAKVQWKVDNALQSGNSQESVTEQDSKDSTYSLSSTLTLSKADYE
KHKVYACEVTHQGLSSPVTKSFNRGEC SS1 FcM heavy chain amino acid sequence
(SEQ ID NO: 138)
EVQLVESGGGLVKPGGSLRLSCAASGFTFSDAWMDWVRQAPGKGLEW
VAEIRSKANYHATYYAESVKGRFTISRDDSKNTLYLQMNSLKTEDTA
VYYCTLIRDYWGQGTLVTVSSASTKGPSVFPLAPCSRSTSESTAALG
CLVKDYFPEPVTVSWNSGALTSGVHTFPAVLQSSGLYSLSSVVTVPS
SNFGTQTYTCNVDHKPSNTKVDKTVERKCCVECPPCPAPPVAGPSVF
LFPPKPKDTLMISRTPEVTCVVVDVSHEDPEVQFNWYVDGVEVHNAK
TKPREEQFNSTFRVVSVLTVVHQDWLNGKEYKCKVSNKGLPSSIEKT
ISKTKGQPREPQVYTLPPSREEMTKNQVSLTCLVKGFYPSDIAVEWE
SNGQPENNYKTTPPMLDSDGSFFLYSKLTVDKSRWQQGNVFSCSVLH
EALHSHYTQKSLSLSPGK SS1 FcM light chain amino add sequence
(SEQ ID NO: 139)
EIVLTQSPGTLSLSPGERATLSCTATSSVSSSYLNWYQQKPGQAPRL
LIYSTSNLASGIPDRFSGSGSGTDFTLTISRLEPEDFAVYYCHQYHR
STPTFGGGTKVEIKRTVAAPSVFIFPPSDEQLKSGTASVVCLLNNFY
PREAKVQWKVDNALQSGNSQESVTEQDSKDSTYSLSSTLTLSKADYE
KHKVYACEVTHQGLSSPVTKSFNRGEC Antibodies SS3 and SS1 (hIgG2Δa) were tested using a STAT5 phosphorylation assay. For the STAT5 assay, full-length human GHR overexpressing HEK293 cells or full-length cyno GHR-overexpressing HEK293 cells were cultured, counted by automated cell counter, and seeded in warm freestyle media in 12-well plates ($5 \times 10^5$ cells/well in 1 ml media). Cells were allowed to settle for 3 hours at 37° C. then treated with 2.5, 5, 50, or 500 nM of SS1 or SS3 in media. Cells were incubated at 37° C. with gentle mixing for 5 min with antibodies, 4.5 nM human growth hormone (Pfizer) was then added to all but control wells. Cells were incubated with GH at 37° C. with gentle mixing for 10 minutes.

Following incubation with GH, 2 ml of ice cold DPBS with 1× protease inhibitor cocktail (Roche) and 1 mM sodium orthovanadate (BioLabs) were added to each well and the plates were placed on ice. Cells were transferred to 5 ml tubes and spun down to create a cell pellet and the wash buffer was aspirated, leaving the cell pellet.

Reagents from Millipore™ MILLIPLEX® MAP Cell Signaling Buffer and Detection Kit (cat. #48-602) were used to lyse and treat the cell pellets. Millipore™ lysis buffer with 1× protease inhibitor cocktail and sodium orthovanadate was added to each pellet at a volume of 100 ul/pellet Cells were vortexed and incubated for 15 minutes at room temp with occasional vortexing, Millipore™ Assay buffer 2 with 1× protease inhibitor cocktail and 1 mM sodium orthovanadate was then added to the lysates at 200 ul/well.

Millipore™ MILLIPLEX® MAP Phospho STAT5A/B (Tyr694/699) MAPmate™ beads (Cat. #46-641) were resuspended in Assay Buffer 2 (from Millipore kit cat. #48-602) and loaded on a 96-well filter plate (provided in kit) at 25 ul/well. 25 ul/well of sample lysate was added to the wells and the beads and samples were incubated overnight at 4'C with shaking in the dark.

The liquid was then aspirated using a vacuum manifold and the remaining beads were washed using Millipore™ kit wash buffer, 25 ul Millipore™ kit detection antibody was added and incubated for 1 hour at room temperature with shaking in the dark. The detection antibody was vacuumed through and 25 ul kit streptavidin-phycoerythrin was added and incubated in dark for 15 min with shaking, 25 ul kit amplification buffer was then added and incubated for 15 min with shaking in the dark. The liquid was aspirated using a vacuum manifold, and the beads were resuspended in 150 ul kit assay buffer 2 and mixed on a shaker for 5 minutes before reading the plate.

The plate was read using a Luminex 200 instrument and florescent signal emitted from the samples was measured. The results of the STAT5 assay are shown in Tables 7 and 8.

TABLE 7

STAT5 Assay Using Human GHR-transfected cells

| | | fluorescent signal | |
|---|---|---|---|
| Row | Treatment | ave | SEM |
| 1 | no GH | 0.0 | 0 |
| 2 | 4.5 nM GH | 252.6 | 46 |
| 3 | 2.5 nM SS1 + 4.5 nM GH | 60 | 4 |
| 4 | 5 nM SS1 + 4.5 nM GH | 22 | 16 |
| 5 | 50 nM SS1 + 4.5 nM GH | 0 | 0 |
| 6 | 500 nM SS1 + 4.5 nM GH | 5 | 4 |
| 7 | 2.5 nM SS3 + 4.5 nM GH | 100 | 63 |
| 8 | 5 nM SS3 + 4.5 nM GH | 48 | 27 |
| 9 | 50 nM SS3 + 4.5 nM GH | 0 | 0 |
| 10 | 500 nM SS3 + 4.5 nM GH | 0 | 0 |

TABLE 8

STAT5 Assay Using Cyno GHR-transfected cells

| | | fluorescent signal | |
|---|---|---|---|
| Row | Treatment | ave | SEM |
| 1 | no GH | 1.6 | 2.4 |
| 2 | 4.5 nM GH | 847 | 26.0 |
| 3 | 2.5 nM SS1 + 4.5 nM GH | 496 | 14.8 |
| 4 | 5 nM SS1 + 4.5 nM GH | 223 | 4.3 |
| 5 | 50 nM SS1 + 4.5 nM GH | 17 | 0.5 |
| 6 | 500 nM SS1 + 4.5 nM GH | 12 | 6.3 |
| 7 | 2.5 nM SS3 + 4.5 nM GH | 621 | 36.0 |
| 8 | 5 nM SS3 + 4.5 nM GH | 518 | 38.5 |
| 9 | 50 nM SS3 + 4.5 nM GH | 50 | 5.3 |
| 10 | 500 nM SS3 + 4.5 nM GH | 8 | 3.0 |

Treatment of GHR-transfected cells with 4.5 nM OH stimulated STAT5 signaling in delis expressing either human GHR (Table 7, row 2) or cyno GHR (Table 8, row 2). Humanized GHR antagonist antibodies SS1 and SS3 both blocked STAT5 signaling in a dose-dependent manner (Table 7, rows 3-10; Table 8, rows 3-10).

Example 4

GHR Antagonist Antibodies are Effective to Lower Blood IGF-1 Levels in Cynomolgus Monkeys This Example illustrates the effect of GHR antagonist antibodies on blood IGF-1 levels in cynomolgus monkeys.

To determine if GHR antagonist monoclonal antibodies can affect IGF-1 levels in vivo by inhibiting the function of GHR, the effect of murine anti-human GHR antibody Ab13 was tested in cynomolgus monkeys. IGF-1 levels are a biomarker for growth hormone activity in vivo. Blocking GHR has been shown to lead to a drop in IGF-1 levels as compared to baseline levels in vivo.

To test for changes in IGF-1 levels, five naïve female cynomolgus monkeys were injected IV with a single dose of Ab13 or negative control mouse IgG1 in 1×PBS. Two monkeys were dosed with 30 mg/kg Ab13, one was dosed with 10 mg/kg Ab13, and two were dosed with 30 mg/kg negative control mouse IgG1 on Day 1. Serum samples were taken from all animals at the following timepoints: pre-dose, 1 h, 4 h, 8 h, 12 h, 24 h, 48 h, 72 h, 96 h, 120 h, 144 h, 168 h, 216 h, 264 h, and 312 h post-dose.

Serum samples were analyzed for changes in IGF-1 levels compared to baseline using an R&D Systems™ Quantikine™ human IGF-1 immunoassay kit (cat. #DG100). The results of the study for the timepoints ranging from 24 h to 312 h are shown in Table 9.

TABLE 9

Effect of Ab13 on serum IGF-1 levels (% change from baseline)

| | Time post-injection | | | | | | | | | |
|---|---|---|---|---|---|---|---|---|---|---|
| Treatment | 24 h | 48 h | 72 h | 96 h | 120 h | 144 h | 168 h | 216 h | 264 h | 312 h |
| 10 mg/kg Ab13 (n = 1) | −33.1 | −46.2 | −38.6 | −48.8 | −42.8 | −31 | −35.3 | −36.8 | −24.2 | −3.4 |
| 30 mg/kg Ab13 (n = 2) | −24.2 +/− 5.6 | −53.7 +/− 0.1 | −55.5 +/− 1.5 | −62.65 +/− 1.85 | −63.5 +/− 4.3 | −63.05 +/− 7.15 | −59.05 +/− 6.85 | −51.2 +/− 8.5 | −37.15 +/− 5.65 | −4.5 +/− 6.9 |
| 30 mg/kg Control IgG1 (n = 2) | 3.75 +/− 2.05 | 3.3 +/− 3.9 | 5.35 +/− 1.05 | −2.75 +/− 2.95 | −4.2 +/− 9.1 | 12.6 +/− 8.4 | 2.1 +/− 8 | 14.3 +/− 0.4 | 15.55 +/− 3.35 | 25.9 +/− 9.2 |

The data in Table 9 shows that the GHR antagonist antibody Ab13 dose dependently reduces serum IGF-1 levels in cynomolgus monkeys. Serum IGF-1 levels decreased to about 63% below baseline by 96 hours after intravenous administration of a single dose of 30 mg/kg Ab13, and serum IGF-1 levels remained at about 63% below baseline until about 144 hours after antibody administration. Serum IGF-1 levels decreased to about 48.8% below control by 96 hours after intravenous administration of a single dose of 10 mg/kg Ab13. IGF-1 levels returned to baseline levels by hour 312. In contrast, serum IGF-1 levels in animals dosed with 30 mg/kg control IgG1 remained at about baseline levels throughout the study (Table 9). These results demonstrate that treatment with a GHR antagonist antibody is effective to lower IGF-1 levels in blood, and that the effect is dose-dependent.

Example 5

GHR Antagonist Antibodies are Effective to Lower Blood IGF-1, IGFBP-3, and ALS Levels in Cynomolgus Monkeys This Example illustrates the effect of GHR antagonist antibodies on blood IGF-1, IGF binding protein 3 (IGFBP-3) and acid-labile subunit (ALS) levels in cynomolgus monkeys.

To determine if GHR antagonist monoclonal antibodies can affect IGF-1, IGFBP-3, and ALS levels in vivo by inhibiting the function of GHR, the effect of humanized anti-human GHR antibody SS1 was tested in cynomolgus monkeys. A dose-response study was conducted to test for changes in IGF-1, IGFBP-3, and ALS levels following a single dose of SS1. Eight naïve female cynomolgus monkeys were injected intravenously with a single dose of SS1 or negative control human $IgG_2$, in 1×PBS 0.01% Tween™ 20. Two monkeys were dosed with 30 mg/kg SS1, two were dosed with 10 mg/kg SS1, two were dosed with 3 mg/kg SS1, and two were dosed with 30 mg/kg negative control human $IgG_{2\Delta a}$ on Day 1. Serum samples were taken from all animals at the following timepoints: pre-dose, 24 h, 48 h, 72 h, 120 h, 144 h, 192 h, 240 h, 336 h, 528 h, 696 h. Serum was also taken from the 30 mg/kg SS1 and negative control treated animals at 864 h post-dose.

Serum samples were analyzed for changes in IGF-1 levels compared to baseline using an R&D Systems™ Quantikine™ human IGF-1 immunoassay kit (cat. #DG100). The results of the study for the timepoints ranging from 24 h to 864 h are shown in Table 10.

TABLE 10

Effect of SS1 on serum IGF-1 levels (% change from baseline)

| | Time post-injection | | | | | | |
|---|---|---|---|---|---|---|---|
| Treatment | 24 h | 48 h | 72 h | 120 h | 144 h | 192 h | 240 h |
| SS1, 3 mg/kg | −43.6 +/− 0.5 | −66.6 +/− 1.1 | −67.1 +/− 1.6 | −76.2 +/− 7.9 | −68.4 +/− 1.1 | −65.2 +/− 3.0 | −34.5 +/− 17.8 |
| SS1, 10 mg/kg | −43.4 +/− 2.2 | −62.6 +/− 5.5 | −67.1 +/− 4.7 | −73.5 +/− 2.1 | −76.0 +/− 0.1 | −74.0 +/− 0.2 | −70.9 +/− 1.9 |
| SS1, 30 mg/kg | −43.2 +/− 3.0 | −63.2 +/− 5.0 | −68.5 +/− 5.8 | −75.2 +/− 5.2 | −77.5 +/− 5.6 | −77.2 +/− 3.3 | −74.8 +/− 3.4 |
| Control IgG1, 30 mg/kg | −14.4 +/− 2.3 | −47.1 +/− 3.5 | −9.2 +/− 6.4 | −6.6 +/− 2.3 | 0.8 +/− 1.4 | 6.8 +/− 12.4 | 4.9 +/− 14.8 |

| | Time post-injection | | | |
|---|---|---|---|---|
| Treatment | 336 h | 528 h | 696 h | 864 h |
| SS1, 3 mg/kg | 64.2 +/− 0.6 | 85.1 +/− 46.0 | 49.2 +/− 11.3 | |
| SS1, 10 mg/kg | −61.4 +/− 0.6 | 25.7 +/− 11.8 | 31.7 +/− 15.2 | |
| SS1, 30 mg/kg | −73.3 +/− 0.7 | −73.0 +/− 0.9 | −70.4 +/− 1.1 | −8.8 +/− 2.9 |
| Control IgG1, 30 mg/kg | 3.7 +/− 15.7 | 23.6 +/− 14.9 | 42.0 +/− 26.3 | 25.4 +/− 8.4 |

The data in Table 10 shows that the GHR antagonist antibody SS1 dose dependently reduces serum IGF-1 levels in cynomolgus monkey. In control animals dosed with 30 mg/kg IgG1, serum IGF-1 levels decreased to about 47% below baseline levels at 48 h after dosing with control IgG1, then returned to baseline level by 144 h post-dosing, and remained at about or above baseline level throughout the remainder of the study (Table 10, last row). In contrast, serum IGF-1 levels decreased to about 75% below baseline levels by 120 hours after intravenous administration of a single dose of 3, 10 or 30 mg/kg SS1. Serum IGF-1 levels in animals treated with SS1 remained substantially lower than baseline until 240 hours (3 mg/kg dose), 336 hours (10 mg/kg dose) or 696 hours (30 mg/kg dose) after dose administration. These results demonstrate that treatment with a GHR antagonist antibody is effective to lower IGF-1 levels in blood, and that the effect is dose-dependent.

Serum samples were analyzed for changes in IGFBP-3 levels compared to baseline using an R&D Systems™ Quantikine™ human IGFBP-3 immunoassay kit (cat. #DGB300). The results of the study for the timepoints ranging from 24 h to 336 h are shown in Table 11.

TABLE 11

Effect of SS1 on serum IGFBP-3 levels (% change from baseline)

| Treatment | Time post-injection | | | | |
|---|---|---|---|---|---|
| | 24 h | 48 h | 72 h | 96 h | 120 h |
| SS1, 3 mg/kg | −18.75 +/− 1.25 | −22.8 +/− 3.8 | −36.45 +/− 6.65 | −37.35 +/− 5.05 | −38.25 +/− 4.85 |
| SS1, 10 mg/kg | −23.95 +/− 3.35 | −28.4 +/− 2.9 | −37.9 +/− 2.4 | −40.95 +/− 0.35 | −46.4 +/− 1.1 |
| SS1, 30 mg/kg | −10.6 +/− 4.6 | −15.75 +/− 9.35 | −22.95 +/− 16.15 | −29.4 +/− 13.9 | −38.15 +/− 9.45 |
| Control IgG1, 30 mg/kg | 2.95 +/− 0.75 | −2.65 +/− 5.25 | −1.75 +/− 6.25 | −4 +/− 7.6 | 9 +/− 1.7 |

| Treatment | Time post-injection | | | |
|---|---|---|---|---|
| | 144 h | 192 h | 312 h | 336 h |
| SS1, 3 mg/kg | −46.8 +/− 0.6 | −32.55 +/− 1.35 | 22.4 +/− 1.9 | 28.15 +/− 12.25 |
| SS1, 10 mg/kg | −51.05 +/− 8.85 | −45.95 +/− 6.35 | −38.7 +/− 9.6 | −42.25 +/− 1.85 |
| SS1, 30 mg/kg | −45.7 +/− 11.9 | −31.05 +/− 16.05 | −40.65 +/− 5.05 | −39.45 +/− 0.85 |
| Control IgG1, 30 mg/kg | 2.85 +/− 1.25 | 10.3 +/− 2.2 | 20.25 +/− 6.15 | 21.7 +/− 22.5 |

The data in Table 11 shows that the GHR antagonist antibody SS1 dose dependently reduces serum IGFBP-3 levels in cynomolgus monkey. Serum IGFBP-3 levels decreased to about 36%, 38%, or 23% below baseline by 72 hours after intravenous administration of a single dose of 3, 10 or 30 mg/kg SS1, respectively. By 144 hours after dosing, serum IGFBP-3 levels in animals treated with 3, 10, or 30 mg/kg SS1 decreased to about 47%, 51%, or 46% below baseline, respectively. Serum IGFBP-3 animals treated with a single dose of SS1 antibody returned to baseline levels by the end of the study. Serum IGFBP-3 levels in animals dosed with 30 mg/kg control IgG1 remained at about baseline levels throughout the study (Table 11, last row). These results demonstrate that treatment with a GHR antagonist antibody is effective to lower IGFBP-3 levels in blood.

Serum samples were analyzed for changes in ALS levels compared to baseline using a BioVendor™ Human ALS ELISA kit (cat. #RMEE35R). The results of the study for the timepoints ranging from 24 h to 336 are shown in Table 12.

TABLE 12

Effect of SS1 on serum ALS levels (% change from baseline)

| Treatment | Time post-injection | | | | |
|---|---|---|---|---|---|
| | 24 h | 48 h | 72 h | 96 h | 120 h |
| SS1, 3 mg/kg | −23.0 +/− 4.0 | −41.7 +/− 3.6 | −45.4 +/− 0.9 | −50.7 +/− 2.3 | −48.0 +/− 0.4 |
| SS1, 10 mg/kg | 27.3 +/− 32.1 | −9.4 +/− 23.4 | −8.0 +/− 35.2 | −24.1 +/− 23.6 | −17.5 +/− 30.4 |
| SS1, 30 mg/kg | 3.9 +/− 4.2 | −35.1 +/− 1.9 | −34.9 +/− 10.5 | −48.8 +/− 8.0 | −41.2 +/− 13.9 |
| Control IgG1, 30 mg/kg | 8.6 +/− 3.5 | −9.7 +/− 9.3 | −2.6 +/− 2.3 | −5.6 +/− 2.6 | 5.6 +/− 5.6 |

TABLE 12-continued

Effect of SS1 on serum ALS levels (% change from baseline)

| Treatment | Time post-injection | | | |
|---|---|---|---|---|
| | 144 h | 192 h | 312 h | 336 h |
| SS1, 3 mg/kg | −45.5 +/− 8.4 | −50.7 +/− 8.8 | −22.0 +/− 8.2 | −23.7 +/− 6.4 |
| SS1, 10 mg/kg | −46.5 +/− 1.9 | −39.4 +/− 3.3 | −38.7 +/− 4.1 | −40.4 +/− 0.4 |
| SS1, 30 mg/kg | −50.0 +/− 4.4 | −50.2 +/− 2.0 | −47.1 +/− 2.7 | −50.1 +/− 4.4 |
| Control IgG1, 30 mg/kg | 4.5 +/− 1.9 | 2.1 +/− 13.4 | −0.5 +/− 2.7 | −9.8 +/− 1.0 |

The data in Table 12 shows that the GHR antagonist antibody SS1 reduces serum ALS levels in cynomolgus monkey. Serum ALS levels decreased to about 51%, 24%, or 49% by 96 hours after intravenous administration of a single dose of 3, 10 or 30 mg/kg SS1, respectively. Serum ALS animals treated with a single dose of SS1 antibody returned to baseline levels by the end of the study. Serum ALS levels in animals dosed with 30 mg/kg control IgG1 remained at about baseline levels throughout the study (Table 12, last row). These results demonstrate that treatment with a GHR antagonist antibody is effective to lower ALS levels in blood.

Animals were dosed subcutaneously to determine whether subcutaneous dosing of SS1 resulted in lowering of blood IGF-1 and ALS levels. Six naïve female cynomolgus monkeys were injected either intravenously or subcutaneously with a single dose of 381 or negative control human $IgG_{2\Delta a}$ in 1×PBS 0.01% Tween™ 20. Two monkeys were dosed with 3 mg/kg SS1 intravenously, two were dosed with 3 mg/kg SS1 subcutaneously, and two were dosed with 3 mg/kg negative control human $IgG_{2\Delta a}$ subcutaneously on Day 1. Serum samples were taken from all animals at the following timepoints: pre-dose, 24 h, 72 h, 120 h, 168 h, 216 h, 264 h, 312 h, 360 h, 408 h, 456 h and 504 h.

Serum samples were analyzed for changes in IGF-1 levels compared to baseline using an R&D Systems™ Quantikine™ human IGF-1 immunoassay kit (cat. #DG100). The results of the study for the timepoints ranging from 24 h to 360 h are shown in Table 13.

TABLE 13

Effect of SS1 on serum IGF-1 levels (% change from baseline)

| Treatment | Time post-injection (hour) | | | | | | | |
|---|---|---|---|---|---|---|---|---|
| | 24 | 72 | 120 | 168 | 216 | 264 | 312 | 360 |
| SS1, 3 mg/kg SQ | −46.7 +/− 9.9 | −62.5 +/− 2.5 | −68.7 +/− 2.8 | −65.6 +/− 4.1 | −60.7 +/− 10.2 | −40.9 +/− 25.6 | −15.3 +/− 23.4 | −4.2 +/− 22.6 |
| SS1, 3 mg/kg IV | −35 +/− 4.4 | −64.8 +/− 2.7 | −71.6 +/− 1.8 | −70.2 +/− 2.7 | −64.5 +/− 0.5 | −36.0 +/− 7.5 | −30.3 +/− 7.0 | −27.8 +/− 9.7 |
| Control IgG1, 3 mg/kg SQ | −1.7 +/− 3.9 | −9.4 +/− 7.2 | −4.2 +/− 5.8 | 6.2 +/− 2.9 | 2.3 +/− 9.1 | 0.5 +/− 12.4 | 4.1 +/− 17.9 | −4.0 +/− 8.8 |

The data in Table 13 shows that the GHR antagonist antibody SS1 dose dependently reduces serum IGF-1 levels in cynomolgus monkey when administered subcutaneously (SQ) or intravenously (IV). Serum IGF-1 levels, which decreased to about 63% below control by 72 hours after subcutaneous (SC) or intravenous (IV) administration of a single dose of 3 mg/kg SS1 Serum IGF-1 levels in animals treated with SS1 remained below 60% baseline levels until about 216 hour after dosing either SQ or IV, Serum IGF-1 levels in animals subcutaneously dosed with 3 mg/kg control IgG1 remained at about baseline levels throughout the study (Table 13, last row). These results demonstrate that treatment with a GHR antagonist antibody administered intravenously or subcutaneously is effective to lower IGF-1 levels in blood.

Serum samples were analyzed for changes in ALS levels compared to baseline using a BioVendor™ Human ALS ELISA kit (cat. #RMEE35R). The results of the study from the timepoints ranging from 24 h to 260 h are shown in Table 14.

TABLE 14

Effect of SS1 on serum ALS levels (% change from baseline)

| Treatment | Time post-injection (hour) | | | | | | |
|---|---|---|---|---|---|---|---|
| | 24 | 72 | 120 | 168 | 264 | 312 | 360 |
| SS1, 3 mg/kg SQ | −15.9 +/− 0.2 | −42.7 +/− 0.5 | −41.1 +/− 7.1 | −33.7 +/− 6.5 | −16.5 +/− 13.2 | −5.0 +/− 13.6 | −10.0 +/− 10.2 |
| SS1, 3 mg/kg IV | −4.5 +/− 4.6 | −31.1 +/− 10.1 | −37.5 +/− 9.4 | −32.9 +/− 4.0 | −9.3 +/− 2.5 | −4.9 +/− 3.0 | −9.7 +/− 9.6 |
| Control IgG1, 3 mg/kg SQ | 4.7 +/− 5.3 | 7.5 +/− 5.9 | 4.0 +/− 22.0 | 8.3 +/− 13.9 | 16.1 +/− 6.2 | 16.0 +/− 14.6 | 9.5 +/− 13.3 |

The data in Table 14 shows that the antagonist antibody SS1 dose dependently reduces serum ALS levels in cynomolgus monkey when administered subcutaneously (SQ) or intravenously (IV). Serum ALS levels, which decreased to about 43% below control by 72 hours after subcutaneous (SQ) administration of a single dose of 3 mg/kg SS1. ALS levels decreased to about 31% below control by 72 hours after intravenous (IV) administration of a single dose of 3 mg/kg SS1. Serum ALS levels returned to baseline levels by hour 312. Serum ALS levels in animals dosed with 3 mg/kg control IgG1 remained at or above baseline levels throughout the study (Table 14, last row). These results demonstrate that treatment with a GHR antagonist antibody administered intravenously or subcutaneously is effective to lower ALS levels in blood.

Example 6

GHR Antagonist Antibodies in Combination with Irinotecan are Effective to Inhibit Tumors in a Mouse Model of Cancer This Example illustrates the effect of GHR antagonist antibodies on tumor growth in a syngeneic mouse model of cancer.

To determine if GHR antagonist monoclonal antibodies can inhibit tumor growth, the effect of a mouse antibody, Ab11, was tested in a syngeneic tumor model. The Ab11 antibody is a mouse IgG1 antibody that blocks mouse GHR. The CT26 cell line was used as a syngeneic mouse model of colorectal cancer. Mice were injected with tumor cells and dosed with the Ab11 antibody alone or in combination with iriniotecan. A negative control group and an irinotecan alone group were also included in the study.

BALB/c mice (BALB/cAnNCrl) were obtained from Charles River (Hollister, Calif., USA) and maintained in the animal facility at Rinat. The animals were 7 weeks old with an initial body weight of 22-23 g when used for the study. The mice were housed in microisolators (filter top cages) under pathogen-free conditions with a 12-h light/12-h dark schedule and fed autoclaved standard chow and water throughout the experiment.

The mouse undifferentiated colon carcinoma cell line CT26 (CRL-2638) was obtained from the American Type Culture Collection (ATCC; Manassas, Va., USA). CT26 cells were grown in RPMI 1640, 1× with L-glutamine (10-040-CV) (Cellgro™ Mediatech™, Inc., Manassas, Va., USA) containing 10% fetal bovine serum (43640) (JR Scientific™, Inc., Woodland, Calif., USA) and 1% penicillin-streptomycin solution (30-002-CI) (Cellgro™ Mediatech™, Inc., Manassas, Va., USA). Cells were harvested by brief incubation with Accutase (A6964-100ML) (Sigma™ Aldrich, Inc., St. Louis, Mo., USA) and washed in new medium for counting. Cell count and viability (95.8%) was assessed using ViCell™, automated counter and viability machine. Final cell suspension in new medium was diluted 1:2 with BD Matrigel™ Matrix basement membrane (356234) (BD Biosciences™, Bedford, Mass., USA) for injection.

Tumor xenografts were initiated by subcutaneous (SC) injection of $10^5$ cells into the left flank of BALB/c mice. Seven days later, the tumors had grown to a volume of approximately 75-150 $mm^3$. The animals were divided into four groups with approximately equal average tumor volumes and standard errors of the mean and randomly allocated to receive treatment. Animals in the control group received 1×PBS with 10% Dimethyl sulfoxide (DMSO) (D2650—Sigma™ Aldrich, Inc., St. Louis, Mo., USA) plus 10 mg/kg mouse IgG1 isotype control antibody. Animals in the irinotecan group received 100 mg/kg Irinotecan hydrochloride (I1406—Sigma™ Aldrich), plus 10 mg/kg mouse IgG1 isotype control antibody. Animals in the Ab11 group received 10 mg/kg Ab11, plus 1×PBS with 10% DMSO. Animals in the combination group received 100 mg/kg irinotecan, plus 10 mg/kg Ab11.

Mice were dose intraperitoneally (IP) every second to third day. Tumor volume and body weight were measured at least twice a week. The study was blinded. On Day 28, blood was collected for measurement of serum IGF-1.

The tumors were measured every 2-4 days with a digital caliper (mm). Baseline tumor volumes were calculated using the following formula: $V=d2^2 \times (d1/2)$ where d1 was the longest diameter of the tumor and d2 was the perpendicular to d1. At the end of the study, while the study was still blinded, outliers were determined and excluded from all four groups. Tumors that were 3× standard error of the mean < mean and 3× standard error of the mean > mean on all days after day 14 (days 18, 22, 25, and 28) were determined outliers. Tumor weight at the end of the study was also measured.

Serum IGF-1 was measured by ELISA using a mouse/rat IGF-1 ELISA kit (MG100) (R&D Systems™, Inc., Minneapolis, Minn., USA).

The data from the mouse cancer model study are shown in Tables 16 and 17 below. Table 16 shows the mean tumor volume (in $mm^3$) in control animals, animals treated with GHR antagonist antibody Ab11, animals treated with irinotecan, and animals treated with both Ab11 and irinotecan. Table 17 shows the mean tumor weight (in grams) at day 28 in control animals, animals treated with GHR antagonist antibody Ab11, animals treated with irinotecan, and animals treated with both Ab11 and irinotecan. In Tables 15 and 16, the values are given as a mean for each group of animals treated with control IgG1 antibody, GHR antagonist antibody, irinotecan, or combination of GHR antagonist antibody and irinotecan. For the data in Tables 15 and 16, * indicates $p<0.05$ versus control,  indicates $p<0.01$ versus control, and * indicates $p<0.001$ versus control.

TABLE 15

Tumor volume (mm$^3$) in BALB/c mice bearing CT26 tumors.

|  | Control | | Ab11 | | Irinotecan | | Ab11 + irinotecan | | |
| --- | --- | --- | --- | --- | --- | --- | --- | --- | --- |
|  | mean | SEM | mean | SEM | mean | SEM | mean | SEM | |
| day 7 | 108.6 | 8.1 | 107.8 | 8.7 | 104.3 | 7.7 | 106.9 | 7.3 | |
| day 11 | 163.3 | 18.2 | 177.3 | 15.3 | 158.7 | 17.4 | 151.7 | 5.6 | |
| day 13 | 209.3 | 19.4 | 265.3 | 21.3 | 193.8 | 17.7 | 183.3 | 18.4 | |
| day 18 | 411.7 | 29.6 | 508.7 | 43.9 | 387.0 | 45.3 | 262.6 | 35.6 | |
| day 22 | 794.3 | 81.0 | 897.3 | 56.9 | 676.2 | 50.2 | 487.3 | 68.8 | |
| day 25 | 1204.6 | 158.6 | 1362.5 | 99.1 | 1053.7 | 88.3 | 745.1 | 87.0 | ** |
| day 28 | 1939.7 | 271.2 | 1897.2 | 172.5 | 1508.3 | 151.4 | 1092.1 | 132.2 | *** |

TABLE 16

Tumor weight (in grams) and serum IGF-1 levels (ng/mL) on day 28 in BALB/c mice bearing CT26 tumors.

|  | Control | | Ab11 | | Irinotecan | | Ab11 + irinotecan | |
| --- | --- | --- | --- | --- | --- | --- | --- | --- |
|  | mean | SEM | mean | SEAM | mean | SEM | mean | SEM |
| tumor weight | 1.9** g | 0.2** g | 1.9** g | 0.3** g | 1.2** g | 0.2** g | 0.8** g | 0.1** g |
| serum IGF-1 | 410.1 ng/mL | 7.8 ng/mL | 298.6 ng/mL | 3.842*** ng/mL | 454.9 ng/mL | 14.93* ng/mL | 278.0 ng/mL | 13.89*** ng/mL |

Table 15 shows mean tumor volume which was significantly lower in animals treated with GHR antagonist antibody in combination with irinotecan (1092.1 mm$^3$) than mean tumor volume in control animals (19397 mm$^3$).

Table 16 shows the Day 28 mean serum IGF-1 levels, which were significantly lower in animals treated with GHR antagonist antibody, either alone (298.6 ng/mL) or in combination with irinotecan (278 ng/mL), compared to the serum IGF-1 levels in control animals (410.1 ng/mL). These results demonstrate that treatment with a GHR antagonist antibody is effective to lower IGF-1 levels in blood in a mouse model of cancer. Table 16 also shows the Day 28 mean tumor weight, which was significantly lower in animals treated with GHR antagonist antibody in combination with irinotecan (0.8 g), compared to mean tumor weight in control animals (1.9 g). Treatment with irinotecan alone resulted in a mean tumor weight of 1.2 g. These results demonstrate that treatment with a GHR antagonist antibody in combination with irinotecan is effective to inhibit tumor growth in a mouse model of cancer.

Example 7

GHR Antagonist Antibodies are Effective to Reduce Disease Severity in a Mouse Model of Collagen-Induced Arthritis This Example illustrates the effect of GHR antagonist antibodies on disease severity in a mouse model of collagen-induced arthritis.

To determine if GHR antagonist monoclonal antibodies can reduce disease severity in arthritis the effect of a mouse antibody, Ab11, was tested in a mouse model of collagen-induced arthritis.

Forty-four male mice (strain B10.RIII-H2r H2-T18bl (71NS)SnJ. stock #000457) were purchased from Jackson Labs (Bar Harbor, Me.), and allowed to acclimate for several days after arrival. Animals were approximately 8 weeks old at the time of study start. Mice were randomly assigned to 4 groups of 10 to receive rheumatoid arthritis induction. A group of 4 healthy, untreated mice were analyzed as controls. On Day 0 and Day 15, disease group animals were anesthetized with isoflurane and injected intradermally with 200 µg bovine type II collagen (Elastin Products, Owensville, Mo.) in 100 µl Freund's complete adjuvant (Sigma-Aldrich, St. Louis, Mo.) with 4 mg/ml supplemental *mycobacterium tuberculosis* (Difco Laboratories, Detroit, Mich.). Animals received an intraperitoneal (IP) injection of the Ab11 test article or vehicle control prophylactically on Day −1. Twice weekly IP dosing with 3 mg/kg, 10 mg/kg, or 30 mg/kg of the Ab11 antibody or a vehicle control injection (PBS 0.01% polysorbate 20. JT Baker, Cat #4116-04, Phillipsburg, N.J.) followed for a period of one month. Mice were anesthetized with isoflurane and bled via orbital sinus for serum on Day −4, Day 15, and Day 29. Serum samples were frozen at −20° C. or below until time of analysis.

Clinical scores were observed and recorded for all four paws daily. Experimenters were blinded to the identity of the dosing groups at all times. Scores were determined according to the following criteria: 0=Healthy; 1=One hind or fore paw joint affected or minimal diffuse erythema and swelling; 2=Two hind or fore paw joints affected or mild diffuse erythema and swelling; 3=Three hind or fore paw joints affected or moderate diffuse erythema and swelling; 4=Marked diffuse erythema and swelling, or four digit joints affected; 5=Severe diffuse erythema and severe swelling entire paw, unable to flex digits.

On Day 29, half of the mice (5 per group for the disease set and 2 mice from healthy control set) were sacrificed and their fore paws, hind paws, and knees were removed and placed in neutral buffered formalin. The fore paws, hind paws, and knees were fixed for 1-2 days, then transferred to decalcifier for 4-5 days. These joints were embedded, sectioned, and stained with toluidine blue. Histopathologic scoring was performed on the paws and knees for inflammation, presence of pannus, cartilage damage, and bone damage. The following criteria were used for scoring the tissue. Inflammation:

0=Normal; 1=Minimal infiltration of inflammatory cells in synovium and periarticular tissue of affected joints; 2=Mild infiltration; if paws, restricted to affected joints; 3=Moderate infiltration with moderate edema; if paws, restricted to affected joints; 4=Marked infiltration affecting most areas with marked edema; 5=Severe diffuse infiltration with severe edema. Pannus: 0=Normal; 1=Minimal infiltration of pannus in cartilage and subchondral bone; 2=Mild infiltration with marginal zone destruction of hard tissue in affected joints; 3=Moderate infiltration with moderate hard tissue destruction in affected joints; 4=Marked infiltration with marked destruction of joint architecture, most joints; 5=Severe infiltration associated with total or near total destruction of joint architecture, affects all joints. Cartilage Damage: 0=Normal; 1=Minimal: Minimal to mild loss of toluidine blue staining with no obvious chondrocyte loss or collagen disruption in affected joints; 2=Mild: Mild loss of toluidine blue staining with focal mild (superficial) chondrocyte loss and/or collagen disruption in affected joints; 3=Moderate: Moderate loss of toluidine blue staining with multifocal moderate (depth to middle zone) chondrocyte loss and/or collagen disruption in affected joints; 4=Marked: Marked loss of toluidine blue staining with multifocal marked (depth to deep zone) chondrocyte loss and/or collagen disruption in most joints; 5=Severe: Severe diffuse loss of toluidine blue staining with multifocal severe (depth to tide mark) chondrocyte loss and/ or collagen disruption in all joints. Bone Resorption: 0=Normal; 1=Minimal: Minimal areas of resorption, not readily apparent on low magnification, rare osteoclasts in affected joints; 2=Mild: More numerous areas of resorption, not readily apparent on low magnification, osteoclasts more numerous in affected joints; 3=Moderate: Obvious resorption of medullary trabecular and cortical bone without full thickness defects in cortex, loss of some medullary trabeculae, lesion apparent on low magnification, osteoclasts more numerous in affected joints; 4=Marked: Full thickness defects in cortical bone, often with distortion of profile of remaining cortical surface, marked loss of medullary bone, numerous osteoclasts, affects most joints; 5=Severe: Full thickness defects in cortical bone and destruction of joint architecture of all joints.

Body weights were measured and recorded daily. The percent change in body weight from Day 14 (disease manifestation) until Day 29 was calculated for each group. On Day 29, half of the mice (5 per group for the disease set and 2 mice from healthy control set) were sacrificed and their hind paws were removed and weighed.

Serum from the Day 29 blood collection was analyzed for levels of Ab11 therapeutic antibodies. Nunc 96-well maxisorp ELISA plates (Cat #446612, Denmark) were coated with 100 µl/well of 5 µg/ml recombinant mouse GHR/Fc chimera (R&D Systems. Cat #1360-GR, Minneapolis, Minn.) in 1×PBS (Cellgro—Mediatech, Herndon, Va.). A 2-fold dilution series of Ab11 was used for the standard curve, with the highest dilution being 0.03 µg/ml. Standards and samples were diluted in assay buffer consisting of 0.5% BSA (Cat # A7906, Sigma, St. Louis, Mo.) in 1×PBS and loaded at 100 µl/well. A 1:2000 dilution of HRP-conjugated rabbit anti-mouse IgG1 (Zymed, Cat #61-0120, South San Francisco, Calif.) in assay buffer was used as a detection antibody. Elisa plates were developed using TMB substrate (Cat #50-76-02/50-65-02, KPL, Gaithersburg, Md.) and stopped with 1 M phosphoric acid. Plates were read at 450 nm on a Molecular Devices microplate reader.

Autoantibodies were measured from serum collected on study Days 15 and 29. Nunc ELISA plates were coated with 5 µg/ml bovine type II collagen (Rockland, Cat #001-001-104). A 1:5000 dilution of peroxidase-conjugated goat anti-mouse IgG (H+L) (Jackson ImmunoResearch labs. Cat #115-035-146, West Grove, Pa.) in assay buffer was used as a detection antibody. ELISA plates were developed using TMB substrate (Cat #50-76-02/50-65-02, KPL, Gaithersburg, Md.) and stopped with 1 M phosphoric acid. Plates were read at 450 nm on a Molecular Devices microplate reader. Optical density scores were plotted for each dilution.

Serum from the baseline, Day 15, and Day 29 blood collections was analyzed for levels of IGF-1. ELISAs were run using a Quantikine Mouse IGF-1 immunoassay kit (R&D Systems. Cat # MG100, Minneapolis, Minn.). Plates were read at 450 nm on a Molecular Devices microplate reader. Percent change from baseline IGF-1 was calculated for each timepoint. Animals treated with Ab11 showed a dose-dependent decrease in IGF-1 levels compared to control (data not shown).

On Day 31, half of the mice (5 per group for the disease set and 2 mice from healthy control set) were sacrificed and their inguinal lymph nodes were collected and analyzed for specific cell types using FACS analysis. Single cell suspensions from draining lymph nodes were generated by gently pushing the lymphoid tissue through a wire mesh with the rubber plunger end of a 3 ml syringe. After collection, the cells were washed in staining buffer (DPBS without $Mg^{2+}$ or $Ca^{2+}$ plus 1% heat-inactivated FCS, pH 7.4-7.6), and blocked with anti-CD16-CD32 (2.4G2, BD Biosciences, San Jose, Calif.). The cells were washed again, then stained for 30 minutes in the dark at 4° C. with fluorescence-labeled antibodies specific for cell surface markers CD4 (CD4-PerCP, BD Biosciences, Cat.#553052), CD8 (CD8-APC, BD Biosciences, Cat.#553035), IgD (IgD-FITC, BD Biosciences, Cat.#553439), and CD25 (CD25-PE, BD Biosciences, Cat.#558642). Data were acquired on a FACSAria (BD Biosciences) and were analyzed with FACS Diva software.

On Day 31, half of the mice (5 per group for the disease set and 2 mice from healthy control set) were sacrificed, and their spleens were collected and analyzed for specific cell types using FACS analysis. Single cell suspensions of splenocytes were generated by gently pushing the tissue through a wire mesh with the rubber plunger end of a 3 ml syringe. After collection, the cells were washed in staining buffer (DPBS without Mg2+ or Ca2+ plus 1% heat-inactivated FCS, pH 7.4-7.6), and blocked with anti-CD16-CD32 (2.4G2, BD Biosciences, San Jose, Calif.). The cells were washed again, then stained for 30 minutes in the dark at 4° C. with fluorescence-labeled antibodies specific for cell surface markers CD4 (CD4-PerCP, BD Biosciences, Cat.#553052), CD8 (CD8-APC, BD Biosciences, Cat.#553035), IgD (IgD-FITC, BD Biosciences, Cat.#553439), and CD25 (CD25-PE, BD Biosciences, Cat.#558642). Data were acquired on a FACSAria (BD Biosciences) and were analyzed with FACS Diva software.

On Day 31, half of the mice (5 per group for the disease set and 2 mice from healthy control set) were sacrificed, and whole blood was collected from the vehicle treated, 3 and 10 mg/kg Ab11 treated, and healthy control mice. No blood was collected from the 30 mg/kg treated mice. The blood was analyzed by flow cytometry using the ADVIA 120 Hematology System (Siemens Medical Solutions Diagnostics, Tarrytown, N.Y.). White blood cells were counted and reported in units of 1000 cells per cubic mm. Red Blood cells were counted and reported in units of one million cells per cubic mm. Lymphocytes and monocytes were counted and reported as percent of white blood cells. Neutrophils and eosinophils were counted and reported as percent of white blood cells.

Treatment with the GHR antagonist antibody Ab11 resulted in a decrease in clinical arthritis score compared to control. For example, at day 21, GHR antagonist antibody-treated animals had a clinical score (paw) of about 0.5 (30 mg/kg dose), about 0.7 (3 mg/kg dose), or about 1.1 (10 mg/kg dose). In contrast, at day 21, control animals had a clinical score of about 1.8. At day 29, GHR antagonist antibody-treated animals had a clinical score (paw) of around 2 to 2.5. In contrast, at day 29, control animals had a clinical score of about 3.5.

These results demonstrate that treatment with GHR antagonist antibodies is efficacious to reduce the severity in a mouse model of collagen-induced arthritis.

All patents, patent applications, Genbank entries, reference manuals, and publications cited above and elsewhere in the application are hereby incorporated by reference in their entirety for all purposes to the same extent as if each individual publication, patent, and patent application were specifically and individually indicated to be so incorporated by reference. In the even that one or more of the incorporated literature and similar materials differs from or contradicts this application, including but not limited to defined terms, term usage, described techniques, or the like, this application controls.

It is claimed:

1. An isolated growth hormone receptor (GHR) antagonist antibody that specifically binds to GHR and comprises: a heavy chain variable region (VH) comprising a VH complementary determining region one (CDR1), VH CDR2, and VH CDR3 of the VH comprising the amino acid sequence shown in SEQ ID NO: 8; and a light chain variable region (VL) comprising a VL CDR1, VL CDR2, and VL CDR3 of the VL comprising the amino acid sequence shown in SEQ ID NO: 7.

2. The isolated GHR antagonist antibody of claim 1, wherein the VH CDR1 comprises the amino acid sequence of SEQ ID NO: 1, 15 or 16, the VH CDR2 comprises the amino acid sequence of SEQ ID NO: 2 or 17, the VH CDR3 comprises the amino acid sequence of SEQ ID NO: 3, the VL CDR1 comprises the amino acid sequence of SEQ ID NO: 4, the VL CDR2 comprises the amino acid sequence of SEQ ID NO: 5, and the VL CDR3 comprises the amino acid sequence of SEQ ID NO: 6.

3. The isolated GHR antagonist antibody of claim 2, wherein the VH comprises the amino acid sequence of SEQ ID NO: 8 or a variant thereof with one or several conservative amino acid substitutions in residues that are not within a CDR, and the VL comprises the amino acid sequence of SEQ ID NO: 7 or a variant thereof with one or several amino acid substitutions in amino acids that are not within a CDR.

4. The isolated GHR antagonist antibody of claim 2, wherein the antibody further comprises an immunologically inert constant region.

5. The isolated GHR antagonist antibody of claim 4, wherein the antibody has an isotype that is selected from the group consisting of $IgG_2$, $IgG_{2\Delta a}$, $IgG_4$, $IgG_{4\Delta b}$, $IgG_{4\Delta c}$, $IgG_4$ S228P, $IgG_{4\Delta b}$ S228P and $IgG_{4\Delta c}$ S228P.

6. The isolated GHR antagonist antibody of claim 4, wherein the constant region is aglycosylated Fc.

7. The isolated GHR antagonist antibody of claim 3, wherein the antibody comprises a heavy chain comprising the amino acid sequence of SEQ ID NO: 134 or 133, and a light chain comprising the amino acid sequence of SEQ ID NO: 135.

8. A pharmaceutical composition comprising the antibody of claim 2.

9. A method for reducing a level of insulin-like growth factor-1 (IGF-1) in blood of an individual in need thereof, comprising administering to the individual a therapeutically effective amount of the antibody of claim 2.

10. The method of claim 9, wherein the level of IGF-1 is reduced at least about 40% or 60%.

11. The method of claim 9, wherein the individual has a disease selected from the group consisting of acromegaly, gigantism, cancer, diabetic nephropathy, arthritis, and lung inflammation.

12. A method for treating a disease selected from the group consisting of acromegaly, gigantism and rheumatoid arthritis in an individual in need thereof, comprising administering to the individual a therapeutically effective amount of the antibody of claim 2.

* * * * *

SEQUENCE LISTING

```
<160> NUMBER OF SEQ ID NOS: 146

<210> SEQ ID NO 1
<211> LENGTH: 10
<212> TYPE: PRT
<213> ORGANISM: Mus musculus

<400> SEQUENCE: 1

Gly Phe Thr Phe Ser Asp Ala Trp Met Asp
1               5                   10

<210> SEQ ID NO 2
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 2

Glu Ile Arg Ser Lys Ala Asn Tyr His Ala Thr Tyr Tyr Ala Glu Ser
1               5                   10                  15

Val Lys Gly

<210> SEQ ID NO 3
<211> LENGTH: 5
<212> TYPE: PRT
<213> ORGANISM: Artificial Sequence
<220> FEATURE:
<223> OTHER INFORMATION: Humanized and/or affinity matured antibody
      sequence

<400> SEQUENCE: 3

Ile Arg Asp Tyr Trp
1               5

<210> SEQ ID NO 4
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 4

Thr Ala Thr Ser Ser Val Ser Ser Ser Tyr Leu Asn
1               5                   10

<210> SEQ ID NO 5
<211> LENGTH: 7
<212> TYPE: PRT
<213> ORGANISM: Mus musculus
```

<400> SEQUENCE: 5

Ser Thr Ser Asn Leu Ala Ser
1               5

<210> SEQ ID NO 6
<211> LENGTH: 9
<212> TYPE: PRT
<213> ORGANISM: Mus musculus

<400> SEQUENCE: 6

His Gln Tyr His Arg Ser Thr Pro Thr
1               5

<210> SEQ ID NO 7
<211> LENGTH: 108
<212> TYPE: PRT
<213> ORGANISM: Artificial Sequence
<220> FEATURE:
<223> OTHER INFORMATION: Humanized and/or affinity matured antibody
      sequence

<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Thr Ala Thr Ser Ser Val Ser Ser Ser
            20                  25                  30

Tyr Leu Asp Trp Tyr Gln Gln Lys Pro Gly Gln Ala Pro Arg Leu Leu
        35                  40                  45

Ile Tyr Ser Thr Ser Asn Leu Ala Ser Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Ser Thr
                85                  90                  95

Pro Thr Phe Gly Gly Gly Thr Lys Val Glu Ile Lys
            100                 105

<210> SEQ ID NO 8
<211> LENGTH: 115
<212> TYPE: PRT
<213> ORGANISM: Artificial Sequence
<220> FEATURE:
<223> OTHER INFORMATION: Humanized and/or affinity matured antibody
      sequence

<400> SEQUENCE: 8

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Ser Lys Ala Asn Tyr His Ala Thr Tyr Tyr Ala Glu
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Ile Arg Asp Tyr Trp Gly Gln Gly Thr Leu Val Thr

Val Ser Ser
      115

<210> SEQ ID NO 9
<211> LENGTH: 108
<212> TYPE: PRT
<213> ORGANISM: Artificial Sequence
<220> FEATURE:
<223> OTHER INFORMATION: Humanized and/or affinity matured antibody
      sequence

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Thr Ala Thr Ser Ser Val Ser Ser Ser
            20                  25                  30

Tyr Leu Asn Trp Tyr Gln Gln Lys Pro Gly Gln Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Phe Thr
                85                  90                  95

Pro Thr Phe Gly Gly Gly Thr Lys Val Glu Ile Lys
            100                 105

<210> SEQ ID NO 10
<211> LENGTH: 115
<212> TYPE: PRT
<213> ORGANISM: Artificial Sequence
<220> FEATURE:
<223> OTHER INFORMATION: Humanized and/or affinity matured antibody
      sequence

<400> SEQUENCE: 10

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Phe Arg Asp Tyr Trp Gly Gln Gly Thr Leu Val Thr
            100                 105                 110

Val Ser Ser
      115

<210> SEQ ID NO 11
<211> LENGTH: 108
<212> TYPE: PRT
<213> ORGANISM: Artificial Sequence
<220> FEATURE:
<223> OTHER INFORMATION: Humanized and/or affinity matured antibody -continued sequence

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Thr Ala Thr Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Ser Thr
                85                  90                  95

Pro Thr Phe Gly Gly Gly Thr Lys Val Glu Ile Lys
            100                 105

<210> SEQ ID NO 12
<211> LENGTH: 115
<212> TYPE: PRT
<213> ORGANISM: Artificial Sequence
<220> FEATURE:
<223> OTHER INFORMATION: Humanized and/or affinity matured antibody
      sequence

<400> SEQUENCE: 12

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Ser Lys Ala Asn Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Tyr Arg Asp Tyr Trp Gly Gln Gly Thr Leu Val Thr
            100                 105                 110

Val Ser Ser
        115

<210> SEQ ID NO 13
<211> LENGTH: 108
<212> TYPE: PRT
<213> ORGANISM: Artificial Sequence
<220> FEATURE:
<223> OTHER INFORMATION: Humanized and/or affinity matured antibody
      sequence

<400> SEQUENCE: 13

Glu Ile Val Leu Thr Gln Ser Pro Gly Thr Leu Ser Leu Ser Pro Gly
1               5                   10                  15

Glu Arg Ala Thr Leu Ser Cys Thr Ala Thr Ser Ser Val Ser Ser Trp
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Ser Thr
                85                  90                  95

Pro Thr Phe Gly Gly Gly Thr Lys Val Glu Ile Lys
            100                 105

<210> SEQ ID NO 14
<211> LENGTH: 108
<212> TYPE: PRT
<213> ORGANISM: Artificial Sequence
<220> FEATURE:
<223> OTHER INFORMATION: Humanized and/or affinity matured antibody
      sequence

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Thr Ala Thr Ser Ser Val Ser Ser Ser
            20                  25                  30

Tyr Leu His Trp Tyr Gln Gln Lys Pro Gly Gln Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Gly Thr
                85                  90                  95

Pro Thr Phe Gly Gly Gly Thr Lys Val Glu Ile Lys
            100                 105

<210> SEQ ID NO 15
<211> LENGTH: 7
<212> TYPE: PRT
<213> ORGANISM: Mus musculus

<400> SEQUENCE: 15

Gly Phe Thr Phe Ser Asp Ala
1               5

<210> SEQ ID NO 16
<211> LENGTH: 5
<212> TYPE: PRT
<213> ORGANISM: Mus musculus

<400> SEQUENCE: 16

Asp Ala Trp Met Asp
1               5

<210> SEQ ID NO 17
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 17

Arg Ser Lys Ala Asn Tyr His Ala

<210> SEQ ID NO 18
<211> LENGTH: 12
<212> TYPE: PRT
<213> ORGANISM: Mus musculus

<400> SEQUENCE: 18

Thr Ala Thr Ser Ser Val Ser Ser Ser Tyr Leu His
1               5                   10

<210> SEQ ID NO 19
<211> LENGTH: 8
<212> TYPE: PRT
<213> ORGANISM: Mus musculus

<400> SEQUENCE: 19

Arg Ser Lys Ala Asn Asn His Ala
1               5

<210> SEQ ID NO 20
<211> LENGTH: 19
<212> TYPE: PRT
<213> ORGANISM: Mus musculus

<400> SEQUENCE: 20

Glu Ile Arg Ser Lys Ala Asn Asn His Ala Thr Tyr Tyr Ala Glu Ser
1               5                   10                  15

Val Lys Gly

<210> SEQ ID NO 21
<211> LENGTH: 5
<212> TYPE: PRT
<213> ORGANISM: Mus musculus

<400> SEQUENCE: 21

Tyr Arg Asp Tyr Trp
1               5

<210> SEQ ID NO 22
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 22

Thr Ala Thr Ser Ser Val Ser Ser Trp Tyr Leu His
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 23

Thr Ala Thr Ser Ser Val Ser Ser Phe Tyr Leu His
1               5                   10

<210> SEQ ID NO 24
<211> LENGTH: 12

```
<212> TYPE: PRT
<213> ORGANISM: Artificial Sequence
<220> FEATURE:
<223> OTHER INFORMATION: Humanized and/or affinity matured antibody
      sequence

<400> SEQUENCE: 24

Thr Ala Thr Ser Ser Val Ser Ser Ser Tyr Leu Asp
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Humanized and/or affinity matured antibody
      sequence

<400> SEQUENCE: 25

His Gln Tyr His Arg Phe Thr Pro Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 26

Arg Ser Lys Ala Asn Phe His Ala
1               5

<210> SEQ ID NO 27
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 27

Glu Ile Arg Ser Lys Ala Asn Phe His Ala Thr Tyr Tyr Ala Glu Ser
1               5                   10                  15

Val Lys Gly

<210> SEQ ID NO 28
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 28

Arg Ser Lys Ala Asn Asn Phe Ala
1               5

<210> SEQ ID NO 29
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 29
```

Glu Ile Arg Ser Lys Ala Asn Asn Phe Ala Thr Tyr Tyr Ala Glu Ser
1               5                   10                  15

Val Lys Gly

<210> SEQ ID NO 30
<211> LENGTH: 5
<212> TYPE: PRT
<213> ORGANISM: Artificial Sequence
<220> FEATURE:
<223> OTHER INFORMATION: Humanized and/or affinity matured antibody
      sequence

<400> SEQUENCE: 30

Phe Arg Asp Tyr Trp
1               5

<210> SEQ ID NO 31
<211> LENGTH: 6
<212> TYPE: PRT
<213> ORGANISM: Artificial Sequence
<220> FEATURE:
<223> OTHER INFORMATION: Humanized and/or affinity matured antibody
      sequence

<400> SEQUENCE: 31

Ile Tyr Arg Asp Tyr Trp
1               5

<210> SEQ ID NO 32
<211> LENGTH: 9
<212> TYPE: PRT
<213> ORGANISM: Artificial Sequence
<220> FEATURE:
<223> OTHER INFORMATION: Humanized and/or affinity matured antibody
      sequence

<400> SEQUENCE: 32

His Gln Tyr His Arg Arg Thr Pro Thr
1               5

<210> SEQ ID NO 33
<211> LENGTH: 9
<212> TYPE: PRT
<213> ORGANISM: Artificial Sequence
<220> FEATURE:
<223> OTHER INFORMATION: Humanized and/or affinity matured antibody
      sequence

<400> SEQUENCE: 33

His Gln Tyr His Arg Tyr Thr Pro Thr
1               5

<210> SEQ ID NO 34
<211> LENGTH: 9
<212> TYPE: PRT
<213> ORGANISM: Artificial Sequence
<220> FEATURE:
<223> OTHER INFORMATION: Humanized and/or affinity matured antibody
      sequence

<400> SEQUENCE: 34

His Gln Tyr His Arg His Thr Pro Thr
1               5

<210> SEQ ID NO 35
<211> LENGTH: 9

```
<212> TYPE: PRT
<213> ORGANISM: Artificial Sequence
<220> FEATURE:
<223> OTHER INFORMATION: Humanized and/or affinity matured antibody
      sequence

<400> SEQUENCE: 35

His Gln Tyr His Arg Gln Thr Pro Thr
1               5

<210> SEQ ID NO 36
<211> LENGTH: 9
<212> TYPE: PRT
<213> ORGANISM: Artificial Sequence
<220> FEATURE:
<223> OTHER INFORMATION: Humanized and/or affinity matured antibody
      sequence

<400> SEQUENCE: 36

His Gln Tyr His Arg Gly Thr Pro Thr
1               5

<210> SEQ ID NO 37
<211> LENGTH: 9
<212> TYPE: PRT
<213> ORGANISM: Artificial Sequence
<220> FEATURE:
<223> OTHER INFORMATION: Humanized and/or affinity matured antibody
      sequence

<400> SEQUENCE: 37

His Gln Tyr His Arg Ser Tyr Pro Thr
1               5

<210> SEQ ID NO 38
<211> LENGTH: 9
<212> TYPE: PRT
<213> ORGANISM: Artificial Sequence
<220> FEATURE:
<223> OTHER INFORMATION: Humanized and/or affinity matured antibody
      sequence

<400> SEQUENCE: 38

His Gln Tyr His Arg Ser Phe Pro Thr
1               5

<210> SEQ ID NO 39
<211> LENGTH: 9
<212> TYPE: PRT
<213> ORGANISM: Artificial Sequence
<220> FEATURE:
<223> OTHER INFORMATION: Humanized and/or affinity matured antibody
      sequence

<400> SEQUENCE: 39

His Gln Tyr His Arg Ser Ile Pro Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Humanized and/or affinity matured antibody
      sequence

<400> SEQUENCE: 40

His Gln Tyr His Arg Ser Trp Pro Thr
```

<210> SEQ ID NO 41
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 41

Arg Ala Thr Ser Ser Val Ser Ser Ser Tyr Leu His
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 42

Glu Ala Thr Ser Ser Val Ser Ser Ser Tyr Leu His
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 43

Thr Pro Thr Ser Ser Val Ser Ser Ser Tyr Leu His
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 44

Thr Ala Ser Ser Ser Val Ser Ser Ser Tyr Leu His
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 45

Thr Ala Thr Thr Ser Val Ser Ser Ser Tyr Leu His
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Humanized and/or affinity matured antibody

<400> SEQUENCE: 46

Thr Ala Thr Arg Ser Val Ser Ser Ser Tyr Leu His
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 47

Thr Ala Thr Trp Ser Val Ser Ser Ser Tyr Leu His
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 48

Thr Ala Thr Phe Ser Val Ser Ser Ser Tyr Leu His
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 49

Thr Ala Thr Ser Trp Val Ser Ser Ser Tyr Leu His
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 50

Thr Ala Thr Ser Val Val Ser Ser Ser Tyr Leu His
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 51

Thr Ala Thr Ser Asp Val Ser Ser Ser Tyr Leu His
1               5                   10

<210> SEQ ID NO 52

```
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 52

Thr Ala Thr Ser Ser Val Gly Ser Ser Tyr Leu His
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 53

Thr Ala Thr Ser Ser Val Trp Ser Ser Tyr Leu His
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 54

Thr Ala Thr Ser Ser Val Ser Pro Ser Tyr Leu His
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 55

Thr Ala Thr Ser Ser Val Ser Gln Ser Tyr Leu His
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 56

Thr Ala Thr Ser Ser Val Ser Ala Ser Tyr Leu His
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 57
```

Thr Ala Thr Ser Ser Val Ser Ser Gly Tyr Leu His
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 58

Thr Ala Thr Ser Ser Val Ser Ser Ile Tyr Leu His
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 59

Thr Ala Thr Ser Ser Val Ser Ser Glu Tyr Leu His
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 60

Thr Ala Thr Ser Ser Val Ser Ser Ser Trp Leu His
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 61

Thr Ala Thr Ser Ser Val Ser Ser Ser Tyr Val His
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Humanized and/or affinity matured antibody
      sequence

<400> SEQUENCE: 62

Thr Ala Thr Ser Ser Val Ser Ser Ser Tyr Phe His
1               5                   10

<210> SEQ ID NO 63
<211> LENGTH: 12
<212> TYPE: PRT
<213> ORGANISM: Artificial Sequence
<220> FEATURE:

<223> OTHER INFORMATION: Humanized and/or affinity matured antibody
      sequence

<400> SEQUENCE: 63

Thr Ala Thr Ser Ser Val Ser Ser Ser Tyr Leu Pro
1               5                   10

<210> SEQ ID NO 64
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 64

Arg Ala Lys Ala Asn Asn His Ala
1               5

<210> SEQ ID NO 65
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 65

Glu Ile Arg Ala Lys Ala Asn Asn His Ala Thr Tyr Tyr Ala Glu Ser
1               5                   10                  15

Val Lys Gly

<210> SEQ ID NO 66
<211> LENGTH: 9
<212> TYPE: PRT
<213> ORGANISM: Artificial Sequence
<220> FEATURE:
<223> OTHER INFORMATION: Humanized and/or affinity matured antibody
      sequence

<400> SEQUENCE: 66

His Gln Tyr His Arg Ser Ala Pro Thr
1               5

<210> SEQ ID NO 67
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 67

Arg Thr Lys Ala Asn Asn His Ala
1               5

<210> SEQ ID NO 68
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 68

Glu Ile Arg Thr Lys Ala Asn Asn His Ala Thr Tyr Tyr Ala Glu Ser
1               5                   10                  15

Val Lys Gly

<210> SEQ ID NO 69
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 69

Arg Ser Arg Ala Asn Asn His Ala
1               5

<210> SEQ ID NO 70
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 70

Glu Ile Arg Ser Arg Ala Asn Asn His Ala Thr Tyr Tyr Ala Glu Ser
1               5                   10                  15

Val Lys Gly

<210> SEQ ID NO 71
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 71

Arg Ser Glu Ala Asn Asn His Ala
1               5

<210> SEQ ID NO 72
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 72

Glu Ile Arg Ser Glu Ala Asn Asn His Ala Thr Tyr Tyr Ala Glu Ser
1               5                   10                  15

Val Lys Gly

<210> SEQ ID NO 73
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 73

Arg Ser Lys Asp Asn Asn His Ala
1               5

<210> SEQ ID NO 74

```
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 74

Glu Ile Arg Ser Lys Asp Asn Asn His Ala Thr Tyr Tyr Ala Glu Ser
1               5                   10                  15

Val Lys Gly

<210> SEQ ID NO 75
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 75

Arg Ser Lys Ser Asn Asn His Ala
1               5

<210> SEQ ID NO 76
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 76

Glu Ile Arg Ser Lys Ser Asn Asn His Ala Thr Tyr Tyr Ala Glu Ser
1               5                   10                  15

Val Lys Gly

<210> SEQ ID NO 77
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 77

Arg Ser Lys Val Asn Asn His Ala
1               5

<210> SEQ ID NO 78
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 78

Glu Ile Arg Ser Lys Val Asn Asn His Ala Thr Tyr Tyr Ala Glu Ser
1               5                   10                  15

Val Lys Gly

<210> SEQ ID NO 79
<211> LENGTH: 8
<212> TYPE: PRT
<213> ORGANISM: Artificial Sequence
```

```
<220> FEATURE:
<223> OTHER INFORMATION: Humanized and/or affinity matured antibody
      sequence

<400> SEQUENCE: 79

Arg Ser Lys Tyr Asn Asn His Ala
1               5

<210> SEQ ID NO 80
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 80

Glu Ile Arg Ser Lys Tyr Asn Asn His Ala Thr Tyr Tyr Ala Glu Ser
1               5                   10                  15

Val Lys Gly

<210> SEQ ID NO 81
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 81

Arg Ser Lys Glu Asn Asn His Ala
1               5

<210> SEQ ID NO 82
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 82

Glu Ile Arg Ser Lys Glu Asn Asn His Ala Thr Tyr Tyr Ala Glu Ser
1               5                   10                  15

Val Lys Gly

<210> SEQ ID NO 83
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 83

Arg Ser Lys Ala Asn Trp His Ala
1               5

<210> SEQ ID NO 84
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 84
```

```
Glu Ile Arg Ser Lys Ala Asn Trp His Ala Thr Tyr Tyr Ala Glu Ser
1               5                   10                  15

Val Lys Gly

<210> SEQ ID NO 85
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 85

Arg Ser Lys Ala Asn Ile His Ala
1               5

<210> SEQ ID NO 86
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 86

Glu Ile Arg Ser Lys Ala Asn Ile His Ala Thr Tyr Tyr Ala Glu Ser
1               5                   10                  15

Val Lys Gly

<210> SEQ ID NO 87
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 87

Arg Ser Lys Ala Asn Asp His Ala
1               5

<210> SEQ ID NO 88
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 88

Glu Ile Arg Ser Lys Ala Asn Asp His Ala Thr Tyr Tyr Ala Glu Ser
1               5                   10                  15

Val Lys Gly

<210> SEQ ID NO 89
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 89

Arg Ser Lys Ala Asn Lys His Ala
1               5
```

```
<210> SEQ ID NO 90
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 90

Glu Ile Arg Ser Lys Ala Asn Lys His Ala Thr Tyr Tyr Ala Glu Ser
1               5                   10                  15

Val Lys Gly

<210> SEQ ID NO 91
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 91

Arg Ser Lys Ala Asn Arg His Ala
1               5

<210> SEQ ID NO 92
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 92

Glu Ile Arg Ser Lys Ala Asn Arg His Ala Thr Tyr Tyr Ala Glu Ser
1               5                   10                  15

Val Lys Gly

<210> SEQ ID NO 93
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 93

Arg Ser Lys Ala Asn Asn Trp Ala
1               5

<210> SEQ ID NO 94
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 94

Glu Ile Arg Ser Lys Ala Asn Asn Trp Ala Thr Tyr Tyr Ala Glu Ser
1               5                   10                  15

Val Lys Gly

<210> SEQ ID NO 95
```

```
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 95

Arg Ser Lys Ala Asn Asn Ile Ala
1               5

<210> SEQ ID NO 96
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 96

Glu Ile Arg Ser Lys Ala Asn Asn Ile Ala Thr Tyr Tyr Ala Glu Ser
1               5                   10                  15

Val Lys Gly

<210> SEQ ID NO 97
<211> LENGTH: 8
<212> TYPE: PRT
<213> ORGANISM: Artificial Sequence
<220> FEATURE:
<223> OTHER INFORMATION: Humanized and/or affinity matured antibody
      sequence

<400> SEQUENCE: 97

Arg Ser Lys Ala Asn Asn Tyr Ala
1               5

<210> SEQ ID NO 98
<211> LENGTH: 19
<212> TYPE: PRT
<213> ORGANISM: Artificial Sequence
<220> FEATURE:
<223> OTHER INFORMATION: Humanized and/or affinity matured antibody
      sequence

<400> SEQUENCE: 98

Glu Ile Arg Ser Lys Ala Asn Asn Tyr Ala Thr Tyr Tyr Ala Glu Ser
1               5                   10                  15

Val Lys Gly

<210> SEQ ID NO 99
<211> LENGTH: 12
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (12)..(12)
<223> OTHER INFORMATION: Xaa can be H, D, P, or N

<400> SEQUENCE: 99

Thr Ala Thr Ser Ser Val Ser Ser Ser Tyr Leu Xaa
1               5                   10

<210> SEQ ID NO 100
<211> LENGTH: 12
```

```
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (4)..(4)
<223> OTHER INFORMATION: Xaa can be S, T, R, W, or F

<400> SEQUENCE: 100

Thr Ala Thr Xaa Ser Val Ser Ser Ser Tyr Leu His
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (5)..(5)
<223> OTHER INFORMATION: Xaa can be S, W, V, or D

<400> SEQUENCE: 101

Thr Ala Thr Ser Xaa Val Ser Ser Ser Tyr Leu His
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (7)..(7)
<223> OTHER INFORMATION: Xaa can be S, G, or W

<400> SEQUENCE: 102

Thr Ala Thr Ser Ser Val Xaa Ser Ser Tyr Leu His
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (8)..(8)
<223> OTHER INFORMATION: Xaa can be S, P, or Q

<400> SEQUENCE: 103

Thr Ala Thr Ser Ser Val Ser Xaa Ser Tyr Leu His
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
```

```
<222> LOCATION: (9)..(9)
<223> OTHER INFORMATION: Xaa can be S, G, I, E, W, or F

<400> SEQUENCE: 104

Thr Ala Thr Ser Ser Val Ser Ser Xaa Tyr Leu His
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (11)..(11)
<223> OTHER INFORMATION: Xaa can be L, V, or F

<400> SEQUENCE: 105

Thr Ala Thr Ser Ser Val Ser Ser Ser Tyr Xaa His
1               5                   10

<210> SEQ ID NO 106
<211> LENGTH: 9
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (6)..(6)
<223> OTHER INFORMATION: Xaa can be S, F, R, Y, H, Q, or G

<400> SEQUENCE: 106

His Gln Tyr His Arg Xaa Thr Pro Thr
1               5

<210> SEQ ID NO 107
<211> LENGTH: 9
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (7)..(7)
<223> OTHER INFORMATION: Xaa can be T, Y, F, I, A, or W

<400> SEQUENCE: 107

His Gln Tyr His Arg Ser Xaa Pro Thr
1               5

<210> SEQ ID NO 108
<211> LENGTH: 8
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (2)..(2)
<223> OTHER INFORMATION: Xaa can be S, A, or T

<400> SEQUENCE: 108

Arg Xaa Lys Ala Asn Asn His Ala
1               5
```

```
<210> SEQ ID NO 109
<211> LENGTH: 19
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (4)..(4)
<223> OTHER INFORMATION: Xaa can be S, A, or T

<400> SEQUENCE: 109

Glu Ile Arg Xaa Lys Ala Asn Asn His Ala Thr Tyr Tyr Ala Glu Ser
1               5                   10                  15

Val Lys Gly

<210> SEQ ID NO 110
<211> LENGTH: 8
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (3)..(3)
<223> OTHER INFORMATION: Xaa can be K, R, or E

<400> SEQUENCE: 110

Arg Ser Xaa Ala Asn Asn His Ala
1               5

<210> SEQ ID NO 111
<211> LENGTH: 19
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (5)..(5)
<223> OTHER INFORMATION: Xaa can be K, R, or E

<400> SEQUENCE: 111

Glu Ile Arg Ser Xaa Ala Asn Asn His Ala Thr Tyr Tyr Ala Glu Ser
1               5                   10                  15

Val Lys Gly

<210> SEQ ID NO 112
<211> LENGTH: 8
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (4)..(4)
<223> OTHER INFORMATION: Xaa can be A, D, S, V, Y, or E

<400> SEQUENCE: 112

Arg Ser Lys Xaa Asn Asn His Ala
1               5

<210> SEQ ID NO 113
```

```
<211> LENGTH: 19
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (6)..(6)
<223> OTHER INFORMATION: Xaa can be A, D, S, V, Y, or E

<400> SEQUENCE: 113

Glu Ile Arg Ser Lys Xaa Asn Asn His Ala Thr Tyr Tyr Ala Glu Ser
1               5                   10                  15

Val Lys Gly

<210> SEQ ID NO 114
<211> LENGTH: 8
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (6)..(6)
<223> OTHER INFORMATION: Xaa can be N, F, W, I, D, Y, K, or R

<400> SEQUENCE: 114

Arg Ser Lys Ala Asn Xaa His Ala
1               5

<210> SEQ ID NO 115
<211> LENGTH: 19
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (8)..(8)
<223> OTHER INFORMATION: Xaa can be N, F, W, I, D, Y, K, or R

<400> SEQUENCE: 115

Glu Ile Arg Ser Lys Ala Asn Xaa His Ala Thr Tyr Tyr Ala Glu Ser
1               5                   10                  15

Val Lys Gly

<210> SEQ ID NO 116
<211> LENGTH: 8
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (7)..(7)
<223> OTHER INFORMATION: Xaa can be H, W, I, Y, or F

<400> SEQUENCE: 116

Arg Ser Lys Ala Asn Asn Xaa Ala
1               5

<210> SEQ ID NO 117
<211> LENGTH: 19
<212> TYPE: PRT
<213> ORGANISM: Artificial Sequence
```

```
<220> FEATURE:
<223> OTHER INFORMATION: Humanized and/or affinity matured antibody
      sequence
<220> FEATURE:
<221> NAME/KEY: MISC_FEATURE
<222> LOCATION: (9)..(9)
<223> OTHER INFORMATION: Xaa can be H, W, I, Y or F

<400> SEQUENCE: 117

Glu Ile Arg Ser Lys Ala Asn Asn Xaa Ala Thr Tyr Tyr Ala Glu Ser
1               5                   10                  15

Val Lys Gly

<210> SEQ ID NO 118
<211> LENGTH: 5
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (1)..(1)
<223> OTHER INFORMATION: Xaa can be Y, F, or I

<400> SEQUENCE: 118

Xaa Arg Asp Tyr Trp
1               5

<210> SEQ ID NO 119
<211> LENGTH: 6
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (1)..(1)
<223> OTHER INFORMATION: Xaa can be L or I

<400> SEQUENCE: 119

Xaa Tyr Arg Asp Tyr Trp
1               5

<210> SEQ ID NO 120
<211> LENGTH: 12
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (9)..(9)
<223> OTHER INFORMATION: Xaa can be S, W, or F

<400> SEQUENCE: 120

Thr Ala Thr Ser Ser Val Ser Ser Xaa Tyr Leu His
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
```

```
<222> LOCATION: (12)..(12)
<223> OTHER INFORMATION: Xaa can be H, D, or N

<400> SEQUENCE: 121

Thr Ala Thr Ser Ser Val Ser Ser Tyr Leu Xaa
1               5                   10

<210> SEQ ID NO 122
<211> LENGTH: 9
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (7)..(7)
<223> OTHER INFORMATION: Xaa can be T, Y, F, I, or W

<400> SEQUENCE: 122

His Gln Tyr His Arg Ser Xaa Pro Thr
1               5

<210> SEQ ID NO 123
<211> LENGTH: 8
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (6)..(6)
<223> OTHER INFORMATION: Xaa can be N, F, or Y

<400> SEQUENCE: 123

Arg Ser Lys Ala Asn Xaa His Ala
1               5

<210> SEQ ID NO 124
<211> LENGTH: 19
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (8)..(8)
<223> OTHER INFORMATION: Xaa can be N, F, or Y

<400> SEQUENCE: 124

Glu Ile Arg Ser Lys Ala Asn Xaa His Ala Thr Tyr Tyr Ala Glu Ser
1               5                   10                  15

Val Lys Gly

<210> SEQ ID NO 125
<211> LENGTH: 8
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (7)..(7)
<223> OTHER INFORMATION: Xaa can be H or F

<400> SEQUENCE: 125
```

```
Arg Ser Lys Ala Asn Asn Xaa Ala
1               5
```

<210> SEQ ID NO 126
<211> LENGTH: 19
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (9)..(9)
<223> OTHER INFORMATION: Xaa can be H or F

<400> SEQUENCE: 126

```
Glu Ile Arg Ser Lys Ala Asn Asn Xaa Ala Thr Tyr Tyr Ala Glu Ser
1               5                   10                  15

Val Lys Gly
```

<210> SEQ ID NO 127
<211> LENGTH: 8
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (6)..(6)
<223> OTHER INFORMATION: Xaa can be N or Y

<400> SEQUENCE: 127

```
Arg Ser Lys Ala Asn Xaa His Ala
1               5
```

<210> SEQ ID NO 128
<211> LENGTH: 19
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (8)..(8)
<223> OTHER INFORMATION: Xaa can be N or Y

<400> SEQUENCE: 128

```
Glu Ile Arg Ser Lys Ala Asn Xaa His Ala Thr Tyr Tyr Ala Glu Ser
1               5                   10                  15

Val Lys Gly
```

<210> SEQ ID NO 129
<211> LENGTH: 5
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (1)..(1)
<223> OTHER INFORMATION: Xaa can be Y or I

<400> SEQUENCE: 129

```
Xaa Arg Asp Tyr Trp
1               5
```

<210> SEQ ID NO 130
<211> LENGTH: 9
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (6)..(6)
<223> OTHER INFORMATION: Xaa can be S, F, R, Y, H or G

<400> SEQUENCE: 130

His Gln Tyr His Arg Xaa Thr Pro Thr
1               5

<210> SEQ ID NO 131
<211> LENGTH: 12
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (12)..(12)
<223> OTHER INFORMATION: Xaa can be H or D

<400> SEQUENCE: 131

Thr Ala Thr Ser Ser Val Ser Ser Ser Tyr Leu Xaa
1               5                   10

<210> SEQ ID NO 132
<211> LENGTH: 9
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (6)..(6)
<223> OTHER INFORMATION: Xaa can be S or F

<400> SEQUENCE: 132

His Gln Tyr His Arg Xaa Thr Pro Thr
1               5

<210> SEQ ID NO 133
<211> LENGTH: 440
<212> TYPE: PRT
<213> ORGANISM: Artificial Sequence
<220> FEATURE:
<223> OTHER INFORMATION: Humanized and/or affinity matured antibody
      sequence

<400> SEQUENCE: 133

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Ser Lys Ala Asn Tyr His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Leu Ile Arg Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly
        435                 440

<210> SEQ ID NO 134
<211> LENGTH: 441
<212> TYPE: PRT
<213> ORGANISM: Artificial Sequence
<220> FEATURE:
<223> OTHER INFORMATION: Humanized and/or affinity matured antibody
      sequence

<400> SEQUENCE: 134

```
Glu Val Gln Leu Val Glu Ser Gly Gly Gly Leu Val Lys Pro Gly Gly
 1               5                  10                  15
Ser Leu Arg Leu Ser Cys Ala Ala Ser Gly Phe Thr Phe Ser Asp Ala
             20                  25                  30
Trp Met Asp Trp Val Arg Gln Ala Pro Gly Lys Gly Leu Glu Trp Val
         35                  40                  45
Ala Glu Ile Arg Ser Lys Ala Asn Tyr His Ala Thr Tyr Tyr Ala Glu
     50                  55                  60
Ser Val Lys Gly Arg Phe Thr Ile Ser Arg Asp Asp Ser Lys Asn Thr
 65                  70                  75                  80
Leu Tyr Leu Gln Met Asn Ser Leu Lys Thr Glu Asp Thr Ala Val Tyr
                 85                  90                  95
Tyr Cys Thr Leu Ile Arg Asp Tyr Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Cys Ser Arg Ser Thr Ser Glu Ser Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Asn Phe Gly
            180                 185                 190
Thr Gln Thr Tyr Thr Cys Asn Val Asp His Lys Pro Ser Asn Thr Lys
        195                 200                 205
Val Asp Lys Thr Val Glu Arg Lys Cys Cys Val Glu Cys Pro Pro Cys
    210                 215                 220
Pro Ala Pro Pro Val Ala Gly Pro Ser Val Phe Leu Phe Pro Pro Lys
225                 230                 235                 240
Pro Lys Asp Thr Leu Met Ile Ser Arg Thr Pro Glu Val Thr Cys Val
                245                 250                 255
Val Val Asp Val Ser His Glu Asp Pro Glu Val Gln Phe Asn Trp Tyr
            260                 265                 270
Val Asp Gly Val Glu Val His Asn Ala Lys Thr Lys Pro Arg Glu Glu
        275                 280                 285
Gln Phe Asn Ser Thr Phe Arg Val Val Ser Val Leu Thr Val Val His
    290                 295                 300
Gln Asp Trp Leu Asn Gly Lys Glu Tyr Lys Cys Lys Val Ser Asn Lys
305                 310                 315                 320
Gly Leu Pro Ser Ser Ile Glu Lys Thr Ile Ser Lys Thr Lys Gly Gln
                325                 330                 335
Pro Arg Glu Pro Gln Val Tyr Thr Leu Pro Pro Ser Arg Glu Glu Met
            340                 345                 350
Thr Lys Asn Gln Val Ser Leu Thr Cys Leu Val Lys Gly Phe Tyr Pro
        355                 360                 365
Ser Asp Ile Ala Val Glu Trp Glu Ser Asn Gly Gln Pro Glu Asn Asn
    370                 375                 380
Tyr Lys Thr Thr Pro Pro Met Leu Asp Ser Asp Gly Ser Phe Phe Leu
385                 390                 395                 400
Tyr Ser Lys Leu Thr Val Asp Lys Ser Arg Trp Gln Gln Gly Asn Val
                405                 410                 415
```

```
Phe Ser Cys Ser Val Met His Glu Ala Leu His Asn His Tyr Thr Gln
            420                 425                 430

Lys Ser Leu Ser Leu Ser Pro Gly Lys
        435                 440
```

<210> SEQ ID NO 135
<211> LENGTH: 215
<212> TYPE: PRT
<213> ORGANISM: Artificial Sequence
<220> FEATURE:
<223> OTHER INFORMATION: Humanized and/or affinity matured antibody
      sequence

<400> SEQUENCE: 135

```
Glu Ile Val Leu Thr Gln Ser Pro Gly Thr Leu Ser Leu Ser Pro Gly
1               5                   10                  15

Glu Arg Ala Thr Leu Ser Cys Thr Ala Thr Ser Ser Val Ser Ser Ser
            20                  25                  30

Tyr Leu Asn Trp Tyr Gln Gln Lys Pro Gly Gln Ala Pro Arg Leu Leu
        35                  40                  45

Ile Tyr Ser Thr Ser Asn Leu Ala Ser Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Ser Thr
                85                  90                  95

Pro Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 136
<211> LENGTH: 441
<212> TYPE: PRT
<213> ORGANISM: Artificial Sequence
<220> FEATURE:
<223> OTHER INFORMATION: Humanized and/or affinity matured antibody
      sequence

<400> SEQUENCE: 136

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45
```

Ala Glu Ile Arg Ser Lys Ala Asn Asn His Ala Thr Tyr Tyr Ala Glu
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Leu Phe Arg Asp Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
                180                 185                 190

Thr Gln Thr Tyr Thr Cys Asn Val Asp His Lys Pro Ser Asn Thr Lys
                195                 200                 205

Val Asp Lys Thr Val Glu Arg Lys Cys Cys Val Glu Cys Pro Pro Cys
210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
                260                 265                 270

Val Asp Gly Val Glu Val His Asn Ala Lys Thr Lys Pro Arg Glu Glu
                275                 280                 285

Gln Phe Asn Ser Thr Phe Arg Val Val Ser Val Leu Thr Val Val His
290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
                340                 345                 350

Thr Lys Asn Gln Val Ser Leu Thr Cys Leu Val Lys Gly Phe Tyr Pro
                355                 360                 365

Ser Asp Ile Ala Val Glu Trp Glu Ser Asn Gly Gln Pro Glu Asn Asn
                370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly Lys
                435                 440

<210> SEQ ID NO 137
<211> LENGTH: 215

```
<212> TYPE: PRT
<213> ORGANISM: Artificial Sequence
<220> FEATURE:
<223> OTHER INFORMATION: Humanized and/or affinity matured antibody
      sequence

<400> SEQUENCE: 137
```

| | | | | | | | | | | | | | | | |
|---|---|---|---|---|---|---|---|---|---|---|---|---|---|---|---|
| Glu | Ile | Val | Leu | Thr | Gln | Ser | Pro | Gly | Thr | Leu | Ser | Leu | Ser | Pro | Gly |
| 1 | | | | 5 | | | | | 10 | | | | | 15 | |
| Glu | Arg | Ala | Thr | Leu | Ser | Cys | Thr | Ala | Thr | Ser | Ser | Val | Ser | Ser | Ser |
| | | | 20 | | | | | 25 | | | | | 30 | | |
| Tyr | Leu | Asn | Trp | Tyr | Gln | Gln | Lys | Pro | Gly | Gln | Ala | Pro | Arg | Leu | Leu |
| | | | 35 | | | | | 40 | | | | | 45 | | |
| Ile | Tyr | Ser | Thr | Ser | Asn | Leu | Ala | Ser | Gly | Ile | Pro | Asp | Arg | Phe | Ser |
| | 50 | | | | | 55 | | | | | 60 | | | | |
| Gly | Ser | Gly | Ser | Gly | Thr | Asp | Phe | Thr | Leu | Thr | Ile | Ser | Arg | Leu | Glu |
| 65 | | | | | 70 | | | | | 75 | | | | | 80 |
| Pro | Glu | Asp | Phe | Ala | Val | Tyr | Tyr | Cys | His | Gln | Tyr | His | Arg | Phe | Thr |
| | | | | 85 | | | | | 90 | | | | | 95 | |
| Pro | Thr | Phe | Gly | Gly | Gly | Thr | Lys | Val | Glu | Ile | Lys | Arg | Thr | Val | Ala |
| | | | 100 | | | | | 105 | | | | | 110 | | |
| Ala | Pro | Ser | Val | Phe | Ile | Phe | Pro | Pro | Ser | Asp | Glu | Gln | Leu | Lys | Ser |
| | | | 115 | | | | | 120 | | | | | 125 | | |
| Gly | Thr | Ala | Ser | Val | Val | Cys | Leu | Leu | Asn | Asn | Phe | Tyr | Pro | Arg | Glu |
| | 130 | | | | | 135 | | | | | 140 | | | | |
| Ala | Lys | Val | Gln | Trp | Lys | Val | Asp | Asn | Ala | Leu | Gln | Ser | Gly | Asn | Ser |
| 145 | | | | | 150 | | | | | 155 | | | | | 160 |
| Gln | Glu | Ser | Val | Thr | Glu | Gln | Asp | Ser | Lys | Asp | Ser | Thr | Tyr | Ser | Leu |
| | | | | 165 | | | | | 170 | | | | | 175 | |
| Ser | Ser | Thr | Leu | Thr | Leu | Ser | Lys | Ala | Asp | Tyr | Glu | Lys | His | Lys | Val |
| | | | 180 | | | | | 185 | | | | | 190 | | |
| Tyr | Ala | Cys | Glu | Val | Thr | His | Gln | Gly | Leu | Ser | Ser | Pro | Val | Thr | Lys |
| | | | 195 | | | | | 200 | | | | | 205 | | |
| Ser | Phe | Asn | Arg | Gly | Glu | Cys | | | | | | | | | |
| | 210 | | | | | 215 | | | | | | | | | |

```
<210> SEQ ID NO 138
<211> LENGTH: 441
<212> TYPE: PRT
<213> ORGANISM: Artificial Sequence
<220> FEATURE:
<223> OTHER INFORMATION: Humanized and/or affinity matured antibody
      sequence

<400> SEQUENCE: 138
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Lys | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Asp | Ala |
| | | | 20 | | | | | 25 | | | | | 30 | | |
| Trp | Met | Asp | Trp | Val | Arg | Gln | Ala | Pro | Gly | Lys | Gly | Leu | Glu | Trp | Val |
| | | | 35 | | | | | 40 | | | | | 45 | | |
| Ala | Glu | Ile | Arg | Ser | Lys | Ala | Asn | Tyr | His | Ala | Thr | Tyr | Tyr | Ala | Glu |
| | 50 | | | | | 55 | | | | | 60 | | | | |
| Ser | Val | Lys | Gly | Arg | Phe | Thr | Ile | Ser | Arg | Asp | Asp | Ser | Lys | Asn | Thr |
| 65 | | | | | 70 | | | | | 75 | | | | | 80 |
| Leu | Tyr | Leu | Gln | Met | Asn | Ser | Leu | Lys | Thr | Glu | Asp | Thr | Ala | Val | Tyr |
| | | | | 85 | | | | | 90 | | | | | 95 | |

```
Tyr Cys Thr Leu Ile Arg Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Leu His Glu Ala Leu His Ser His Tyr Thr Gln
            420                 425                 430

Lys Ser Leu Ser Leu Ser Pro Gly Lys
        435                 440

<210> SEQ ID NO 139
<211> LENGTH: 215
<212> TYPE: PRT
<213> ORGANISM: Artificial Sequence
<220> FEATURE:
<223> OTHER INFORMATION: Humanized and/or affinity matured antibody
      sequence

<400> SEQUENCE: 139

Glu Ile Val Leu Thr Gln Ser Pro Gly Thr Leu Ser Leu Ser Pro Gly
1               5                   10                  15
```

```
Glu Arg Ala Thr Leu Ser Cys Thr Ala Thr Ser Ser Val Ser Ser Ser
             20                  25                  30

Tyr Leu Asn Trp Tyr Gln Gln Lys Pro Gly Gln Ala Pro Arg Leu Leu
             35                  40                  45

Ile Tyr Ser Thr Ser Asn Leu Ala Ser Gly Ile Pro Asp Arg Phe Ser
         50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Ser Thr
                 85                  90                  95

Pro Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 140
<211> LENGTH: 638
<212> TYPE: PRT
<213> ORGANISM: Homo sapiens

<400> SEQUENCE: 140

Met Asp Leu Trp Gln Leu Leu Thr Leu Ala Leu Ala Gly Ser Ser
1               5                   10                  15

Asp Ala Phe Ser Gly Ser Glu Ala Thr Ala Ala Ile Leu Ser Arg Ala
             20                  25                  30

Pro Trp Ser Leu Gln Ser Val Asn Pro Gly Leu Lys Thr Asn Ser Ser
             35                  40                  45

Lys Glu Pro Lys Phe Thr Lys Cys Arg Ser Pro Glu Arg Glu Thr Phe
         50                  55                  60

Ser Cys His Trp Thr Asp Glu Val His His Gly Thr Lys Asn Leu Gly
65                  70                  75                  80

Pro Ile Gln Leu Phe Tyr Thr Arg Arg Asn Thr Gln Glu Trp Thr Gln
                 85                  90                  95

Glu Trp Lys Glu Cys Pro Asp Tyr Val Ser Ala Gly Glu Asn Ser Cys
            100                 105                 110

Tyr Phe Asn Ser Ser Phe Thr Ser Ile Trp Ile Pro Tyr Cys Ile Lys
            115                 120                 125

Leu Thr Ser Asn Gly Gly Thr Val Asp Glu Lys Cys Phe Ser Val Asp
130                 135                 140

Glu Ile Val Gln Pro Asp Pro Pro Ile Ala Leu Asn Trp Thr Leu Leu
145                 150                 155                 160

Asn Val Ser Leu Thr Gly Ile His Ala Asp Ile Gln Val Arg Trp Glu
```

```
                165                 170                 175
Ala Pro Arg Asn Ala Asp Ile Gln Lys Gly Trp Met Val Leu Glu Tyr
            180                 185                 190
Glu Leu Gln Tyr Lys Glu Val Asn Glu Thr Lys Trp Lys Met Met Asp
            195                 200                 205
Pro Ile Leu Thr Thr Ser Val Pro Val Tyr Ser Leu Lys Val Asp Lys
            210                 215                 220
Glu Tyr Glu Val Arg Val Arg Ser Lys Gln Arg Asn Ser Gly Asn Tyr
225                 230                 235                 240
Gly Glu Phe Ser Glu Val Leu Tyr Val Thr Leu Pro Gln Met Ser Gln
            245                 250                 255
Phe Thr Cys Glu Glu Asp Phe Tyr Phe Pro Trp Leu Leu Ile Ile Ile
            260                 265                 270
Phe Gly Ile Phe Gly Leu Thr Val Met Leu Phe Val Phe Leu Phe Ser
            275                 280                 285
Lys Gln Gln Arg Ile Lys Met Leu Ile Leu Pro Pro Val Pro Val Pro
            290                 295                 300
Lys Ile Lys Gly Ile Asp Pro Asp Leu Leu Lys Glu Gly Lys Leu Glu
305                 310                 315                 320
Glu Val Asn Thr Ile Leu Ala Ile His Asp Ser Tyr Lys Pro Glu Phe
            325                 330                 335
His Ser Asp Asp Ser Trp Val Glu Phe Ile Glu Leu Asp Ile Asp Glu
            340                 345                 350
Pro Asp Glu Lys Thr Glu Glu Ser Asp Thr Asp Arg Leu Leu Ser Ser
            355                 360                 365
Asp His Glu Lys Ser His Ser Asn Leu Gly Val Lys Asp Gly Asp Ser
            370                 375                 380
Gly Arg Thr Ser Cys Cys Glu Pro Asp Ile Leu Glu Thr Asp Phe Asn
385                 390                 395                 400
Ala Asn Asp Ile His Glu Gly Thr Ser Glu Val Ala Gln Pro Gln Arg
            405                 410                 415
Leu Lys Gly Glu Ala Asp Leu Leu Cys Leu Asp Gln Lys Asn Gln Asn
            420                 425                 430
Asn Ser Pro Tyr His Asp Ala Cys Pro Ala Thr Gln Gln Pro Ser Val
            435                 440                 445
Ile Gln Ala Glu Lys Asn Lys Pro Gln Pro Leu Pro Thr Glu Gly Ala
            450                 455                 460
Glu Ser Thr His Gln Ala Ala His Ile Gln Leu Ser Asn Pro Ser Ser
465                 470                 475                 480
Leu Ser Asn Ile Asp Phe Tyr Ala Gln Val Ser Asp Ile Thr Pro Ala
            485                 490                 495
Gly Ser Val Val Leu Ser Pro Gly Gln Lys Asn Lys Ala Gly Met Ser
            500                 505                 510
Gln Cys Asp Met His Pro Glu Met Val Ser Leu Cys Gln Glu Asn Phe
            515                 520                 525
Leu Met Asp Asn Ala Tyr Phe Cys Glu Ala Asp Ala Lys Lys Cys Leu
            530                 535                 540
Pro Val Ala Pro His Ile Lys Val Glu Ser His Ile Gln Pro Ser Leu
545                 550                 555                 560
Asn Gln Glu Asp Ile Tyr Ile Thr Thr Glu Ser Leu Thr Thr Ala Ala
            565                 570                 575
Gly Arg Pro Gly Thr Gly Glu His Val Pro Gly Ser Glu Met Pro Val
            580                 585                 590
```

Pro Asp Tyr Thr Ser Ile His Ile Val Gln Ser Pro Gln Gly Leu Ile
        595                 600                 605

Leu Asn Ala Thr Ala Leu Pro Leu Pro Asp Lys Glu Phe Leu Ser Ser
        610                 615                 620

Cys Gly Tyr Val Ser Thr Asp Gln Leu Asn Lys Ile Met Pro
625                 630                 635

<210> SEQ ID NO 141
<211> LENGTH: 637
<212> TYPE: PRT
<213> ORGANISM: Macaca fascicularis

<400> SEQUENCE: 141

Met Asp Leu Trp Gln Leu Leu Leu Thr Phe Ala Leu Ala Gly Ser Ser
1               5                   10                  15

Asp Ala Phe Ser Gly Ser Glu Pro Thr Ala Ala Ile Leu Ser Arg Ala
            20                  25                  30

Ser Trp Ser Leu Gln Ser Val Asn Pro Asp Leu Lys Thr Asn Ser Ser
        35                  40                  45

Lys Glu Pro Lys Phe Thr Lys Cys Arg Ser Pro Glu Arg Glu Thr Phe
50                  55                  60

Ser Cys His Trp Thr Asp Ala Val His Gly Leu Lys Ser Leu Gly
65                  70                  75                  80

Pro Ile Gln Leu Phe Tyr Thr Arg Arg Asn Ile Gln Glu Gln Thr Gln
                85                  90                  95

Glu Trp Lys Glu Cys Pro Asp Tyr Val Ser Ala Gly Glu Asn Ser Cys
            100                 105                 110

Tyr Phe Asn Ser Ser Phe Thr Ser Val Trp Ile Pro Tyr Cys Ile Lys
        115                 120                 125

Leu Thr Ser Asn Gly Asp Thr Val Asp Gly Lys Cys Phe Ser Val Asp
130                 135                 140

Glu Ile Val Gln Pro Asp Pro Pro Ile Ala Leu Asn Trp Thr Leu Leu
145                 150                 155                 160

Asn Val Ser Leu Thr Gly Ile His Ala Asp Ile Gln Val Arg Trp Glu
                165                 170                 175

Ala Pro Pro Asn Ala Asp Ile Gln Lys Gly Trp Met Val Leu Glu Tyr
            180                 185                 190

Glu Leu Gln Tyr Lys Glu Val Asn Glu Thr Lys Trp Lys Met Met Asp
        195                 200                 205

Pro Ile Leu Ser Thr Ser Val Pro Val Tyr Ser Leu Lys Val Asp Lys
210                 215                 220

Glu Tyr Glu Val Arg Val Arg Ser Lys Arg Arg Asn Ser Arg Asn Tyr
225                 230                 235                 240

Gly Glu Phe Ser Glu Val Leu Tyr Val Thr Leu Pro Gln Met Asn Gln
                245                 250                 255

Phe Thr Cys Glu Glu Asp Phe Tyr Phe Pro Trp Leu Leu Ile Ile Ile
            260                 265                 270

Phe Gly Ile Phe Gly Leu Thr Val Met Leu Phe Val Phe Leu Phe Ser
        275                 280                 285

Lys Gln Gln Arg Ile Lys Met Leu Ile Leu Pro Pro Val Pro Val Pro
290                 295                 300

Lys Ile Lys Gly Ile Asp Pro Asp Leu Leu Lys Glu Gly Lys Leu Glu
305                 310                 315                 320

Glu Val Asn Thr Ile Leu Ala Ile His Asp Ser Tyr Lys Pro Glu Phe

```
            325                 330                 335
His Ser Asp Asp Ser Trp Val Glu Phe Ile Glu Leu Asp Ile Asp Glu
            340                 345                 350
Pro Asp Glu Lys Asn Glu Gly Ser Asp Thr Asp Arg Leu Leu Ser Ser
            355                 360                 365
Asp His Gln Lys Ser His Ser Asn Leu Gly Val Lys Asp Gly Asp Ser
        370                 375                 380
Gly Arg Thr Ser Cys Tyr Glu Pro Asp Ile Leu Glu Thr Asp Phe Asn
385                 390                 395                 400
Ala Asn Asn Ile His Glu Gly Thr Ser Glu Val Ala Gln Pro Gln Arg
            405                 410                 415
Leu Lys Gly Glu Ala Asp Leu Leu Cys Leu Asp Gln Lys Asn Gln Asn
            420                 425                 430
Lys Pro Pro Tyr His Asp Ala Cys Pro Ala Thr Gln Gln Pro Ser Val
            435                 440                 445
Ile Gln Ala Glu Lys Asn Lys Pro Gln Pro Leu Pro Thr Asp Gly Ala
        450                 455                 460
Glu Ser Thr His Gln Ala Ala His Ile Gln Leu Ser Asn Pro Ser Ser
465                 470                 475                 480
Leu Ala Asn Ile Asp Phe Tyr Ala Gln Val Ser Asp Ile Thr Pro Ala
            485                 490                 495
Gly Ser Val Val Leu Ser Pro Gly Gln Lys Asn Lys Ala Gly Met Ser
            500                 505                 510
Gln Cys Asp Met His Leu Glu Met Val Ser Leu Cys Gln Glu Asp Phe
            515                 520                 525
Ile Met Asp Asn Ala Tyr Phe Cys Glu Ala Asp Ala Lys Lys Cys Ile
        530                 535                 540
Pro Val Ala Pro His Ile Lys Val Glu Ser His Ile Glu Pro Ser Phe
545                 550                 555                 560
Asn Gln Glu Asp Ile Tyr Ile Thr Thr Glu Ser Leu Thr Thr Thr Ala
            565                 570                 575
Gly Arg Pro Gly Thr Thr Glu His Ile Pro Gly Ser Glu Met Pro Val
            580                 585                 590
Pro Asp Tyr Thr Ser Ile His Ile Val Gln Ser Pro Gln Gly Leu Ile
            595                 600                 605
Leu Asn Ala Thr Ala Leu Pro Leu Pro Gly Lys Glu Phe Leu Ser Ser
        610                 615                 620
Cys Gly Tyr Val Ser Thr Asp Gln Leu Asn Lys Ile Met
625                 630                 635

<210> SEQ ID NO 142
<211> LENGTH: 1323
<212> TYPE: DNA
<213> ORGANISM: Artificial Sequence
<220> FEATURE:
<223> OTHER INFORMATION: Humanized and/or affinity matured antibody
      sequence

<400> SEQUENCE: 142
gaggtgcagc tggtggaatc tggcggcgga ctggtgaaac tggcggcag cctgagactg      60 agctgcgccg ccagcggctt caccttcagc gacgcctgga tggactgggt gcgccaggcc    120
cctggcaagg gactggaatg ggtggccgag atcagaagca aggccaacta tcacgccacc    180
tactacgccg agagcgtgaa gggccggttc accatcagcc gggacgacag caagaacacc    240
ctgtacctgc agatgaacag cctgaaaacc gaggacaccg ccgtgtacta ctgcaccctg    300
```

```
attagagact actggggcca gggcaccctg gtcaccgtct cctcagcctc caccaagggc    360
ccatcggtct tccccctggc gccctgctcc aggagcacct ccgagagcac agcggccctg    420
ggctgcctgg tcaaggacta cttccccgaa ccggtgacgg tgtcgtggaa ctcaggcgct    480
ctgaccagcg gcgtgcacac cttcccggct gtcctacagt cctcaggact ctactccctc    540
agcagcgtag tgaccgtgcc ctccagcaac ttcggcaccc agacctacac ctgcaacgta    600
gatcacaagc ccagcaacac caaggtggac aagacagttg agcgcaaatg ttgtgtcgag    660
tgcccaccgt gcccagcacc acctgtggca ggaccgtcag tcttcctctt ccccccaaaa    720
cccaaggaca ccctcatgat ctcccggacc cctgaggtca cgtgcgtggt ggtggacgtg    780
agccacgaag accccgaggt ccagttcaac tggtacgtgg acggcgtgga ggtgcataat    840
gccaagacaa agccacggga ggagcagttc aacagcacgt tccgtgtggt cagcgtcctc    900
accgtcgtgc accaggactg gctgaacggc aaggagtaca gtgcaaggt ctccaacaaa    960 ggcctcccat cctccatcga gaaaaccatc tccaaaacca aagggcagcc cgagaacca    1020 caggtgtaca ccctgccccc atcccgggag gagatgacca gaaccaggt cagcctgacc    1080 tgcctggtca aaggcttcta ccccagcgac atcgccgtgg agtgggagag caatgggcag    1140
ccggagaaca actacaagac cacacctccc atgctggact ccgacggctc cttcttcctc    1200
tacagcaagc tcaccgtgga caagagcagg tggcagcagg gaacgtctt ctcatgctcc     1260 gtgatgcatg aggctctgca caaccactac acacagaaga gcctctccct gtctccgggt    1320
aaa                                                                   1323
```

<210> SEQ ID NO 143
<211> LENGTH: 645
<212> TYPE: DNA
<213> ORGANISM: Artificial Sequence
<220> FEATURE:
<223> OTHER INFORMATION: Humanized and/or affinity matured antibody
      sequence

<400> SEQUENCE: 143

```
gagatcgtgc tgacccagag ccccggcacc ctgtctctga gccctggcga gagagccacc     60
ctgagctgta ccgccaccag cagcgtgtcc agcagctacc tgaattggta tcagcagaag    120
cccggccagg cccccagact gctgatctac agcaccagca acctggccag cggcatcccc    180
gacagattca gcggcagcgg ctccggcacc gacttcaccc tgaccatcag ccggctggaa    240
cccgaggact tcgccgtgta ctactgccac cagtaccaca aagcacccc caccttcggc    300 ggaggcacca aggtggagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                    645
```

<210> SEQ ID NO 144
<211> LENGTH: 15
<212> TYPE: PRT
<213> ORGANISM: Artificial Sequence
<220> FEATURE:
<223> OTHER INFORMATION: Synthetic peptide linker

<400> SEQUENCE: 144

```
Gly Gly Gly Gly Ser Gly Gly Gly Ser Gly Gly Gly Ser
1               5                   10                  15

<210> SEQ ID NO 145
<211> LENGTH: 205
<212> TYPE: PRT
<213> ORGANISM: Macaca fascicularis

<400> SEQUENCE: 145

Glu Pro Lys Phe Thr Lys Cys Arg Ser Pro Glu Arg Glu Thr Phe Ser
1               5                   10                  15

Cys His Trp Thr Asp Ala Val His His Gly Leu Lys Ser Leu Gly Pro
                20                  25                  30

Ile Gln Leu Phe Tyr Thr Arg Arg Asn Ile Gln Glu Gln Thr Gln Glu
            35                  40                  45

Trp Lys Glu Cys Pro Asp Tyr Val Ser Ala Gly Glu Asn Ser Cys Tyr
    50                  55                  60

Phe Asn Ser Ser Phe Thr Ser Val Trp Ile Pro Tyr Cys Ile Lys Leu
65                  70                  75                  80

Thr Ser Asn Gly Asp Thr Val Asp Gly Lys Cys Phe Ser Val Asp Glu
                85                  90                  95

Ile Val Gln Pro Asp Pro Pro Ile Ala Leu Asn Trp Thr Leu Leu Asn
            100                 105                 110

Val Ser Leu Thr Gly Ile His Ala Asp Ile Gln Val Arg Trp Glu Ala
            115                 120                 125

Pro Pro Asn Ala Asp Ile Gln Lys Gly Trp Met Val Leu Glu Tyr Glu
        130                 135                 140

Leu Gln Tyr Lys Glu Val Asn Glu Thr Lys Trp Lys Met Met Asp Pro
145                 150                 155                 160

Ile Leu Ser Thr Ser Val Pro Val Tyr Ser Leu Lys Val Asp Lys Glu
                165                 170                 175

Tyr Glu Val Arg Val Arg Ser Lys Arg Arg Asn Ser Arg Asn Tyr Gly
            180                 185                 190

Glu Phe Ser Glu Val Leu Tyr Val Thr Leu Pro Gln Met
        195                 200                 205

<210> SEQ ID NO 146
<211> LENGTH: 12
<212> TYPE: PRT
<213> ORGANISM: Artificial Sequence
<220> FEATURE:
<223> OTHER INFORMATION: Humanized and/or affinity matured antibody
      sequence
<220> FEATURE:
<221> NAME/KEY: MISC_FEATURE
<222> LOCATION: (1)..(1)
<223> OTHER INFORMATION: Xaa can be T, R, or E

<400> SEQUENCE: 146

Xaa Ala Thr Ser Ser Val Ser Ser Ser Tyr Leu His
1               5                   10
```